(12) United States Patent
Feder et al.

(10) Patent No.: US 7,531,310 B2
(45) Date of Patent: May 12, 2009

(54) METHODS OF DIAGNOSING CROHN'S DISEASE BY MEASURING EXPRESSION LEVEL OF RNA ENCODING HUMAN G-PROTEIN COUPLED RECEPTOR, HGPRBMY11

(75) Inventors: John N. Feder, Belle Mead, NJ (US); Chandra S. Ramanathan, Ringoes, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 325 days.

(21) Appl. No.: 11/403,051

(22) Filed: Apr. 12, 2006

(65) Prior Publication Data

US 2006/0229272 A1    Oct. 12, 2006

Related U.S. Application Data

(63) Continuation-in-part of application No. 10/369,405, filed on Feb. 14, 2003, now abandoned, which is a continuation-in-part of application No. 09/991,225, filed on Nov. 16, 2001, now abandoned.

(60) Provisional application No. 60/305,818, filed on Jul. 16, 2001, provisional application No. 60/257,611, filed on Dec. 21, 2000, provisional application No. 60/249,613, filed on Nov. 17, 2000.

(51) Int. Cl.
*C12Q 1/68* (2006.01)
*C07K 14/705* (2006.01)

(52) U.S. Cl. ........................................ 435/6; 536/24.31

(58) Field of Classification Search ........................ None
See application file for complete search history.

(56) References Cited

U.S. PATENT DOCUMENTS

2001/0039037 A1   11/2001   Harland et al.

FOREIGN PATENT DOCUMENTS

| WO | WO9905274 | 7/1998 |
|---|---|---|
| WO | WO0119986 | 3/2001 |
| WO | WO0136471 | 5/2001 |
| WO | WO0142269 | 6/2001 |
| WO | WO0192303 | 6/2001 |
| WO | WO0159105 | 8/2001 |
| WO | WO0159113 | 8/2001 |
| WO | WO0159118 | 8/2001 |
| WO | WO0168842 | 9/2001 |
| WO | WO0172836 | 10/2001 |
| WO | WO0177149 | 10/2001 |
| WO | WO0194580 | 12/2001 |
| WO | WO0244340 | 6/2002 |

OTHER PUBLICATIONS

AbdAlla, S., et al., "AT$_1$-receptor heterodimers show enhanced G-protein activation and altered receptor sequestration", Nature, vol. 497, pp. 94-98, (2000).
Aggarwal, B. B., et al., "Apoptosis and Nuclear Factor-$_\kappa$B: A Tale of Association and Dissociation", Biochemical Pharmacology, vol. 60, pp. 1033-1039, (2000).
Akbr, M.G.K., "Molecular Cloning of a Novel P2 Purinoceptor from Human Erythroleukemia Cells", The Journal of Biological Chemistry, vol. 271, No. 31(2), pp. 18363-18367, (1996).
Alam J., et al., "Reporter Genes: Application to the Study of Mammalian Gene Transcription", Analytical Biochemistry, vol. 188, pp. 245-254, (1990).
Altschul, S. F., et al., "Gapped BLAST and PSI-BLAST: a new generation of protein database search programs", Nucleic Acids Research, vol. 25(17), pp. 3389-3402, (1997).
Baldwin Jr, A.S., "The transcription factor NF-$_\kappa$B and human disease", The Journal of Clinical Investigation, vol. 107(1), pp. 3-6, (2001).
Baldwin, A. S., "Control of oncogenesis and cancer therapy resistance by the transcription factor NF-$_\kappa$B", The Journal of Clinical Investigation, vol. 107(3), pp. 241-246, (2001).
Baldwin, J. M., "Structure and function of receptors coupled to G proteins", Current Opinion in Cell Biology, vol. 6, pp. 180-190, (1994).
Basu, S., et al., "The DNA-Dependent Protein Kinase Participates in the Activation of NF $_\kappa$B Following DNA Damage", Biochemical and Biophysical Research Communications, vol. 247, pp. 79-83, (1998).
Baud, V., et al., "EMR1, an Unusual Member in the Family of Hormone Receptors with Seven Transmembrane Segments", Genomics, vol. 26, pp. 334-344, (1995).
Baud, V., et al., "Signal transduction by tumor necrosis factor and its relatives", TRENDS in Cell Biology, vol. 11(9), pp. 372-377, (2001).
Blain, J. F., et al., "Involvement of LTD$_4$ in allergic pulmonary inflammation in mice: modulation by cysLT$_1$, antagonist MK-571", Prostaglandins, Leukotrienes and Essential Fatty Acids, vol. 62(6), pp. 361-368, (2000).
Blasius, R., et al., "A Novel Orphan G. Protein-Coupled Receptor Primarily Expressed in the Brain Is Localized on Human Chromosomal Band 2q21", Journal of Neurochemistry, vol. 70, pp. 1357-1365, (1998).

(Continued)

*Primary Examiner*—John D Ulm
(74) *Attorney, Agent, or Firm*—Stephen C. D'Amico

(57) ABSTRACT

The present invention provides novel polynucleotides encoding HGPRBMY11 polypeptides, fragments and homologues thereof. The present invention also provides polynucleotides encoding variants of the HGPRBMY11 polypeptide, HGPRBMY11v1 and HGPRBMY11v2. Also provided are vectors, host cells, antibodies, and recombinant and synthetic methods for producing these polypeptides. The invention further relates to diagnostic and therapeutic methods for applying these novel HGPRBMY11, HGPRBMY11v1, and/or HGPRBMY11v2 polypeptides to the diagnosis, treatment, and/or prevention of various diseases and/or disorders related to these polypeptides, particularly Crohn's disease. The invention further relates to screening methods for identifying agonists and antagonists of the polynucleotides and polypeptides of the present invention.

4 Claims, 18 Drawing Sheets

OTHER PUBLICATIONS

Figure 3:
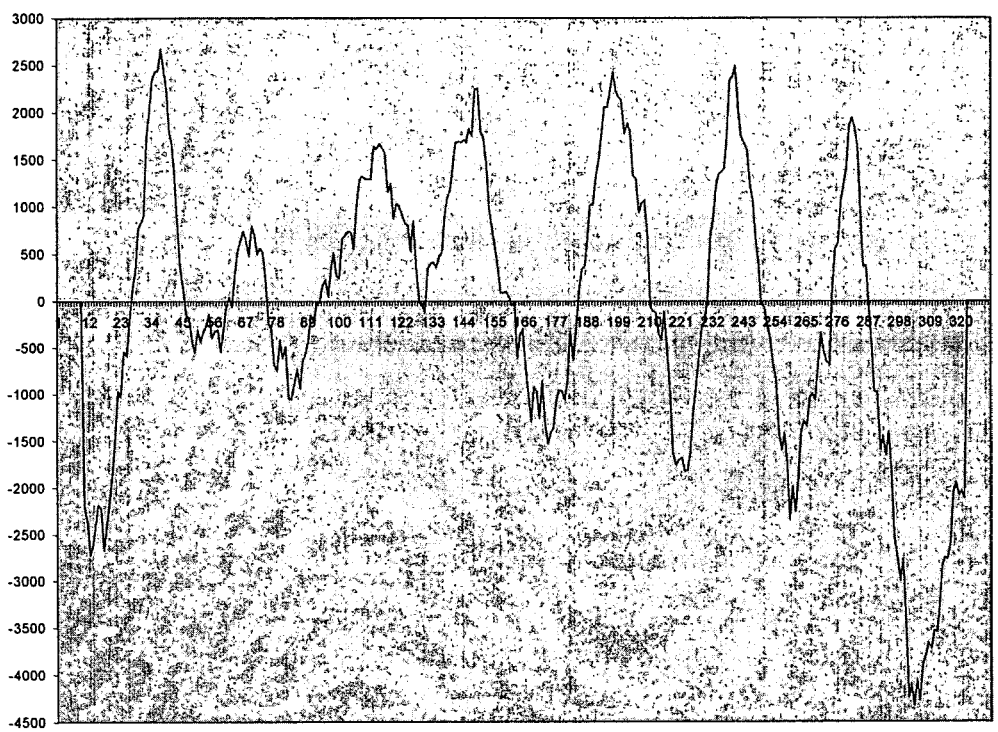

Blahos, J., et al., "A Novel Site on the Gα-protein That Recognizes Heptahelical Receptors", The Journal of Biological Chemistry, vol. 275(5), pp. 3262-3269, (2001).

Bolander, F. F., et al., Molecular Endocrinology, 2nd Edition, pp. 162-176, (1994).

Boss, V., et al., "Induction of NFAT-mediated Transcription by $G_q$—coupled Receptors in Lymphoid and Non-lymphoid Cells", The Journal of Biological Chemistry, vol. 271(18), pp. 10429-10432, (1996).

Burke, J. R., et al., "The Multisubunit $I_\kappa B$ Kinase Complex Shows Random Sequential Kinetics and Is Activated by the C-terminal Domain $I_\kappa B_\alpha$", The Journal of Biological Chemistry, vol. 273(20), pp. 12041-12046, (1998).

Chen, G., et al., "Constitutive receptor systems for drug discovery", J. Pharmacol. Toxicol., vol. 42, pp. 199-206, (1999).

Cohen, J., "Likely HIV Cofactor Found", Science, vol. 272, pp. 809-810, (1996).

Cornfield, L. J., et al., "[3H]2-Phenylaminoadenosine ([3H]CV 1808) Labels a Novel Adenosine Receptor in Rat Brain", The Journal of Pharmacology and Experimental Therapeutics, vol. 263(2), pp. 552-561, (1992).

Coughlin, S. R., "Expanding horizons for receptors coupled to G proteins: diversity and disease", Current Opinion in Cell Biology, vol. 6, pp. 191-197, (1994).

Dorn II, G. W., et al., "Low- and high-level transgenic expression of $\beta_2$-adrenergic receptors differentially affect cardiac hypertrophy and function in Gαq-overexpressing mice", Proc. Natl. Acad. Sci., vol. 96, pp. 6400-6405, (1999).

Feng, Y., et al., "HIV-1 Entry Cofactor: Functional cDNA Cloning of a Seven-Transmembrane, G Protein-Coupled Receptor", Science, vol. 272, pp. 872-877, (1996).

Feramisco, J.R., et al., "Optimal Spatial Requirements for the Location of Basic Residues in Peptide Substrates for the Cyclic AMP-dependent Protein Kinase", The Journal of Biological Chemistry, vol. 255(9), pp. 4240-4245, (1980).

Fiering, S., et al., "Single cell assay of a transcription factor reveals a threshold in transcription activated by signals emanating from the T-cell antigen receptor", Genes & Development, vol. 4, pp. 1823-1834, (1990).

George, S. E., et al., "Functional coupling of Engogenous Serotonin (5-$HT_{1B}$) and Calcitonin (C1a) Receptors in CHO Cells to a Cyclic AMP-Responsive Luciferase Reporter Gene", Journal of Neurochemistry, vol. 69(3), pp. 1278-1285, (1997).

Gosh, S., et al., "NF-$_\kappa$B and Rel Proteins: Evolutionarily Conserved Mediators of Immune Responses", Annu. Rev. Immunol., vol. 16, pp. 225-260, (1998).

Gilman, A. G., "G Proteins: Transducers of Receptor-Generated Signals", Annual Review Biochem., vol. 56, pp. 615-649, (1987).

Glass, D. B., et al., "Phosphorylation by Cyclic GMP -dependent Protein Kinase of a Synthetic Peptide Corresponding to the Autophosphorylation Site in the Enzyme", The Journal of Biological Chemistry, vol. 258(24), pp. 14797-14803, (1983).

Glass, D.B., et al., "Synthetic Peptides Corresponding to the Site Phosphorylated in 6-Phosphofructo-2kinase/Fructose-2,6-bisphospatase as Substrates of Cyclic Nucleotide-dependent Protein Kinases", The Journal of Biological Chemistry, vol. 261(6), pp. 2987-2993, (1986).

Grand, R. J. A., "Acylation of viral and eukaryotic proteins", Biochem. J., vol. 258, pp. 625-638, (1989).

Gray, J., et al., "CD97 is a Processed, Seven-Transmembrase, Heterodimeric Receptor Associated with Inflammation", The Journal of Immunology, vol. 157, pp. 5438-5447, (1996).

Hawes, B.E., et al., "Phosphatidylinositol 3-Kinase Is an Early Intermediate in the Gβγ-mediated Mitogen-activated Protein Kinase Signaling Pathway", The Journal of Biological Chemistry, vol. 271(21), pp. 12133-12136, (1996).

Hofmann, K., et al., "A Database of Membrane Spanning Protein Segments", Biol. Chem., vol. 374, pp. 166, (1993).

Horn, F., et al., "G protein-coupled receptors in Silico", J. Mol. Med., vol. 76, pp. 464-468, (1998).

Horn, F., et al., "The Interaction of Class B G Protein-Coupled Receptors with their Hormones", Receptors and Channels, vol. 5, pp. 305-314, (1998).

Ishloka, S., et al., "Effects of Pranlukast, a Cysteinyl Leukotriene Antahonist, on Bronchial Responsiveness to Methacholine in Aspirin-Intolerant Asthmatics Treated with Corticosteroids", Hiroshima J. Med. Sci.. vol. 49(2), pp. 105-108, (2000).

Jarvis, B., et al., "Montelukast A Review of its Therapeutic Potential in Persistent Asthma", Drugs, vol. 59(4), pp. 891-928, (2000).

Kaminski, N.E., et al., "Suppression of the Humoral Immune Response by Cannabinoids is Partially Mediated Through Inhibition of Adenylate Cyclase by a Pertussis Toxin-Sensitive G-Protein Coupled Mechanism", Biochemical Pharmacology, vol. 48(10), pp. 1899-1908 (Nov. 16, 1994).

Karttunen, J., et al., "Measurement of ligand-induced activation in single viable T cells using the lacZ reporter gene", Proc. Natl. Acad. Sci., vol. 88, pp. 3972-3976, (1991).

Kim, J., et al., "Structure and function in Rhodopsin: Rhodopsin mutants with a neutral amino acid at E134 have a partialy activated conformation in the dark state", Proc. Natl. Acad. Sci., vol. 94, pp. 14273-14278, (1997).

Kishimoto, A., et al., "Studies on the Phosphorylation of Myelin Basic Protein by Protein Kinase C and Adenosine 3':5'-Monophosphate-dependent Protein Kinase", The Journal of Biological Chemistry, vol. 260(23), pp. 12492-12499, (1985).

Kypson, A.P., et al., "Adenovirus-mediated gene transfer of the $B_2$-adrenergic receptor to donor hearts enhances cardiac function", Gene Therapy, vol. 6, pp. 1298-1304, (1999).

Lee, E., et al., "Leukotriene Receptor Antagonists and Synthesis Inhibitors Reverse Survival in Eosinophils of Asthmatic Individuals", Am. J. Respir. Crit. Care, Med., vol. 161, pp. 1881-1886, (2000).

Lee, E., et al., "Reversal of Human Neutrophil Survival by Leukotriene $B_4$ Receptor Blockade and 5-Lipoxygenase and 5-Lipoxygenase Activating Protein Inhibitors", Am. J. Respir. Crit. Care. Med, vol. 160, pp. 2079-2085, (1999).

Lu, Z., et al., "The Functional Topography of Transmembrane Domain 3 of the $M_1$ Muscarinic Acetylcholine Receptor, Revealed by Scanning Mutagenesis", The Journal of Biological Chemistry, vol. 274(11), pp. 7309-7315, (1999).

Meltzer, E. O., "Role of cysteinyl leukotriene receptor antagonist therapy in asthma and their potential role in allergic rhinitis based on the concept of one linked airway disease", Annals of Allergy, Asthma, & Immunology, vol. 84, pp. 176-187, (2000).

Monnot, C., et al., "Cloning and Functional Characterization of a Novel mas-Related Gene, Modulating Intracellular Angiotensin II Actions", Molecular Endocrinology, vol. 5(10), pp. 1477-1487, (1991).

Needleman, S. B., et al., "A General Method Applicable to the Search for Similarities in the Amino Acid Sequence of Two Proteins", J. Mol. Biol., vol. 48, pp. 443-453, (1970).

Offermanns, S., et al., "$G\alpha_{15}$ and $G\alpha_{16}$ Couple a Wide Variety of Receptors to Phospholipase C" The Journal of Biological Chemistry, vol. 270(25), pp. 15175-15180, (1995).

Okada, T., et al., "Activation of rhodopsin: new insigths from structural and biochemical studies", Trends in Biochemical Sciences, vol. 26(5), pp. 318-324, (2001).

Parma, J., et al., "Somatic mutations in the thyrotropin receptor gene cause hyperfunctioning thyroid adenomas", Nature, vol. 365, pp. 649-651, (1993).

Pinna, L. A., "Casein kinase 2: an 'eminence grise' in cellular regulation?", Biochimica et Biophysica Acta, vol. 1054, pp. 267-284, (1990).

Raming, K., et al., "Identification of a Novel G-protein Coupled Receptor Expressed in Distinct Brain Regions and a Defined Olfactory Zone", Receptors and Channels, vol. 6, pp. 141-151, (1998).

Raport, C. J., et al., "New members of the chemokine receptor gene family", Journal of Leukocyte Biology, vol. 59, pp. 18-23, (1996).

Rees, S., "Reporter gene systems for the study of G protein-coupled receptor signal transducation in mammalian cells", Reporter gene systems, pp. 171-221 (1999).

Salcedo, R., et al., "Human endothelial cells express CCR2 and respond to MCP-1: direct role of MCP-1 in angiogenesis and tumor progression", Blood, vol. 96(1), pp. 34-40, (2000).

Sauter, M., et al., "XX. Quinaldic Acid 4-Oxidoreductas from *Pseudomonas sp.* AK-2 Compared to other Procaryotic Molybdenum-Containing Hydroxylases", Biol. Chem. Hoppe-Seyler, vol. 374, pp. 1037-1046, (1993).

Schatz, A. R., et al., "Inhibition of Adenylate Cyclase by Δ9-Tetrahydrocannabinol in Mouse Spleen Cells: A potential Mechanism for Cannabinoid-Mediated Immunosuppression", Life Sciences, vol. 51(6), pp. PL25-30, (1992).

Selble, L. A., et al., "G protein-coupled-receptor cross-talk: the fine-tuning of multiple receptor-signaling pathways", TiPS, vol. 19, pp. 87-93, (1998).

Sica, A., et al., "Defective Expression of the Monocyte Chemotactic Protein-1 Receptor CCR2 in Macrophages Associated with Human Ovarian Carcinoma[1]", The Journal of Immunology, vol. 164, pp. 733-738, (2000).

Sidhu, S.S., et al., "[21] Phage Display for Selection of Novel Binding Peptides", Methods in Enzymology, vol. 328, pp. 333-364, (2000).

Silverman, N., et al., "NF-$_\kappa$B signaling pathways in mamalian and insect innate immunity", Gene & Development, vol. 15, pp. 2321-2342, (2001).

Strosberg, A. D., "Structure/function relationship of proteins belonging to the family of receptors coupled to GTP-binding proteins", Eur. J. Biochem., vol. 196, pp. 1-10, (1991).

Suto, C. M., et al., "Selection of an Optimal Reporter Gene for Cell-Based High Throughput Screening Assays", Journal of Biomolecular Screening, vol. 2(1), pp. 7-9, (1997).

Tao, Y., et al., "Constitutive Activation of G Protein-Coupled Receptors as a Result of Selective Substitution of a Conserved Leucine Residue in Transmembrane Helix III", Molecular Endocrinology, vol. 14(8), pp. 1272-1282, (2000).

Thomas, M. B., et al., "Chemoreceptors expressed in taste, olfactory and male reproductive tissues[1]", Gene, vol. 178, pp. 1-5, (1996).

Thornberry, N. A., et al., "Caspases: Enemies Within", Science, vol. 281, pp. 1312-1316, (1998).

Towler, D. A., et al., "The Biology and Enzymology of Eukaryotic Protein Acylation", Annual Reviews Biochem., vol. 57, pp. 69-97, (1988).

Valen, G. et al., "Nuclear Factor Kappa-B and the Heart", Journal of the American College of Cardiology, vol. 38, No. 2, pp. 307-314, (2001).

Van Rhee, A. M., et al., "Modelling the $P_{2y}$ Purinoceptor Using Rhodopsin As Template", Drug Design and Discovery, vol. 13, pp. 133-154, (1995).

Walch, L., et al., "Functional Studies of Leukotriene Receptors in Vascular Tissues", Am. J. Respir. Crit. Care, Med., vol. 161, pp. S107-S111, (2000).

Watson, S., et al., "Introduction: Seven Transmembrane Proteins", The G-protein Linked Receptor Facts Book, pp. 2-6, (1994).

Watson, S., et al., "Adenosine and adenine nucleotides", The G-protein Linked Receptor Facts Book, pp. 19-31, (1994).

Webb, T. E., et al., "Cloning and functional expression of a brain G-protein-coupled ATP receptor", FEBS, vol. 324(2), pp. 219-225, (1993).

Wess, J., "G-protein-coupled receptors: molecular mechanisms involved in receptor activation and selectivity of G-protein receognition", The FASEB Journal, vol. 11, pp. 346-354, (1997).

Whitney, M., et al., "A genome-wide functional assay of signal transduction in living mammalian cells", Nature Biotechnology, vol. 16, pp. 1329-1333, (1998).

Woodgett, J. R., et al., "Substrate specificity of protein kinase C", Eur. J. Biochem., vol. 161, pp. 177-184, (1986).

Yokomizo, T., et al., "A G-protein-coupled receptor for leukotriene $B_4$ that mediates chemotaxis", Nature, vol. 387, pp. 620-624, (1997).

Yoshida, S. et al., "Effect of pranlukast on bronchial inflammation in patients with asthma", Clinical and Experimental Allergy, vol. 30, pp. 1008-1014, (2000).

Yoshida, S. et al., "Efficacy of leukotriene receptor antagonist in bronchial hyperresponsiveness and hypersensitivity to analgesic in aspirin-intolerant asthma", Clinical and Experimental Allergy, vol. 30, pp. 64-70, (2000).

Zlokarnik, G., et al., "Quantitation of Transcription and Clonal Selection of Single Living Cells with β-Lactamase as Recporter", Science, vol. 279, pp. 84-88, (1998).

NCBI Entrez Accession No. AL137118 (gi:11034480), Dunn, M., Feb. 9, 2005.

NCBI Entrez Accession No. CAA36884 (gi:49652), Klein, H., Sep. 12, 1993.

NCBI Entrez Accession No. P32250 (gi:417040), Kaplan, M. H., et al., Jan. 25, 2005.

NCBI Entrez Accession No. P34996 (gi:464327), Webb, T. E., et al., Oct. 25, 2004.

NCBI Entrez Accession No. P49651 (gi:1352695), Tokuyama, Y., et al., May 1, 2005.

NCBI Entrez Accession No. P49652 (gi:135293), Fillz, T. M., et al., Oct. 25, 2004.

NCBI Entrez Accession No. Q13304 (gi:21264435), Raport, C. J., et al., Oct. 25, 2004.

NCBI Entrez Accession No. X58122 (gi:34996), Labeit, S., et al., Feb. 17, 1997.

NCBI Entrez Accession No. XP010411 (gi:11422069), Apr. 16, 2001.

Database EMBL Online, Oct. 2, 2000, Retrieved from Database Accession No. AF254664, XP002237607.

Heise et al. (2000) J. of Biological Chemistry 275(39)30531-30536.

Sarau et al. (1999) Amer. Society for Pharmacology and Exp. Therapeutics 56:657-663.

Marchese et al. (1999) Genomics 56:12-21.

Stadel et al. (1997) Tips, Elsevier Science 18:430-437.

Wilson et al. (1998) British J. of Pharmacology 125:1387-1392.

NCBI Accession No. gi:10716136, H. Suga, Oct. 6, 2000.

NCBI Accession No. gi:14582394, Nothacker, et al., Jul. 2, 2001.

NCBI Accession No. gi:13311206, M. Dunn, Feb. 14, 2001.

FIG. 1A

```
  1   CCCACGCGTCCGGGGAGCTTGCACTAACATCTACAATGGCTTCTAAAAAGCACAGATGAC   60

61   CTGCTACACTTCCTGACTTGCTTGCTATTGGTTGGCACTGTTCATAAATATAATTTGCTC  120

121   TTTCACTTTTCTTTGAAATGAGCAACCTGAATTACTCGGAGGAGAAAGGCAGGAGAGATA  180

181   GAGGCAGCAGAAGCCAGGGCAGCTGAAAGACAGAGACCTTCAGTCTGAACCAACAACAAG  240

241   CAAAGTTAAATTATGGATATCCAAGGGAGTCTATAGAAGGTCCATGCAAGACATTTTGAC  300

301   TACTTGTCTGAACTAGATATCCCTTGAATGTGCACACAAAAAGTGAATGGGTCATTTGAT  360

361   AAGGGAAAACTAGGTTCCAAGATGGCTGAATAGGAAGAGCTCCAGTCTGCAGATCCCAGT  420

421   GTGAGCAACGTGGAAGATGGGTGATTTCTGCATTTCCAACTGAGCATGGAGAGAAAAATT  480

481   TATGTCCTTGCAACCATCCATCTCCGTATCAGAAATGGAACCAAATGGCACCTTCAGCAA  540
  1                                       M   E   P   N   G   T   F   S   N   9

541   TAACAACAGCAGGAACTGCACAATTGAAAACTTCAAGAGAGAATTTTTCCCAATTGTATA  600
 10    N   N   S   R   N   C   T   I   E   N   F   K   R   E   F   F   P   I   V   Y   29

601   TCTGATAATATTTTTCTGGGGAGTCTTGGGAAATGGGTTGTCCATATATGTTTTCCTGCA  660
 30    L   I   I   F   F   W   G   V   L   G   N   G   L   S   I   Y   V   F   L   Q   49

661   GCCTTATAAGAAGTCCACATCTGTGAACGTTTTCATGCTAAATCTGGCCATTTCAGATCT  720
 50    P   Y   K   K   S   T   S   V   N   V   F   M   L   N   L   A   I   S   D   L   69

721   CCTGTTCATAAGCACGCTTCCCTTCAGGGCTGACTATTATCTTAGAGGCTCCAATTGGAT  780
 70    L   F   I   S   T   L   P   F   R   A   D   Y   Y   L   R   G   S   N   W   I   89

781   ATTTGGAGACCTGGCCTGCAGGATTATGTCTTATTCCTTGTATGTCAACATGTACAGCAG  840
 90    F   G   D   L   A   C   R   I   M   S   Y   S   L   Y   V   N   M   Y   S   S   109

841   TATTTATTTCCTGACCGTGCTGAGTGTTGTGCGTTTCCTGGCAATGGTTCACCCCTTTCG  900
110    I   Y   F   L   T   V   L   S   V   V   R   F   L   A   M   V   H   P   F   R   129
```

FIG. 1B

```
 901  GCTTCTGCATGTCACCAGCATCAGGAGTGCCTGGATCCTCTGTGGGATCATATGGATCCT   960
 130   L   L   H   V   T   S   I   R   S   A   W   I   L   C   G   I   I   W   I   L   149

961  TATCATGGCTTCCTCAATAATGCTCCTGGACAGTGGCTCTGAGCAGAACGGCAGTGTCAC  1020
 150   I   M   A   S   S   I   M   L   L   D   S   G   S   E   Q   N   G   S   V   T   169

1021  ATCATGCTTAGAGCTGAATCTCTATAAAATTGCTAAGCTGCAGACCATGAACTATATTGC  1080
 170   S   C   L   E   N   L   Y   K   I   A   K   L   Q   T   M   N   Y   I   A   189

1081  CTTGGTGGTGGGCTGCCTGCTGCCATTTTTCACACTCAGCATCTGTTATCTGCTGATCAT  1140
 190   L   V   V   G   C   L   L   P   F   F   T   L   S   I   C   Y   L   L   I   I   209

1141  TCGGGTTCTGTTAAAAGTGGAGGTCCCAGAATCGGGGCTGCGGGTTTCTCACAGGAAGGC  1200
 210   R   V   L   L   K   V   E   V   P   E   S   G   L   R   V   S   H   R   K   A   229

1201  ACTGACCACCATCATCATCACCTTGATCATCTTCTTCTTGTGTTTCCTGCCCTATCACAC  1260
 230   L   T   T   I   I   I   T   L   I   I   F   F   L   C   F   L   P   Y   H   T   249

1261  ACTGAGGACCGTCCACTTGACGACATGGAAAGTGGGTTTATGCAAAGACAGACTGCATAA  1320
 250   L   R   T   V   H   L   T   T   W   K   V   G   L   C   K   D   R   L   H   K   269

1321  AGCTTTGGTTATCACACTGGCCTTGGCAGCAGCCAATGCCTGCTTCAATCCTCTGCTCTA  1380
 270   A   L   V   I   T   L   A   A   A   N   A   C   F   N   P   L   L   Y   289

1381  TTACTTTGCTGGGGAGAATTTTAAGGACAGACTAAAGTCTGCACTCAGAAAAGGCCATCC  1440
 290   Y   F   A   G   E   N   F   K   D   R   L   K   S   A   L   R   K   G   H   P   309

1441  ACAGAAGGCAAAGACAAAGTGTGTTTTCCCTGTTAGTGTGTGGTTGAGAAAGGAAACAAG  1500
 310   Q   K   A   K   T   K   C   V   F   P   V   S   V   W   L   R   K   E   T   R   329

1501  AGTATAAGGAGCTCTTAGATGAGACCTGTTCTTGTATCCTTGTGTCCATCTTCATTCACT  1560
 330   V   *                                                        331

1561  CATAGTCTCCAAATGACTTTGTATTTACATCACTCCCAACAAATGTTGATTCTTAATATT  1620

1621  TAGTTGACCATTACTTTTGTTAATAAGACCTACTTCAAAAATTTTATTCAGTGTAAAAAA  1680

1681  AAAAAAAAAAAAAAAAAAAAAAAAAAAA  1708
```

FIG. 2A

```
                    1                                                          50
HGPRBMY11     (1)   -----MSLQPSISVSEMEPNG-----------TFSNNNSRNCIIEN--FK
HGPRBMY11v1   (1)   MERKFMSLQPSISVSEMEPNG-----------TFSNNNSRNCIIEN--FK
P2Y5_CHICK    (1)   -------------------------------MVSNCSTEDS-FK
P2YR_CHICK    (1)   MTEALISAALNGIQPELLAGG-----------WAAGNATKCSLTKTGFQ
P2YR_MELGA    (1)   MTEALISAALNGIQPELLAGG-----------WAAGNASTKCSLTKTGFQ
P2YR_RAT      (1)   MTEVPWSAVPNGIDAAELAGLGSLWGNSTIASTAAVSSSFRCALIKTGFQ
Q9Y271        (1)   ---------------MDETG-----------NLTVSSATCHDTIDDER
GPRH_HUMAN    (1)   ----------MNGLEVAPPG---------LITNFSLATAEQCGQETPLE 51                                                         100
HGPRBMY11    (22)   REFFPIVYLIIFFWGVLGNGLSIYVFLQPYKKSTSVNVFMLNLAISDLLF
HGPRBMY11v1  (38)   REFFPIVYLIIFFWGVLGNGLSIYVFLQPYKKSTSVNVFMLNLAISDLLF
P2Y5_CHICK   (14)   YTLYGCVFSMVFVLCLIANCVAIYIFTTLKVRNEITIYMLNLAISDLLF
P2YR_CHICK   (40)   FYYLPTVYILVFITGFLGNSVAIWMFVFHMRPWSGISVYMFNLALADFLY
P2YR_MELGA   (40)   FYYLPTVYILVFITGFLGNSVAIWMFVFHMRPWSGISVYMFNLALADFLY
P2YR_RAT     (51)   FYYLPAVYLVFIIGFLGNSVAIWMFVFHMKPWSGISVYMFNLALADFLY
Q9Y271       (23)   NQVYSTLYSMISVVGFFGNFVLYVLIKTYKKSAFQVYMINLAMADLLC
GPRH_HUMAN   (31)   NMLFASFYLLDFILALVGNTLALWLFIRDHKSGTPANVFLMHLAVADLSC 101                                                        150
HGPRBMY11    (72)   ISTLPFRADYYLRGSNWIFGDLACRIMSYSLYVNMYSSIYFLTVLSVVRF
HGPRBMY11v1  (88)   ISTLPFRADYYLRGSNWIFGDLACRIMSYSLYVNMYSSIYFLTVLSVVRF
P2Y5_CHICK   (64)   VETLPFRIYYFVVRN-WPFGDVLCKTSVTLFYTNMYGSILFLTCISVDRF
P2YR_CHICK   (90)   VLTLPALIFYYFNKTDWIFGDVMCKLQRFIFHVNLYGSILFLTCISVHRY
P2YR_MELGA   (90)   VLTLPALIFYYFNKTDWIFGDVMCKLQRFIFHVNLYGSILFLTCISVHRY
P2YR_RAT    (101)   VLTLPALIFYYFNKTDWIFGDVMCKLQRFIFHVNLYGSILFLTCISAHRY
Q9Y271       (73)   VCTLPLRVVYYVHKGIWLFGDFLCRLSTYALYVNLYCSIFFMTAMSFFRC
GPRH_HUMAN   (81)   VLVLPTRIVYHFSGNHWPFGEIACRLTGFLFYLNMYASIYFLTCISADRF 151                                                        200
HGPRBMY11   (122)   LAMVHPFRLLHVTSIRSAWILCGIIWILIMASSIMLLDS----GSEQNGSV
HGPRBMY11v1 (138)   LAMVHPFRLLHVTSIRSAWILCGIIWILIMASSIMLLDS----GSEQNGSV
P2Y5_CHICK  (113)   LAIVHPFRSKTLRIKRNARIVCVAVWITVLAGSTPASFFQSTNRQNNTEQ
P2YR_CHICK  (140)   TGVVHPLKSLGRLKKKNAVYVSSLVWALVMAVIAPILFYSGTGVRRNKTI
P2YR_MELGA  (140)   TGVVHPLKSLGRLKKKNAVYVSSLVWALVMAVIAPILFYSGTGVRRNKTI
P2YR_RAT    (151)   SGVVYPLKSLGRLKKKNAIYVSVLVWLIVVAISPILFYSGTGIRKNKTV
Q9Y271      (123)   IAIVFPVQNINLVTQKKAREVCVGIWIFVILTSSPELMAKPQKDEKNNTK
GPRH_HUMAN  (131)   LAIVHPVKSLKLRRPLYAHLACAFLWVVAVAMAPLLVSPQTVQTNHTVV 201                                                        250
HGPRBMY11   (169)   TSCLE--LNLYKIAKLQTMNYIALVVGCLIPFFTLSICYLLIIRVLLKVE
HGPRBMY11v1 (185)   TSCLE--LNLYKIAKLQTMNYIALVVGCLIPFFTLSICYLLIIRVLLKVE
P2Y5_CHICK  (163)   RTCFENFPESTWKTYLSRIVIFIEIVGFFIPLILNVTCSTMVLRTLNKPL
P2YR_CHICK  (190)   TCYDT--TADEYLRSYFVYSMCITVFMCIPFIVILGCYGLIVKALIYKD
P2YR_MELGA  (190)   TCYDT--TADEYLRSYFVYSMCITVFMCIPFIVILGCYGLIVKALIYKD
P2YR_RAT    (201)   TCYDS--TSDEYLRSYFIYSMCITVAMFCIPLVLILGCYGLIVRALIYKD
Q9Y271      (173)   CFEPP--QDNQTKNHVLVLHYVSLFVGFIIPFVIITVCYTMIILLLKKS
GPRH_HUMAN  (181)   CLQLY-------REKASHHALVSLAVAFTEPFITTVTCYLLIIRSLRQGL
```

FIG. 2B

```
                    251                                                   300
HGPRBMY11    (217)  VPESGLRVSHRKALTTIIITLIIFFLCFLPYHILRTVHL------TTWKV
HGPRBMY11v1  (233)  VPESGLRVSHRKALTTIIITLIIFFLCFLPYHILRTVHL------TTWKV
P2Y5_CHICK   (213)  ILSRNKLS-KKKVLKMIFVHLVIFCFCMPYNITLILYSLMR--TQTWIN
P2YR_CHICK   (238)  LDNSPLR---RKSIYLVIIVLTVFAVSYLPEHVMKTLNLRARLDFQTPQM
P2YR_MELGA   (238)  LDNSPLR---RKSIYLVIIVLTVFAVSYLPEHVMKTLNLRARLDFQTPQM
P2YR_RAT     (249)  LDNSPLR---RKSIYLVIIVLTVFAVSYIPEHVMKTMNLRARLDFQTPEM
Q9Y271       (221)  MKKNLSS--HKKAIGMIMVVTAAFLVSFMPYHIQRTIELHFLHN--ETKP
GPRH_HUMAN   (224)  RVEKRLK---TKAVRMIAIVLAIFLVCFMPYHVNRSVYVLHYR--SHGAS 301                                                   350
HGPRBMY11    (261)  GLCKDRLHKALVITLALAAANACFNPLLYMFAGENFKDRLKSALRKGHPQ
HGPRBMY11v1  (277)  GLCKDRLHKALVITLALAAANACFNPLLYMFAGENFKDRLKSALRKGHPQ
P2Y5_CHICK   (260)  CSVVTAVRTMYPVTLCIAVSNCCFDPIMYMETSDTNSILDK--KQQ--VH
P2YR_CHICK   (285)  CAFNDKVYAIYQVTRGLASLNSCVDPILYFLAGDTFRRRLSRATRKSSRR
P2YR_MELGA   (285)  CAFNDKVYAIYQVTRGLASLNSCVDPILYFLAGDTFRRRLSRATRKSSRR
P2YR_RAT     (296)  CDFNDRVYAIYQVTRGLASLNSCVDPILYFLAGDTFRRRLSRATRKASRR
Q9Y271       (267)  CDSVLRMQKSVVTPLSLAASNCCFDPLLYFSCGNFRKRLS-IFRKHSLS
GPRH_HUMAN   (269)  CATQRILALANRITSCLTSLNGALDPIMYFFVAEKFRHALCNLLCGKRLK 351              379
HGPRBMY11    (311)  KAK-TKCVFPVSVWLRKETRV--------
HGPRBMY11v1  (327)  KAK-TKCVFPVSVWLRKETRV--------
P2Y5_CHICK   (306)  QNT--------------------------
P2YR_CHICK   (335)  SEP-NVQSKSEEMTLNILTEYKQNGDTSL
P2YR_MELGA   (335)  SEP-NVQSKSEEMTLNILTEYKQNGDTSL
P2YR_RAT     (346)  SEA-NLQSKSEEMTLNILSEFKQNGDTSL
Q9Y271       (316)  SVT-YVPRKKASLBEKGEEICKV------
GPRH_HUMAN   (319)  GPPPSEEGKTNESSLSAKSEL--------
```

Expression Profiling of Novel Human GPCR, HG PRBMY 11

FIG. 5

HGPRBMY11

| Protein | Genbank ID | Identities | Similarities |
|---|---|---|---|
| human cysteinyl leukotriene receptor | gi\|11422069 | 37% | 49% |
| chick purinergic receptor 5 | gi\|P32250 | 36% | 46% |
| human G-protein-coupled receptor GPR17 | gi\|Q13304 | 36% | 46% |
| chick purinergic receptor | gi\|P34996 | 30% | 45% |
| turkey purinergic receptor | gi\|P49652 | 30% | 45% |
| rat purinergic receptor | gi\|P49651 | 30% | 44% |

HGPRBMY11v1

| Protein | Genbank ID | Identities | Similarities |
|---|---|---|---|
| human cysteinyl leukotriene receptor | gi\|11422069 | 37.2% | 49% |
| chick purinergic receptor 5 | gi\|P32250 | 36.7% | 46.1% |
| human G-protein-coupled receptor GPR17 | gi\|Q13304 | 36.2% | 46.1% |
| chick purinergic receptor | gi\|P34996 | 29.5% | 43.9% |
| turkey purinergic receptor | gi\|P49652 | 29.8% | 44.2% |
| rat purinergic receptor | gi\|P49651 | 29.6% | 44% |

FIG. 6A

```
  1  ATGGAGAGAAAATTTATGTCCTTGCAACCATCCATCTCCGTATCAGAAATGGAACCAAAT   60
  1   M  E  R  K  F  M  S  L  Q  P  S  I  S  V  S  E  M  E  P  N   20

61  GGCACCTTCAGCAATAACAACAGCAGGAACTGCACAATTGAAAACTTCAAGAGAGAATTT  120
 21   G  T  F  S  N  N  N  S  R  N  C  T  I  E  N  F  K  R  E  F   40

121  TTCCCAATTGTATATCTGATAATATTTTTCTGGGGAGTCTTGGGAAATGGGTTGTCCATA  180
 41   F  P  I  V  Y  L  I  I  F  F  W  G  V  L  G  N  G  L  S  I   60

181  TATGTTTTCCTGCAGCCTTATAAGAAGTCCACATCTGTGAACGTTTTCATGCTAAATCTG  240
 61   Y  V  F  L  Q  P  Y  K  K  S  T  S  V  N  V  F  M  L  N  L   80

241  GCCATTTCAGATCTCCTGTTCATAAGCACGCTTCCCTTCAGGGCTGACTATTATCTTAGA  300
 81   A  I  S  D  L  L  F  I  S  T  L  P  F  R  A  D  Y  Y  L  R  100

301  GGCTCCAATTGGATATTTGGAGACCTGGCCTGCAGGATTATGTCTTATTCCTTGTATGTC  360
101   G  S  N  W  I  F  G  D  L  A  C  R  I  M  S  Y  S  L  Y  V  120

361  AACATGTACAGCAGTATTTATTTCCTGACCGTGCTGAGTGTTGTGCGTTTCCTGGCAATG  420
121   N  M  Y  S  S  I  Y  F  L  T  V  L  S  V  V  R  F  L  A  M  140

421  GTTCACCCCTTTCGGCTTCTGCATGTCACCAGCATCAGGAGTGCCTGGATCCTCTGTGGG  480
141   V  H  P  F  R  L  L  H  V  T  S  I  R  S  A  W  I  L  C  G  160

481  ATCATATGGATCCTTATCATGGCTTCCTCAATAATGCTCCTGGACAGTGGCTCTGAGCAG  540
161   I  I  W  I  L  I  M  A  S  S  I  M  L  L  D  S  G  S  E  Q  180

541  AACGGCAGTGTCACATCATGCTTAGAGCTGAATCTCTATAAAATTGCTAAGCTGCAGACC  600
181   N  G  S  V  T  S  C  L  E  L  N  L  Y  K  I  A  K  L  Q  T  200

601  ATGAACTATATTGCCTTGGTGGTGGGCTGCCTGCTGCCATTTTTCACACTCAGCATCTGT  660
201   M  N  Y  I  A  L  V  V  G  C  L  L  P  F  F  T  L  S  I  C  220

661  TATCTGCTGATCATTCGGGTTCTGTTAAAAGTGGAGGTCCCAGAATCGGGGCTGCGGGTT  720
221   Y  L  L  I  I  R  V  L  L  K  V  E  V  P  E  S  G  L  R  V  240

721  TCTCACAGGAAGGCACTGACCACCATCATCATCACCTTGATCATCTTCTTCTTGTGTTTC  780
241   S  H  R  K  A  L  T  T  I  I  I  T  L  I  I  F  F  L  C  F  260

781  CTGCCCTATCACACACACTGAGGACCGTCCACTTGACGACATGGAAAGTGGGTTTATGCAAA  840
261   L  P  Y  H  T  L  R  T  V  H  L  T  T  W  K  V  G  L  C  K  280
```

FIG. 6B

```
 841  GACAGACTGCATAAAGCTTTGGTTATCACACTGGCCTTGGCAGCAGCCAATGCCTGCTTC   900
 281   D  R  L  H  K  A  L  V  I  T  L  A  L  A  A  A  N  A  C  F   300

901  AATCCTCTGCTCTATTACTTTGCTGGGGAGAATTTTAAGGACAGACTAAAGTCTGCACTC   960
 301   N  P  L  L  Y  Y  F  A  G  E  N  F  K  D  R  L  K  S  A  L   320

961  AGAAAAGGCCATCCACAGAAGGCAAAGACAAAGTGTGTTTTCCCTGTTAGTGTGTGGTTG  1020
 321   R  K  G  H  P  Q  K  A  K  T  K  C  V  F  P  V  S  V  W  L   340

1021  AGAAAGGAAACAAGAGTATAA  1041
 341   R  K  E  T  R  V       346
```

FIG. 13
Cho NFAT Ga15 Control (Fluorescent vs. Bright Field)
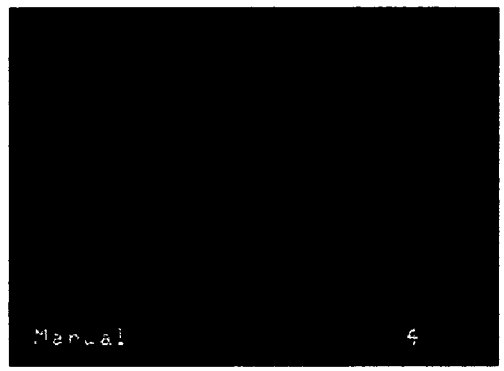 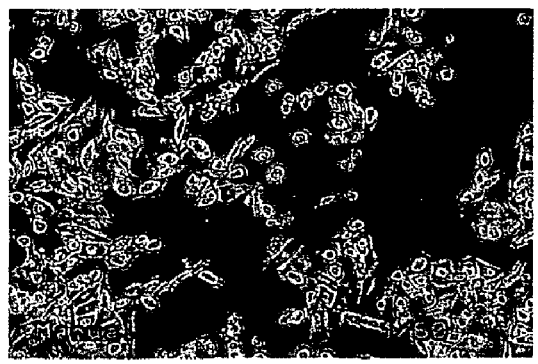
Cho NFAT Ga15 BMY11 (Fluorescent vs. Bright Field)
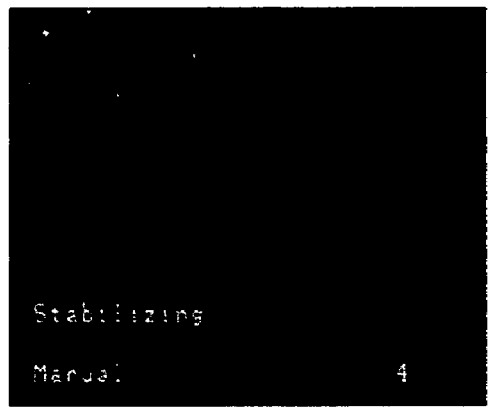 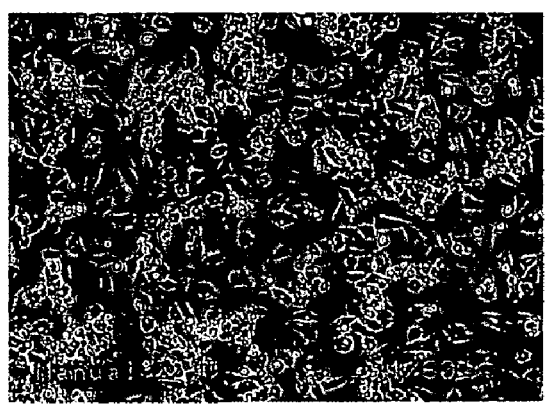

FIG. 14
a. Cho-NFAT CRE
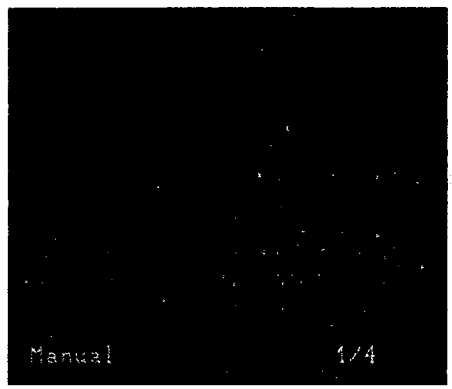
b. Cho-NFAT CRE + F/T/P
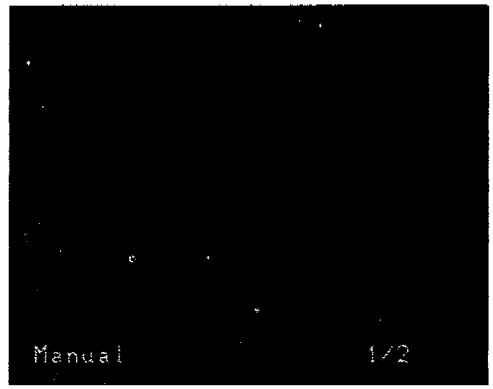
c. Cho-NFAT CRE oGPCR-Intermediate
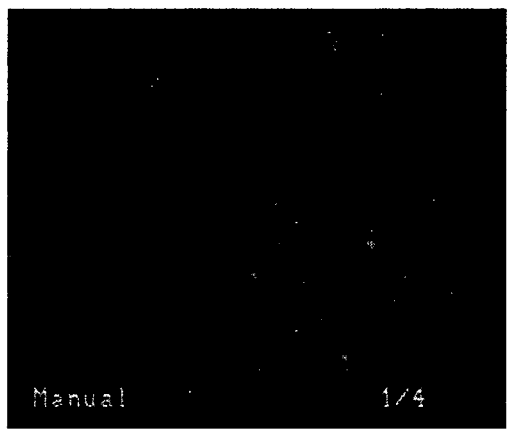
d. Cho-NFAT CRE oGPCR High
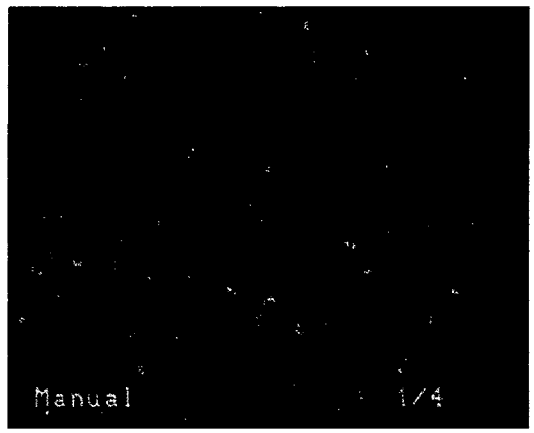

FIG. 15A

```
  1  ATGTCCTTGCAACCATCCATCTCCGTATCAGAAATGGAACCAAATGGCACCTTCAGCAAT   60
  1   M   S   L   Q   P   S   I   S   V   S   E   M   E   P   N   G   T   F   S   N    20

61  AACAACAGCAGGAACTGCACAATTGAAAACTTCAAGAGAGAATTTTTCCCAATTGTATAT  120
 21   N   N   S   R   N   C   T   I   E   N   F   K   R   E   F   F   P   I   V   Y    40

121  CTGATAATATTTTTCTGGGGAGTCTTGGGAAATGGGTTGTCCATATATGTTTTCCTGCAG  180
 41   L   I   I   F   F   W   G   V   L   G   N   G   L   S   I   Y   V   F   L   Q    60

181  CCTTATAAGAAGTCCACATCTGTGAACGTTTTCATGCTAAATCTGGCCATTTCAGATCTC  240
 61   P   Y   K   K   S   T   S   V   N   V   F   M   L   N   L   A   I   S   D   L    80

241  CTGTTCATAAGCACGCTTCCCTTCAGGGCTGACTATTATCTTAGAGGCTCCAATTGGATA  300
 81   L   F   I   S   T   L   P   F   R   A   D   Y   Y   L   R   G   S   N   W   I   100

301  TTTGGAGACCTGGCCTGCAGGATTATGTCTTATTCCTTGTATGTCAACATGTACAGCAGT  360
101   F   G   D   L   A   C   R   I   M   S   Y   S   L   Y   V   N   M   Y   S   S   120

361  ATTTATTTCCTGACCGTGCTGAGTGTTGTGCGTTTCCTGGCAATGGTTCACCCCTTTCGG  420
121   I   Y   F   L   T   V   L   S   V   V   R   F   L   A   M   V   H   P   F   R   140

421  CTTCTGCATGTCACCAGCATCAGGAGTGCCTGGATCCTCTGTGGGATCATATGGATCCTT  480
141   L   L   H   V   T   S   I   R   S   A   W   I   L   C   G   I   I   W   I   L   160

481  ATCATGGCTTCCTCAATAATGCTCCTGGACAGTGGCTCTGAGCAGAACGGCAGTGTCACA  540
161   I   M   A   S   S   I   M   L   L   D   S   G   S   E   Q   N   G   S   V   T   180

541  TCATGCTTAGAGCTGAATCTCTATAAAATTGCTAAGCTGCAGACCATGAACTATATTGCC  600
181   S   C   L   E   L   N   L   Y   K   I   A   K   L   Q   T   M   N   Y   I   A   200

601  TTGGTGGTGGGCTGCCTGCTGCCATTTTTCACACTCAGCATCTGTTATCTGCTGATCATT  660
201   L   V   V   G   C   L   L   P   F   F   T   L   S   I   C   Y   L   L   I   I   220

661  CGGGTTCTGTTAAAAGTGGAGGTCCCAGAATCGGGGCTGCGGGTTTCTCACAGGAAGGCA  720
221   R   V   L   L   K   V   E   V   P   E   S   G   L   R   V   S   H   R   K   A   240

721  CTGACCACCATCATCATCACCTTGATCATCTTCTTCTTGTGTTTCCTGCCCTATCACACA  780
241   L   T   T   I   I   I   T   L   I   I   F   F   L   C   F   L   P   Y   H   T   260
```

FIG. 15B

```
 781   CTGAGGACCGTCCACTTGACGACATGGAAAGTGGGTTTATGCAAAGACAGACTGCATAAA    840
 261    L  R  T  V  H  L  T  T  W  K  V  G  L  C  K  D  R  L  H  K    280

841   GCTTTGGTTATCACACTGGCCTTGGCAGCAGCCAATGCCTGCTTCAATCCTCTGCTCTAT    900
 281    A  L  V  I  T  L  A  L  A  A  A  N  A  C  F  N  P  L  L  Y    300

901   TACTTTGCTGGGGAGAATTTTAAGGACAGACTAAAGTCTGCACTCAGAAAAGGCCATCCA    960
 301    Y  F  A  G  E  N  F  K  D  R  L  K  S  A  L  R  K  G  H  P    320

961   CAGAAGGCAAAGACAAAGTGTGTTTTCCCTGTTAGTGTGTGGTTGAGAAAGGAAACAAGA   1020
 321    Q  K  A  K  T  K  C  V  F  P  V  S  V  W  L  R  K  E  T  R    340

1021   GTATAA   1026
 341    V      341
```

METHODS OF DIAGNOSING CROHN'S DISEASE BY MEASURING EXPRESSION LEVEL OF RNA ENCODING HUMAN G-PROTEIN COUPLED RECEPTOR, HGPRBMY11

This application is a continuation-in-part application of non-provisional application U.S. Ser. No. 10/369,405, filed on Feb. 14, 2003 now abandoned, which is a continuation-in-part application of non-provisional application U.S. Ser. No. 09/991,225, filed on Nov. 16, 2001 now abandoned, which claims benefit to provisional application U.S. Ser. No. 60/249,613, filed Nov. 17, 2000; to provisional application U.S. Ser. No. 60/257,611, filed Dec. 21, 2000; and to provisional application U.S. Ser. No. 60/305,818, filed Jul. 16, 2001.

FIELD OF THE INVENTION

The present invention provides novel polynucleotides encoding HGPRBMY11 polypeptides, fragments and homologues thereof. The present invention also provides polynucleotides encoding variants of the HGPRBMY11 polypeptide, HGPRBMY11v1 and HGPRBMY11v2. Also provided are vectors, host cells, antibodies, and recombinant and synthetic methods for producing said polypeptides. The invention further relates to diagnostic and therapeutic methods for applying these novel HGPRBMY11, HGPRBMY11v1, and/or HGPRBMY11v2 polypeptides to the diagnosis, treatment, and/or prevention of various diseases and/or disorders related to these polypeptides, particularly gastrointestinal diseases and/or disorders, Crohn's disease, ovarian cancer, and diseases and disorders related to aberrant NFKB modulation. The invention further relates to screening methods for identifying agonists and antagonists of the polynucleotides and polypeptides of the present invention.

BACKGROUND OF THE INVENTION

Regulation of cell proliferation, differentiation, and migration is important for the formation and function of tissues. Regulatory proteins such as growth factors control these cellular processes and act as mediators in cell-cell signaling pathways. Growth factors are secreted proteins that bind to specific cell surface receptors on target cells. The bound receptors trigger intracellular signal transduction pathways which activate various downstream effectors that regulate gene expression, cell division, cell differentiation, cell motility, and other cellular processes. Some of the receptors involved in signal transduction by growth factors belong to the large superfamily of G-protein coupled receptors (GPCRs) which represent one of the largest receptor superfamilies known.

GPCRs are biologically important as their malfunction has been implicated in contributing to the onset of many diseases, which include, but are not limited to, Alzheimer's, Parkinson, diabetes, dwarfism, color blindness, retinal pigmentosa and asthma. Also, GPCRs have also been implicated in depression, schizophrenia, sleeplessness, hypertension, anxiety, stress, renal failure and in several cardiovascular, metabolic, neuro, oncology and immune disorders (F Horn, G Vriend, J. Mol. Med. 76: 464-468, 1998.). They have also been shown to play a role in HIV infection (Y Feng, C C Broder, P E Kennedy, E A Berger, Science 272:872-877, 1996).

GPCRs are integral membrane proteins characterized by the presence of seven hydrophobic transmembrane domains which together form a bundle of antiparallel alpha (a) helices. The 7 transmembrane regions are designated as TM1, TM2, TM3, TM4, TM5, TM6, and TM7. These proteins range in size from under 400 to over 1000 amino acids (Strosberg, A. D. (1991) Eur. J. Biochem. 196: 110; Coughlin, S. R. (1994) Curr. Opin. Cell Biol. 6: 191-197). The amino-terminus of a GPCR is extracellular, is of variable length, and is often glycosylated. The carboxy-terminus is cytoplasmic and generally phosphorylated. Extracellular loops of GPCRs alternate with intracellular loops and link the transmembrane domains. Cysteine disulfide bridges linking the second and third extracellular loops may interact with agonists and antagonists. The most conserved domains of GPCRs are the transmembrane domains and the first two cytoplasmic loops. The transmembrane domains account for structural and functional features of the receptor. In most G-protein coupled receptors, the bundle of a helices forms a ligand-binding pocket formed by several G-protein coupled receptor transmembrane domains.

Characterization of the HGPRBMY11 polypeptide of the present invention led to the determination that it is involved in NFkB pathway through modulation of the IkB protein, either directly or indirectly.

The fate of a cell in multicellular organisms often requires choosing between life and death. This process of cell suicide, known as programmed cell death or apoptosis, occurs during a number of events in an organisms life cycle, such as for example, in development of an embryo, during the course of an immunological response, or in the demise of cancerous cells after drug treatment, among others. The final outcome of cell survival versus apoptosis is dependent on the balance of two counteracting events, the onset and speed of caspase cascade activation (essentially a protease chain reaction), and the delivery of antiapoptotic factors which block the caspase activity (Aggarwal B. B. Biochem. Pharmacol. 60, 1033-1039, (2000); Thornberry, N. A. and Lazebnik, Y. Science 281, 1312-1316, (1998)).

The production of antiapoptotic proteins is controlled by the transcriptional factor complex NF-kB. For example, exposure of cells to the protein tumor necrosis factor (TNF) can signal both cell death and survival, an event playing a major role in the regulation of immunological and inflammatory responses (Ghosh, S., May, M. J., Kopp, E. B. Annu. Rev. Immunol. 16, 225-260, (1998); Silverman, N. and Maniatis, T., Genes & Dev. 15, 2321-2342, (2001); Baud, V. and Karin, M., Trends Cell Biol. 11, 372-377, (2001)). The antiapoptotic activity of NF-kB is also crucial to oncogenesis and to chemo- and radio-resistance in cancer (Baldwin, A. S., J. Clin. Inves. 107, 241-246, (2001)).

Nuclear Factor-kB (NF-kB), is composed of dimeric complexes of p50 (NF-kB1) or p52 (NF-kB2) usually associated with members of the Rel family (p65, c-Rel, Rel B) which have potent transactivation domains. Different combinations of NF-kB/Rel proteins bind distinct kB sites to regulate the transcription of different genes. Early work involving NF-kB suggested its expression was limited to specific cell types, particularly in stimulating the transcription of genes encoding kappa immunoglobulins in B lymphocytes. However, it has been discovered that NF-kB is, in fact, present and inducible in many, if not all, cell types and that it acts as an intracellular messenger capable of playing a broad role in gene regulation as a mediator of inducible signal transduction. Specifically, it has been demonstrated that NF-kB plays a central role in regulation of intercellular signals in many cell types. For example, NF-kB has been shown to positively regulate the human beta-interferon (beta-IFN) gene in many, if not all, cell types. Moreover, NF-kB has also been shown to serve the important function of acting as an intracellular transducer of external influences.

The transcription factor NF-kB is sequestered in an inactive form in the cytoplasm as a complex with its inhibitor, IkB, the most prominent member of this class being IkBa. A number of factors are known to serve the role of stimulators of NF-kB activity, such as, for example, TNF. After TNF exposure, the inhibitor is phosphorylated and proteolytically removed, releasing NF-kB into the nucleus and allowing its transcriptional activity. Numerous genes are upregulated by this transcription factor, among them IkBa. The newly synthezised IkBa protein inhibits NF-kB, effectively shutting down further transcriptional activation of its downstream effectors. However, as mentioned above, the IkBa protein may only inhibit NF-kB in the absence of IkBa stimuli, such as TNF stimulation, for example. Other agents that are known to stimulate NF-kB release, and thus NF-kB activity, are bacterial lipopolysaccharide, extracellular polypeptides, chemical agents, such as phorbol esters, which stimulate intracellular phosphokinases, inflammatory cytokines, IL-1, oxidative and fluid mechanical stresses, and Ionizing Radiation (Basu, S., Rosenzweig, K, R., Youmell, M., Price, B, D, Biochem, Biophys, Res, Commun., 247(1):79-83, (1998)). Therefore, as a general rule, the stronger the insulting stimulus, the stronger the resulting NF-kB activation, and the higher the level of IkBa transcription. As a consequence, measuring the level of IkBa RNA can be used as a marker for antiapoptotic events, and indirectly, for the onset and strength of pro-apoptotic events.

The upregulation of IkBa due to the downregulation of HGPRBMY11 places this GPCR protein into a signalling pathway potentially involved in apoptotic events. This gives the opportunity to regulate downstream events via the activity of the protein HGPRBMY11 with antisense polynucleotides, polypeptides or low molecular chemicals with the potential of achieving a therapeutic effect in cancer, autoimmune diseases. In addition to cancer and immunological disorders, NF-kB has significant roles in other diseases (Baldwin, A. S., J. Clin Invest. 107, 3-6 (2001)). NF-kB is a key factor in the pathophysiology of ischemia-reperfusion injury and heart failure (Valen, G., Yan. Z Q, Hansson, G K, J. Am. Coll. Cardiol. 38, 307-14 (2001)).

Using the above examples, it is clear the availability of a novel cloned G-protein coupled receptor provides an opportunity for adjunct or replacement therapy, and are useful for the identification of G-protein coupled receptor agonists, or stimulators (which might stimulate and/or bias GPCR action), as well as, in the identification of G-protein coupled receptor inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of HGPRBMY11 polypeptides or peptides using recombinant techniques. Synthetic methods for producing the polypeptides and polynucleotides of the present invention are provided. Also provided are diagnostic methods for detecting diseases, disorders, and/or conditions related to the HGPRBMY11 polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the HGPRBMY11 protein having the amino acid sequence shown in FIGS. 1A-B (SEQ ID NO:2) or the amino acid sequence encoded by the cDNA clone, HGPRBMY11 (also referred to as GPCR74; and/or GPCR 81), deposited as ATCC Deposit Number PTA-2766 on Dec. 8, 2000.

The present invention also provides isolated nucleic acid molecules, that comprise, or alternatively consist of, a polynucleotide encoding the HGPRBMY11v1 protein having the amino acid sequence shown in FIGS. 6A-B (SEQ ID NO:30).

The present invention also provides isolated nucleic acid molecules, that comprise, or alternatively consist of, a polynucleotide encoding the HGPRBMY11v2 protein having the amino acid sequence shown in FIGS. 15A-B (SEQ ID NO:55).

All references to "HGPRBMY11" shall be construed to apply to HGPRBMY11, HGPRBMY11v1, and/or HGPRBMY11v2 unless otherwise specified herein.

The present invention also relates to recombinant vectors, which include the isolated nucleic acid molecules of the present invention, and to host cells containing the recombinant vectors, as well as to methods of making such vectors and host cells, in addition to their use in the production of HGPRBMY11, HGPRBMY11v1, and/or HGPRBMY11v2 polypeptides or peptides using recombinant techniques. Synthetic methods for producing the polypeptides and polynucleotides of the present invention are provided. Also provided are diagnostic methods for detecting diseases, disorders, and/or conditions related to the HGPRBMY11, HGPRBMY11v1, and/or HGPRBMY11v2 polypeptides and polynucleotides, and therapeutic methods for treating such diseases, disorders, and/or conditions. The invention further relates to screening methods for identifying binding partners of the polypeptides.

The invention further provides an isolated HGPRBMY11 polypeptide having an amino acid sequence encoded by a polynucleotide described herein.

The invention further provides an isolated HGPRBMY11v1 polypeptide having an amino acid sequence encoded by a polynucleotide described herein.

The invention further provides an isolated HGPRBMY11v2 polypeptide having an amino acid sequence encoded by a polynucleotide described herein.

The invention further relates to a polynucleotide encoding a polypeptide fragment of SEQ ID NO:2, 30, 55, or a polypeptide fragment encoded by the cDNA sequence included in the deposited clone, which is hybridizable to SEQ ID NO:1, 29, and/or 54.

The invention further relates to a polynucleotide encoding a polypeptide domain of SEQ ID NO:2, 30, and/or 55 or a polypeptide domain encoded by the cDNA sequence included in the deposited clone, which is hybridizable to SEQ ID NO:1, 29, and/or 54.

The invention further relates to a polynucleotide encoding a polypeptide epitope of SEQ ID NO:2, 30, and/or 55 or a polypeptide epitope encoded by the cDNA sequence included in the deposited clone, which is hybridizable to SEQ ID NO:1, 29, and/or 54.

The invention further relates to a polynucleotide encoding a polypeptide of SEQ ID NO:2, 30, and/or 55 or the cDNA sequence included in the deposited clone, which is hybridizable to SEQ ID NO:1, 29, and/or 54, having biological activity.

The invention further relates to a polynucleotide which is a variant of SEQ ID NO:1, 29, and/or 54.

The invention further relates to a polynucleotide which is an allelic variant of SEQ ID NO:1, 29, and/or 54.

The invention further relates to a polynucleotide which encodes a species homologue of the SEQ ID NO:2, 30, and/or 55.

The invention further relates to a polynucleotide which represents the complimentary sequence (antisense) of SEQ ID NO:1, 29, and/or 54.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, 30, 55, wherein the polynucleotide fragment comprises a nucleotide sequence encoding an immunoglobulin protein.

The invention further relates to an isolated nucleic acid molecule of SEQ ID NO:1, 29, and/or 54 wherein the polynucleotide fragment comprises a nucleotide sequence encoding the sequence identified as SEQ ID NO:2, 30, and/or 55 or the polypeptide encoded by the cDNA sequence included in the deposited clone, which is hybridizable to SEQ ID NO:1, 29, and/or 54.

The invention further relates to an isolated nucleic acid molecule of of SEQ ID NO:1, 29, and/or 54, wherein the polynucleotide fragment comprises the entire nucleotide sequence of SEQ ID NO:1, 29, and/or 54 or the cDNA sequence included in the deposited clone, which is hybridizable to SEQ ID NO:1, 29, and/or 54.

The invention further relates to an isolated nucleic acid molecule of SEQ ID NO:1, 29, and/or 54, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2, 30, and/or 55 or the encoded sequence included in the deposited clone.

The invention further relates to a polypeptide fragment of SEQ ID NO:2, 30, and/or 55 or the encoded sequence included in the deposited clone, having biological activity.

The invention further relates to a polypeptide domain of SEQ ID NO:2, 30, and/or 55 or the encoded sequence included in the deposited clone.

The invention further relates to a polypeptide epitope of SEQ ID NO:2, 30, and/or 55 or the encoded sequence included in the deposited clone.

The invention further relates to a full length protein of SEQ ID NO:2, 30, and/or 55 or the encoded sequence included in the deposited clone.

The invention further relates to a variant of SEQ ID NO:2, 30, and/or 55.

The invention further relates to an allelic variant of SEQ ID NO:2, 30, and/or 55. The invention further relates to a species homologue of SEQ ID NO:2, 30, and/or 55.

The invention further relates to the isolated polypeptide of of SEQ ID NO:2, 30, and/or 55, wherein the full length protein comprises sequential amino acid deletions from either the C-terminus or the N-terminus.

The invention further relates to an isolated antibody that binds specifically to the isolated polypeptide of SEQ ID NO:2, 30, and/or 55.

The invention further relates to a method for preventing, treating, or ameliorating a medical condition, comprising administering to a mammalian subject a therapeutically effective amount of the polypeptide of SEQ ID NO:2, 30, and/or 55 or the polynucleotide of SEQ ID NO:1, 29, and/or 54.

The invention further relates to a method of diagnosing a pathological condition or a susceptibility to a pathological condition in a subject comprising the steps of (a) determining the presence or absence of a mutation in the polynucleotide of SEQ ID NO:1, 29, and/or 54; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of of SEQ ID NO:2, 30, and/or 55 in a biological sample; and (b) diagnosing a pathological condition or a susceptibility to a pathological condition based on the presence or amount of expression of the polypeptide.

The invention further relates to a method for identifying a binding partner to the polypeptide of SEQ ID NO:2, 30, and/or 55 comprising the steps of (a) contacting the polypeptide of SEQ ID NO:2, 30, and/or 55 with a binding partner; and (b) determining whether the binding partner effects an activity of the polypeptide.

The invention further relates to a gene corresponding to the cDNA sequence of SEQ ID NO:1, 29, and/or 54.

The invention further relates to a method of identifying an activity in a biological assay, wherein the method comprises the steps of (a) expressing SEQ ID NO:1, 29, and/or 54 in a cell, (b) isolating the supernatant; (c) detecting an activity in a biological assay; and (d) identifying the protein in the supernatant having the activity.

The invention further relates to a process for making polynucleotide sequences encoding gene products having altered activity selected from the group consisting of SEQ ID NO:2, 30, and/or 55 activity comprising the steps of (a) shuffling a nucleotide sequence of SEQ ID NO:1, 29, and/or 54, (b) expressing the resulting shuffled nucleotide sequences and, (c) selecting for altered activity selected from the group consisting of SEQ ID NO:2, 30, and/or 55 activity as compared to the activity selected from the group consisting of SEQ ID NO:2, 30, and/or 55 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:2, 30, and/or 55 activity.

The invention further relates to a method for preventing, treating, or ameliorating a medical condition with the polypeptide provided as SEQ ID NO:2, 30, and/or 55, in addition to, its encoding nucleic acid, wherein the medical condition is an cardiovascular disorder The invention further relates to a method for preventing, treating, or ameliorating a medical condition with the polypeptide provided as SEQ ID NO:2, 30, and/or 55, in addition to, its encoding nucleic acid, wherein the medical condition is a inflammatory disorder.

The invention further relates to a method for preventing, treating, or ameliorating a medical condition with the polypeptide provided as SEQ ID NO:2, 30, and/or 55, in addition to, its encoding nucleic acid, wherein the medical condition is a an inflammatory disease where cysteinyl leukotrienes, either directly or indirectly, are involved in disease progression.

The invention further relates to a method for preventing, treating, or ameliorating a medical condition with the polypeptide provided as SEQ ID NO:2, 30, and/or 55, in addition to, its encoding nucleic acid, wherein the medical condition is a cancer.

The invention further relates to a method for preventing, treating, or ameliorating a medical condition with the polypeptide provided as SEQ ID NO:2, 30, and/or 55, in addition to, its encoding nucleic acid, wherein the medical condition is a vascular disorder.

The invention further relates to a method for preventing, treating, or ameliorating a medical condition with the polypeptide provided as SEQ ID NO:2, 30, and/or 55, in addition to, its encoding nucleic acid, wherein the medical condition is a pulmonary disorder.

The invention further relates to a method for preventing, treating, or ameliorating a medical condition with the polypeptide provided as SEQ ID NO:2, 30, and/or 55, in addition to, its encoding nucleic acid, wherein the medical condition is an immune disorder.

The invention further relates to a method for preventing, treating, or ameliorating a medical condition with the polypeptide provided as SEQ ID NO: 2, 30, and/or 55, in addition to, its encoding nucleic acid, or a modulator thereof, wherein the medical condition is ovarian cancer or related proliferative condition of the ovary; cervical cancer or related proliferative condition of the cervix; lung cancer or related proliferative condition of the lung; or melanoma or related proliferative condition of the skin.

The invention further relates to a method of diagnosing a pathological condition or a susceptibility to a pathological condition in a subject comprising the steps of (a) determining the presence or amount of expression of the polypeptide of of SEQ ID NO: 2, 30, and/or 55 in a biological sample; and (b) diagnosing a pathological condition or a susceptibility to a pathological condition based on the presence or amount of expression of the polypeptide relative to a control, wherein said condition is a member of the group consisting of: Crohn's disease or proliferative or inflammatory condition of the colon; ovarian cancer or related proliferative condition of the ovary; cervical cancer or related proliferative condition of the cervix; lung cancer or related proliferative condition of the lung; or melanoma or related proliferative condition of the skin.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of CRE response elements.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are HEK cells.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, and futher wherein said cells express the polypeptide at either low, moderate, or high levels.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, wherein said candidate compound is a small molecule, a peptide, or an antisense molecule.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, wherein said candidate compound is a small molecule, a peptide, or an antisense molecule, wherein said candidate compound is an agonist or antagonist.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements, wherein said candidate compound is a small molecule, a peptide, or an antisense molecule.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements, wherein said candidate compound is a small molecule, a peptide, or an antisense molecule, wherein said candidate compound is an agonist or antagonist.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are CHO cells that comprise a vector comprising the coding sequence of the beta lactamase gene under the control of NFAT response elements, wherein said cells further comprise a vector comprising the coding sequence of G alpha 15 under conditions wherein G alpha 15 is expressed, wherein said cells express beta lactamase at low, moderate, or high levels.

The invention further relates to a method of screening for candidate compounds capable of modulating the activity of a G-protein coupled receptor polypeptide, comprising: (i) contacting a test compound with a cell or tissue comprising an expression vector capable of expressing a polypeptide comprising an amino acid sequence as set forth in SEQ ID NO:2, 30, and/or 55, or encoded by ATCC deposit HGPRBMY11, under conditions in which said polypeptide is expressed; and (ii) selecting as candidate modulating compounds those test compounds that modulate activity of the G-protein coupled receptor polypeptide, wherein said cells are HEK cells wherein said cells comprise a vector comprising the coding sequence of the beta lactamase gene under the control of CRE response elements, wherein said cells express beta lactamase at low, moderate, or high levels.

The statement, "wherein said cells express beta lactamase at low, moderate, or high levels" is a reference to cells that either express beta lactamase at low, moderate, or high levels relative to the expression levels of a reference mRNA, gene, or protein; or a reference to the actual percentage of cells that express beta lactamase. In the latter example, high levels of expression would be achieved if the majority of cells were expressing beta lactamase, while low levels of expression would be achieved if only a subset of cells were expressing beta lactamase. Such cells may also express other proteins, such as the proteins of the present invention at low, moderate, or high levels as well.

BRIEF DESCRIPTION OF THE FIGURES/DRAWINGS

FIGS. 1A-B show the polynucleotide sequence (SEQ ID NO:1) and deduced amino acid sequence (SEQ ID NO:2) of the novel human G-protein coupled receptor, HGPRBMY11, of the present invention. The standard one-letter abbreviation for amino acids is used to illustrate the deduced amino acid sequence. The polynucleotide sequence contains a sequence of 1708 nucleotides (SEQ ID NO:1), encoding a polypeptide of 330 amino acids (SEQ ID NO:2). An analysis of the HGPRBMY11 polypeptide determined that it comprised the following features: seven transmembrane domains (TM1 to TM7) located from about amino acid 24 to about amino acid 48 (TM1; SEQ ID NO:12); from about amino acid 59 to about amino acid 83 (TM2; SEQ ID NO:13); from about amino acid 104 to about amino acid 125 (TM3; SEQ ID NO:14); from about amino acid 139 to about amino acid 158 (TM4; SEQ ID NO:15); from about amino acid 188 to about amino acid 206 (TM5; SEQ ID NO:16); from about amino acid 229 to about amino acid 250 (TM6; SEQ ID NO:17); and/or from about amino acid 270 to about amino acid 292 (TM7; SEQ ID NO:18) of SEQ ID NO:2 (FIGS. 1A-B) represented by double underlining; and six conserved cysteines located at amino acid 15, 95, 171, 204, 263, and/or 283 of SEQ ID NO:2 (FIGS. 1A-B) represented in bold. The seven transmembrane domains of the present invention are characteristic of G-protein coupled receptors as described more particularly elsewhere herein.

FIGS. 2A-B shows the regions of identity between the encoded HGPRBMY11 and HGPRBMY11v1 proteins (SEQ ID NO:2 and SEQ ID NO:30, respectively) to other G-protein coupled receptors, specifically, the chick purinergic receptor protein (P2YR_CHICK; Genbank Accession No:gi|P34996; SEQ ID NO:3), the turkey purinergic receptor protein, also known as, 6H1 orphan receptor (P2YR_MELGA; Genbank Accession No:gi|P49652; SEQ ID NO:4), the rat purinergic receptor (P2YR_RAT; Genbank Accession No:gi|P49651; SEQ ID NO:5), the human cysteinyl leukotriene receptor protein (Genbank Accession No.: gi|11422069; SEQ ID NO:6); the chick purinergic receptor 5 protein (P2Y5_CHICK; Genbank Accession No.: gi|P32250; SEQ ID NO:7); and the human G-protein-coupled receptor GPR17 (GPRH_HUMAN; Genbank Accession No. gi|Q13304; SEQ ID NO:8). The alignment was performed using the Pileup algorithm (Genetics Computer Group, Inc. suite of programs). The darkly shaded amino acids represent regions of matching identity. The lightly shaded amino acids represent regions of matching similarity. Lines between residues indicate gapped regions of non-identity for the aligned polypeptides. The conserved cysteines between HGPRBMY11, HGPRBMY11v1, and the other GPCRs are noted.

FIG. 3 shows a hydrophobicity plot of HGPRBMY11 according to the BioPlot Hydrophobicity algorithm of Vector NTI (version 5.5). The seven hydrophilic peaks are consistent with the HGPRBMY11 polypeptide being a G-protein coupled receptor.

Figure 4:
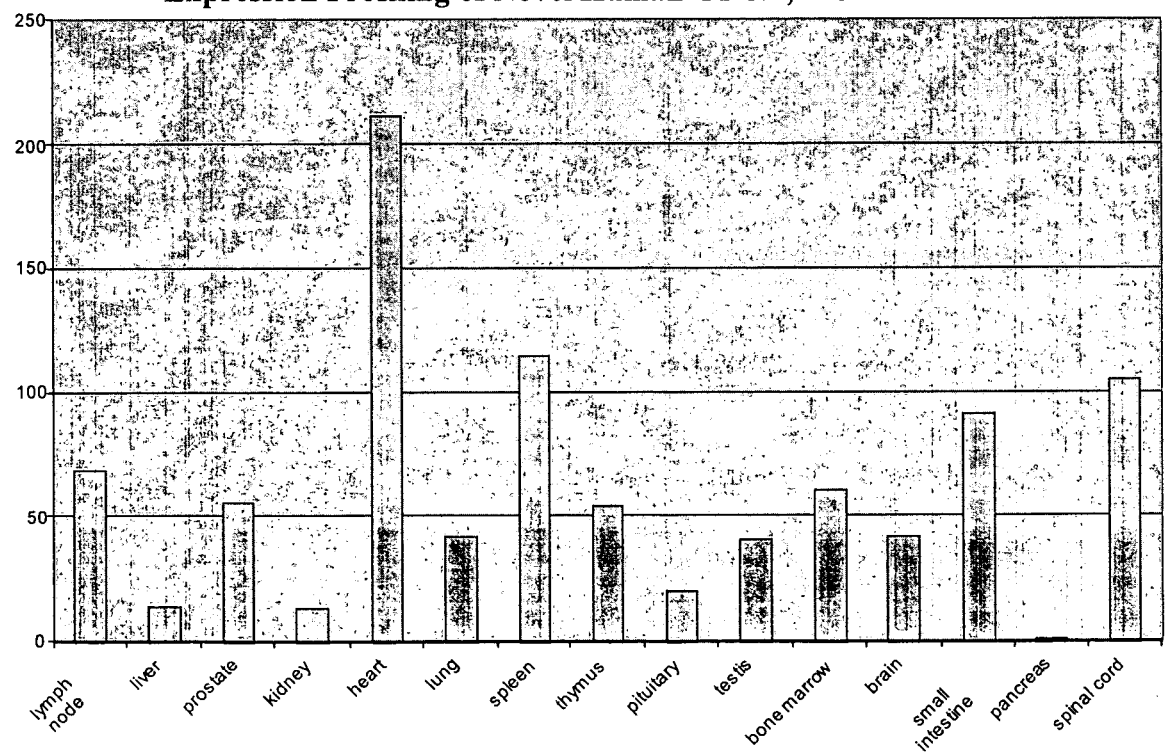

FIG. 4 shows an expression profile of the novel human G-protein coupled receptor, HGPRBMY11. The figure illustrates the relative expression level of HGPRBMY11 amongst various mRNA tissue sources. As shown, transcripts corresponding to HGPRBMY11 expressed highly in the heart. The HGPRBMY11 polypeptide was expressed to a significant extent, in the spleen, spinal cord, and small intestine, and to a lesser extent, in lymph node, bone marrow, thymus, prostate, lung, testis, and brain. Expression data was obtained by measuring the steady state HGPRBMY11 mRNA levels by quantitative PCR using the same PCR primer pair used to isolate the novel HGPRBMY11 cDNA clone (SEQ ID NO:10 and 11) as described herein.

FIG. 5 shows a table illustrating the percent identity and percent similarity between the HGPRBMY11 (SEQ ID NO:2) and HGPRVMY11v1 (SEQ ID NO:30) polypeptides of the present invention with other G-protein coupled receptors, specifically, the chick purinergic receptor protein (P2YR_CHICK; Genbank Accession No:gi|P34996; SEQ ID NO:3), the turkey purinergic receptor protein, also known as, 6H1 orphan receptor (P2YR_MELGA; Genbank Accession No:gi|P49652; SEQ ID NO:4), the rat purinergic receptor (P2YR_RAT; Genbank Accession No:gi|P49651; SEQ ID NO:5), the human cysteinyl leukotriene receptor protein (Genbank Accession No.: gi|11422069; SEQ ID NO:6); the chick purinergic receptor 5 protein (P2Y5_CHICK; Genbank Accession No.: gi|P32250; SEQ ID NO:7); and the human G-protein-coupled receptor GPR17 (GPRH_HUMAN; Genbank Accession No. gi|Q13304; SEQ ID NO:8). The percent identity and percent similarity values were determined using the Gap algorithm using default parameters (Genetics Computer Group suite of programs; Needleman and Wunsch. J. Mol. Biol. 48; 443-453, 1970)).

FIGS. 6A-B show the polynucleotide sequence (SEQ ID NO:29) and deduced amino acid sequence (SEQ ID NO:30) of the novel human G-protein coupled receptor variant, HGPRBMY11v1, of the present invention. The standard one-letter abbreviation for amino acids is used to illustrate the deduced amino acid sequence. The polynucleotide sequence contains a sequence of 1041 nucleotides (SEQ ID NO:29), encoding a polypeptide of 346 amino acids (SEQ ID NO:30). An analysis of the HGPRBMY11v1 polypeptide determined that it comprised the following features: seven transmembrane domains (TM1 to TM7) located from about amino acid 40 to about amino acid 64 (TM1; SEQ ID NO:31); from about amino acid 75 to about amino acid 99 (TM2; SEQ ID NO:32); from about amino acid 120 to about amino acid 141 (TM3; SEQ ID NO:33); from about amino acid 155 to about amino acid 173 (TM4; SEQ ID NO:34); from about amino acid 195 to about amino acid 222 (TM5; SEQ ID NO:35); from about amino acid 245 to about amino acid 266 (TM6; SEQ ID NO:36); and/or from about amino acid 286 to about amino acid 308 (TM7; SEQ ID NO:37) of SEQ ID NO:30 (FIGS. 6A-B) represented by double underlining; and six conserved cysteines located at amino acid 31, 111, 187, 220, 279, and/or 299 of SEQ ID NO:30 (FIGS. 6A-B) represented in bold. The seven transmembrane domains of the present invention are characteristic of G-protein coupled receptors as described more particularly elsewhere herein.

Figure 7:
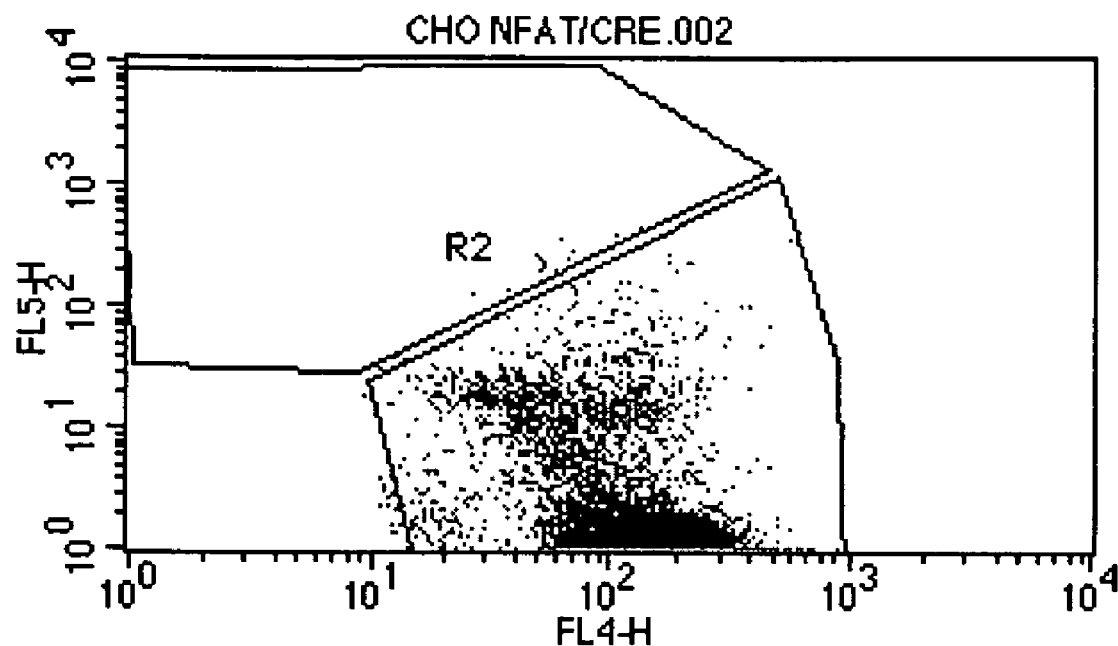

FIG. 7 shows the FACS profile of untransfected control Cho-NFAT/CRE (Nuclear Factor Activator of Transcription (NFAT)/cAMP response element (CRE)) cell lines, in the absence of the pcDNA3.1 Hygro™/HGPRBMY11 mammalian expression vector transfection, as described herein. The cells were analyzed via FACS (Fluorescent Assisted Cell Sorter) according to their wavelength emission at 518 nM (Channel R3—Green Cells), and 447 nM (Channel R2—Blue Cells). As shown, the vast majority of cells emit at 518 nM, with minimal emission observed at 447 nM. The latter is expected since the NFAT/CRE response elements remain dormant in the absence of an activated G-protein dependent signal transduction pathway (e.g., pathways mediated by Gq/11 or Gs coupled receptors). As a result, the cell permeant, CCF2/AM™ (Aurora Biosciences; Zlokarnik, et al., 1998) substrate remains intact and emits light at 518 nM.

Figure 8:
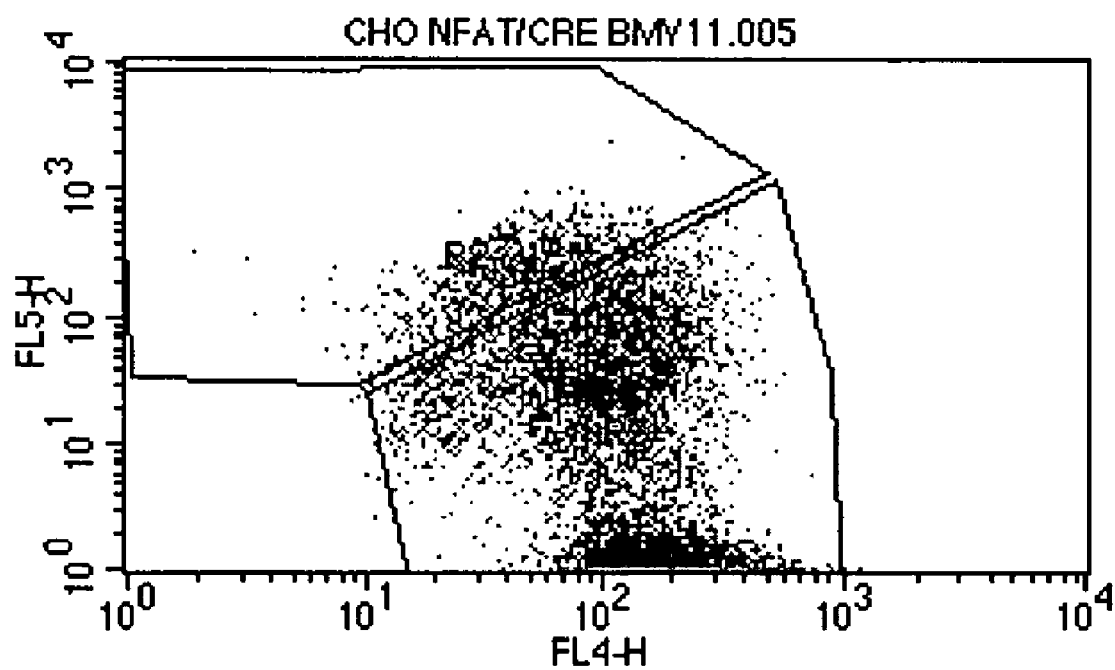

FIG. 8 shows the FACS profile observed upon overexpression of HGPRBMY11 which results in constitutive coupling through the NFAT/CRE response element in Cho-NFAT/CRE cell lines transfected with the pcDNA3.1 Hygro™/HG-PRBMY11 mammalian expression vector, as described herein. The cells were analyzed via FACS according to their wavelength emission at 518 nM (Channel R3—Green Cells), and 447 nM (Channel R2—Blue Cells). As shown, overexpression of HGPRBMY11 results in functional coupling and subsequent activation of beta lactamase gene expression, as evidenced by the significant number of cells with fluorescent emission at 447 nM relative to the non-transfected control Cho-NFAT/CRE cells (shown in FIG. 7).

Figure 9:
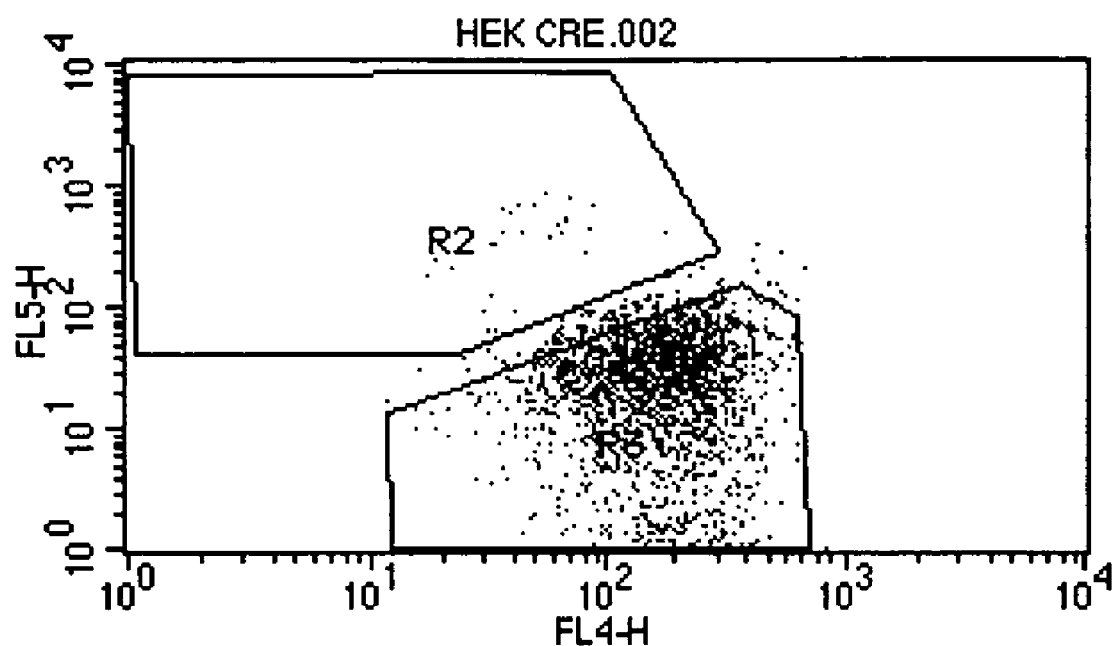

FIG. 9 shows the FACS profile of untransfected HEK-CRE cell lines containing the cAMP response element. HEK-CRE cell lines in the absence of the pcDNA3.1 Hygro™/HG-PRBMY11 mammalian expression vector transfection, as described herein. The cells were analyzed via FACS (Fluorescent Assisted Cell Sorter) according to their wavelength emission at 518 nM (Channel R3—Green Cells), and 447 nM (Channel R2-Blue Cells). As shown, the vast majority of cells emit at 518 nM, with minimal emission observed at 447 nM. The latter is expected since the CRE response elements remain dormant in the absence of an activated G-protein dependent signal transduction pathway (e.g., pathways mediated by Gs coupled receptors). As a result, the cell permeant, CCF2/AM™ (Aurora Biosciences; Zlokarnik, et al., 1998) substrate remains intact and emits light at 518 nM.

Figure 10:
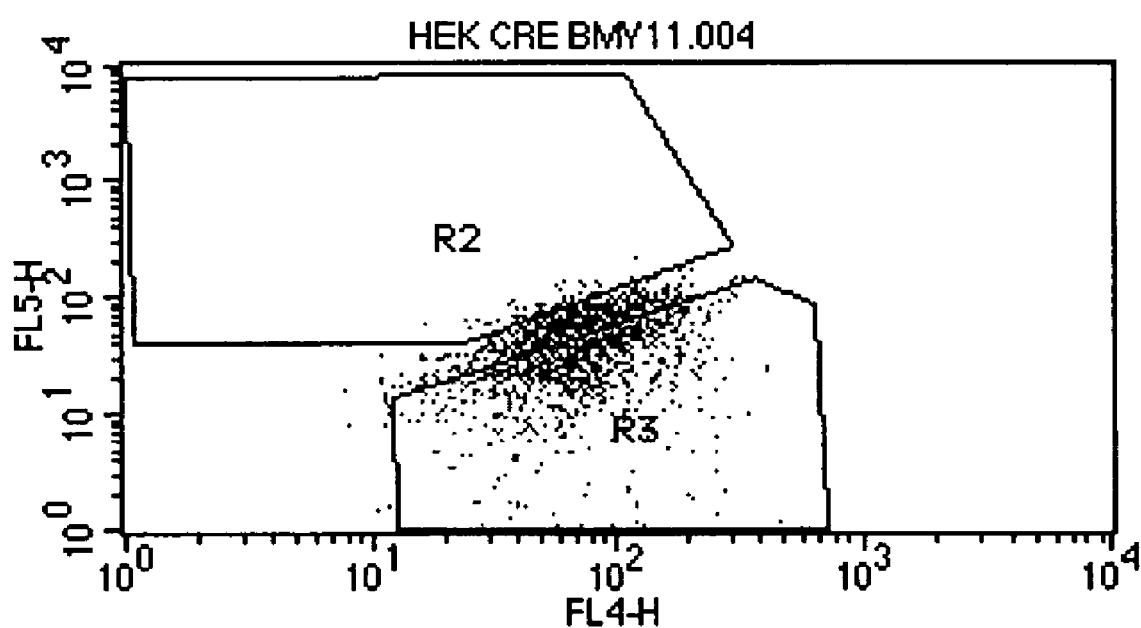

FIG. 10 shows HGPRBMY11 does not couple through the cAMP response element. HEK-CRE cell lines transfected with the pcDNA3.1 Hygro™/HGPRBMY11 mammalian expression vector were analyzed via FACS according to their wavelength emission at 518 nM (Channel R3—Green Cells), and 447 nM (Channel R2—Blue Cells). As shown, overexpression of HGPRBMY11 in the HEK-CRE cells did not result in functional coupling, as evidenced by the lack of significant change in fluorescent emission at 447 nM.

Figure 11:
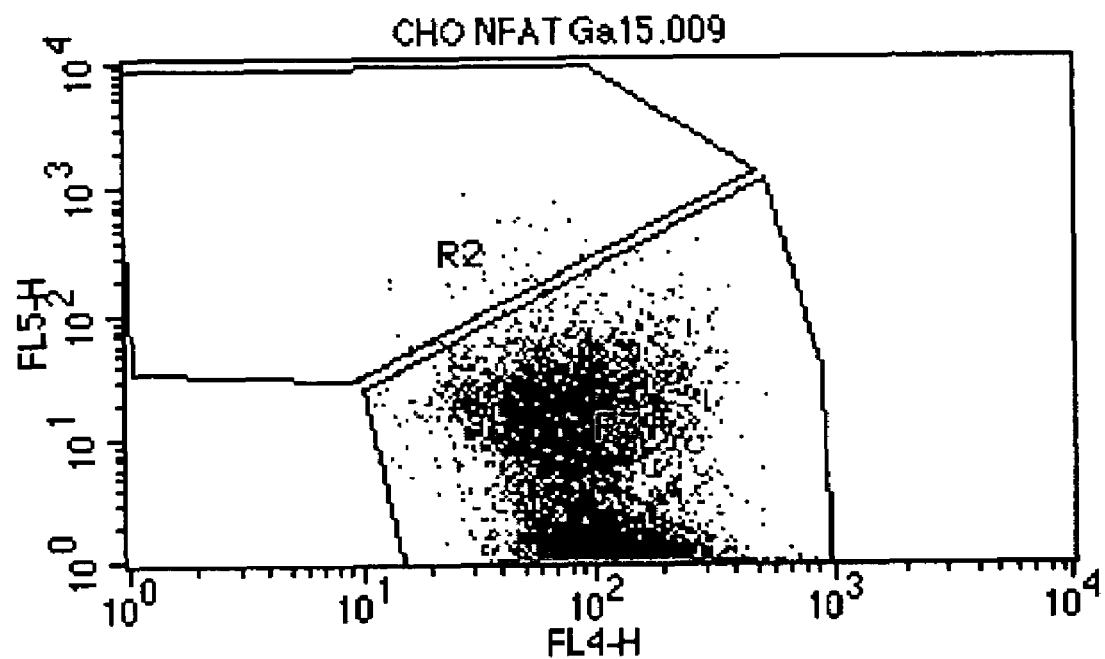

FIG. 11 shows the FACS profile of untransfected control Cho-NFAT G alpha 15 (Nuclear Factor Activator of Transcription (NFAT)) cell lines, in the absence of the pcDNA3.1 Hygro™/HGPRBMY11 mammalian expression vector transfection, as described herein. The cells were analyzed via FACS (Fluorescent Assisted Cell Sorter) according to their wavelength emission at 518 nM (Channel R3—Green Cells), and 447 nM (Channel R2—Blue Cells). As shown, the vast majority of cells emit at 518 nM, with minimal emission observed at 447 nM. The latter is expected since the NFAT response elements remain dormant in the absence of an activated G-protein dependent signal transduction pathway (e.g., pathways mediated by G alpha 15 Gq/11 or Gs coupled receptors). As a result, the cell permeant, CCF2/AM™ (Aurora Biosciences; Zlokarnik, et al., 1998) substrate remains intact and emits light at 518 nM.

Figure 12:
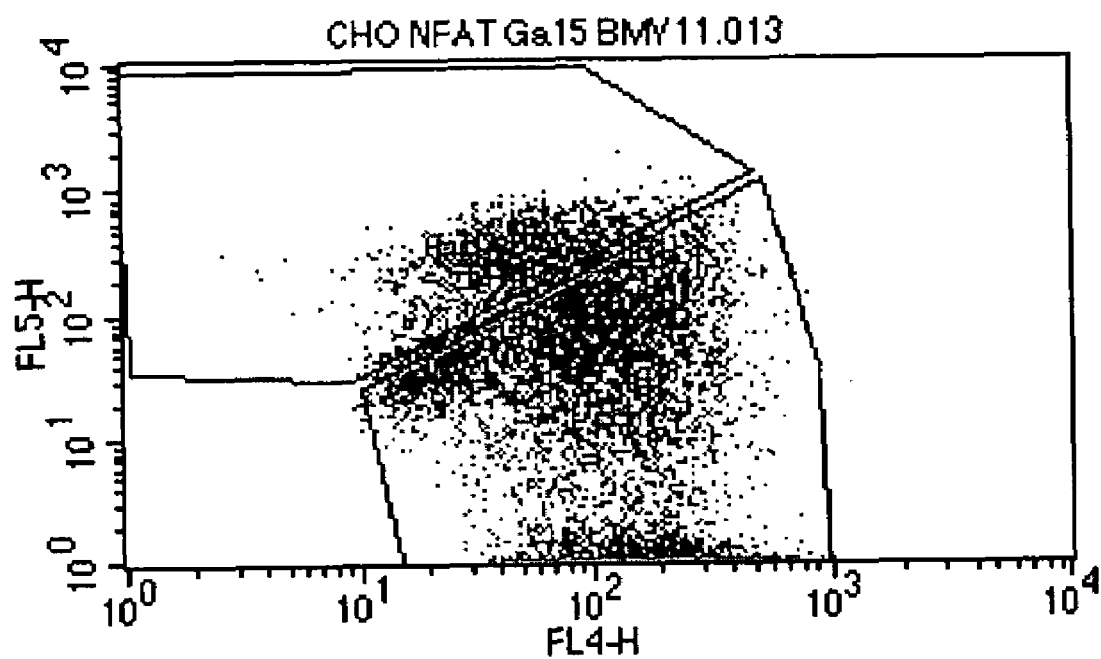

FIG. 12 shows overexpression of HGPRBMY11 in Cho-NFAT G alpha 15 cell lines results in constitutive coupling through the NFAT response element via the promiscuous G protein, Galpha 15. The cells were analyzed and sorted via FACS according to their wavelength emission at 518 nM (Channel R3—Green Cells), and 447 nM (Channel R2—Blue Cells). As shown, overexpression of HGPRBMY11 results in functional coupling and subsequent activation of beta lactamase gene expression, as evidenced by the significant number of cells with fluorescent emission at 447 nM relative to the non-transfected control Cho-NFAT G alpha 15 cells (shown in FIG. 11).

FIG. 13 shows expressed HGPRBMY11 polypeptide localizes to the cell membrane. Cho-NFAT G alpha 15 cell lines transfected with the pcDNA3.1 Hygro™/HG-PRBMY11-FLAG mammalian expression vector were subjected to immunocytochemistry using an FITC conjugated Anti Flag monoclonal antibody, as described herein. Panel A shows the transfected Cho-NFAT/CRE cells under visual wavelengths, and panel B shows the fluorescent emission of the same cells at 530 nm after illumination with a mercury light source. The cellular localization is clearly evident in panel B, and is consistent with the expression of HGPRBMY11.

FIG. 14 shows representative transfected Cho-NFAT/CRE cell lines with intermediate and high beta lactamase expression levels useful in screens to identify HGPRBMY11 agonists and/or antagonists. Several Cho-NFAT/CRE cell lines transfected with the pcDNA3.1 Hygro™/HGPRBMY11 mammalian expression vector were isolated via FACS that had either intermediate or high beta lactamase expression levels of constitutive activation, as described herein. Panel A shows untransfected Cho-NFAT/CRE cells prior to stimulation with 10 nM PMA and 1 uM Thapsigargin/10 uM Forskolin (−P/T/F). Panel B shows Cho-NFAT/CRE cells after stimulation with 10 nM PMA and 1 uM Thapsigargin/10 uM Forskolin (+P/T/F). Panel C shows a representative orphan GPCR (oGPCR) transfected Cho-NFAT/CRE cells that have an intermediate level of beta lactamase expression. Panel D shows a representative orphan GPCR transfected Cho-NFAT/CRE that have a high level of beta lactamase expression.

FIGS. 15A-B show the polynucleotide sequence (SEQ ID NO:54) and deduced amino acid sequence (SEQ ID NO:55) of the novel human G-protein coupled receptor variant, HGPRBMY11v2, of the present invention. The standard one-letter abbreviation for amino acids is used to illustrate the deduced amino acid sequence. The polynucleotide sequence contains a sequence of 1026 nucleotides (SEQ ID NO:54), encoding a polypeptide of 341 amino acids (SEQ ID NO:55).

Figure 16:
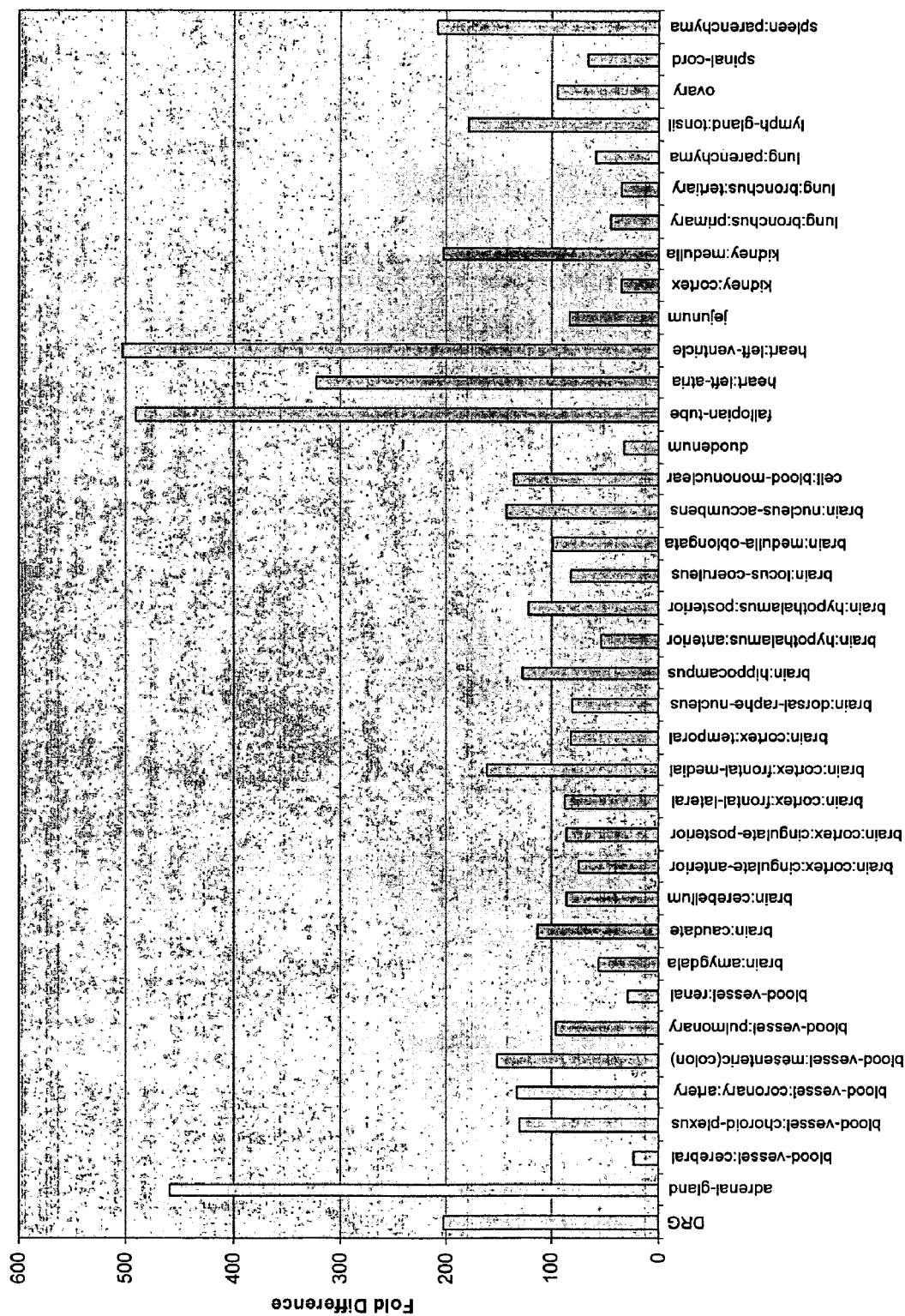

FIG. 16 shows an expanded expression profile of the novel human G-protein coupled receptor, HGPRBMY11. The figure illustrates the relative expression level of HGPRBMY11 amongst various mRNA tissue sources. As shown, the HGPRBMY11 polypeptide was expressed predominately in the lower gastrointestinal tract, specifically the ileum, the rectum, the colon, the jejunum, duodenum, with minor transcript levels observed in the stomach. Expression of HGPRBMY11 was also significantly expressed in the kidney, particularly in the cortex, followed by the medulla, and to a lesser extent in the testis. Expression data was obtained by measuring the steady state HGPRBMY11 mRNA levels by quantitative PCR using the PCR primer pair provided as SEQ ID NO:82 and 83, and Taqman probe (SEQ ID NO:84) as described in Example 5 herein.

Figure 17:
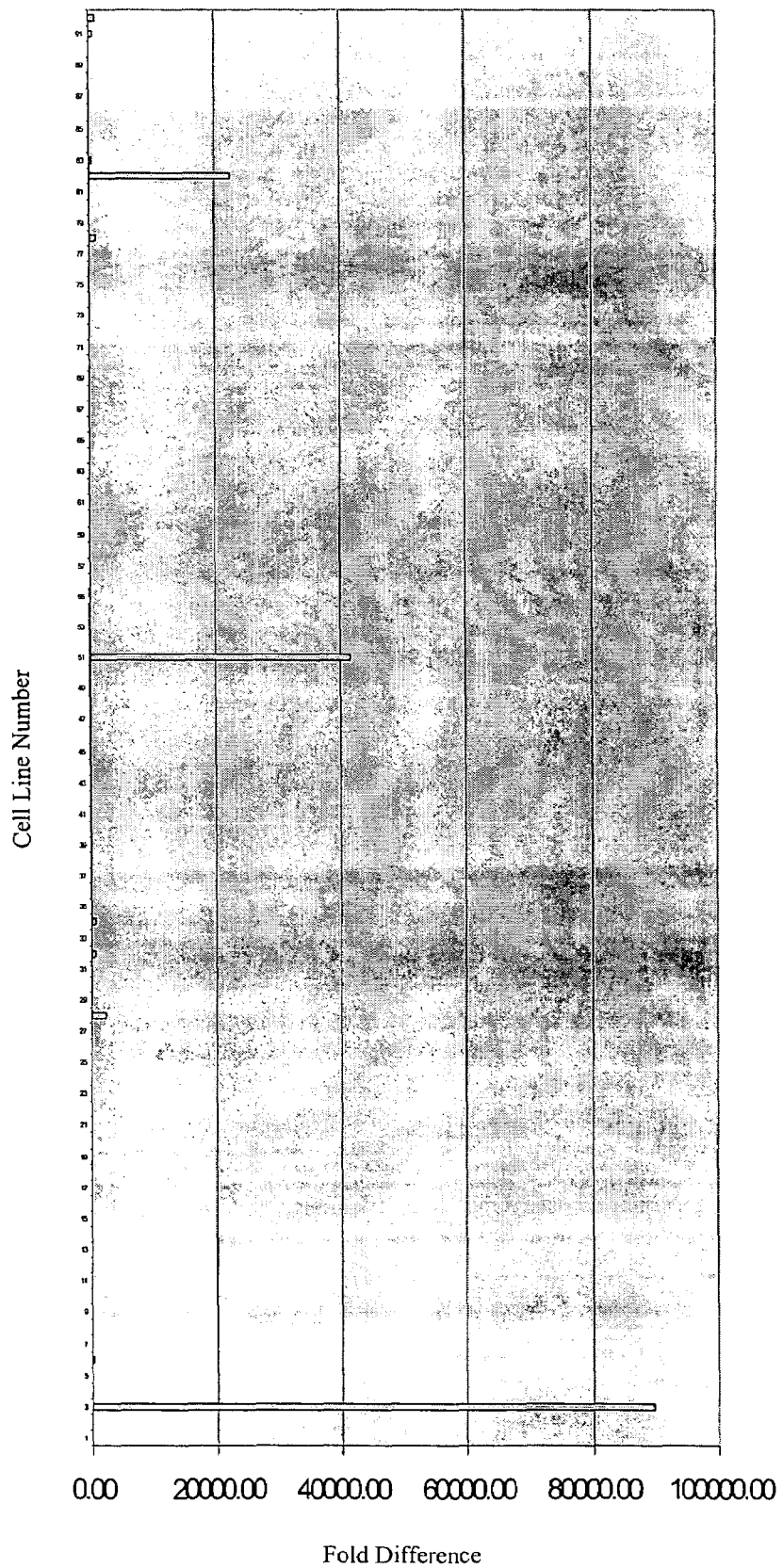

FIG. 17 shows an expanded expression profile of the novel human G-protein coupled receptor, HGPRBMY11, of the present invention. The figure illustrates the relative expression level of HGPRBMY11 amongst mRNA isolated from a number of cancer cell lines. As shown, the HGPRBMY11 polypeptide was expressed in ovarian cancer cell lines, significantly in a lung and melanoma cell lines, and to a lesser extent in other human tumor cell lines as shown. Expression data was obtained by measuring the steady state HGPRBMY11 mRNA levels by quantitative PCR using the PCR primer pair provided as SEQ ID NO:85 and 86 as described in Example 6 herein.

Figure 18:
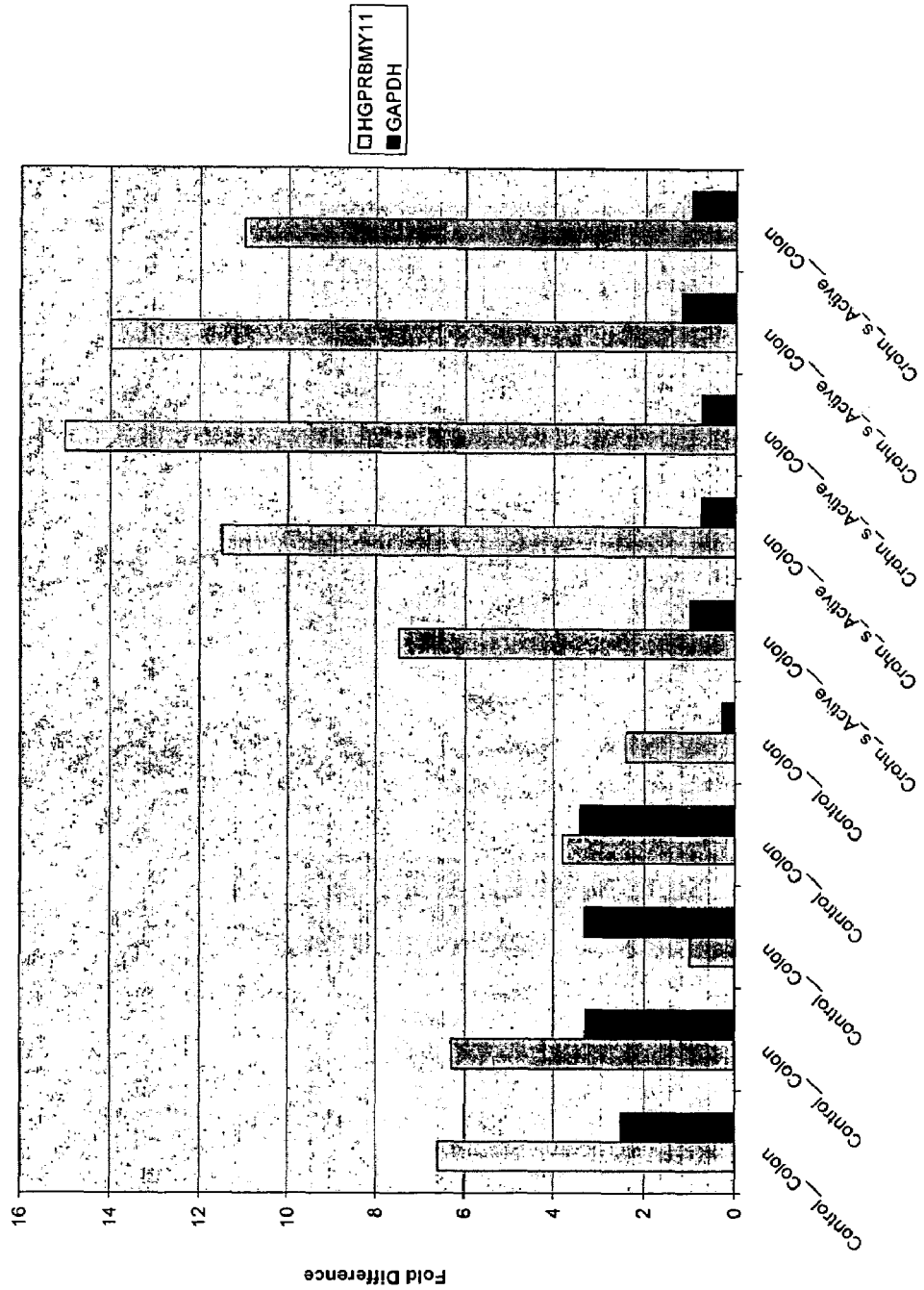

FIG. 18 shows an expanded expression profile of the novel human G-protein coupled receptor, HGPRBMY11, of the present invention. The figure illustrates the relative expression level of HGPRBMY11 amongst mRNA isolated from a both normal and disease tissues. As shown, the HGPRBMY11 polypeptide was differentially expressed in colon tissues isolated from patients exhibiting active Crohn's disease relative to normal colon tissues. The differential expression was statistically significant with a p value equal to 0.0024347, or more than 20 fold less than the art accepted statistically significant cutoff of 0.05. Expression data was obtained by measuring the steady state HGPRBMY11 mRNA levels by quantitative PCR using the PCR primer pair provided as SEQ ID NO:82 and 83, and Taqman probe (SEQ ID NO:84) as described in Example 5 herein.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

Table IV provides the results of expression profiling experiments on a series of cancer cell lines.

DETAILED DESCRIPTION OF THE INVENTION

The present invention may be understood more readily by reference to the following detailed description of the preferred embodiments of the invention and the Examples included herein. All references to "HGPRBMY11" shall be construed to apply to HGPRBMY11, HGPRBMY11v1, and/or HGPRBMY11v2 unless otherwise specified herein.

The invention provides a novel human sequence that encodes a G-protein coupled receptor (GPCR) with substantial homology to the class of GPCRs known as Cysteinyl Leukotriene receptors. Members of this class of G-protein coupled receptors have been implicated in a number of diseases and/or disorders, which include, but are not limited to, asthma, vascular disease, hypertension, bronchial hypersensitivity, rhinitis, etc. Expression analysis indicates the HGPRBMY11 has strong preferential expression in heart, and to a lesser extent, in spleen, spinal cord, and small intestine. Based on this information, we have provisionally named the gene and protein HGPRBMY11, for "Human G-Protein coupled Receptor BMY11". HGPRBMY11v1 was named as "Human G-Protein coupled Receptor HGPRBMY11 variant 1" accordingly. HGPRBMY11v1 was named as "Human G-Protein coupled Receptor HGPRBMY11 variant2" accordingly.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1, SEQ ID NO:29, SEQ ID NO:54 or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1 was often generated by overlapping sequences contained in one or more clones (contig analysis-specifically clone 9a and 9f). A representative clone containing all or most of the sequence for SEQ ID NO:1 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 plasmid (Life Technologies) using the NotI and SalI restriction endonuclease cleavage sites.

In the present invention, the full length HGPRBMY11 variant sequence identified as SEQ ID NO:29 was identified using bioinformatic methods as described more specifically herein.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-B (SEQ ID NO:1), a nucleic acid molecule of the present invention encoding the HGPRBMY11 polypeptide may be obtained using standard cloning and screening procedures, such as those for cloning cDNAs using mRNA as starting material. Illustrative of the invention, the nucleic acid molecule described in FIGS. 1A-B (SEQ ID NO:1) was discovered in a cDNA library derived from human liver, brain, and testis.

Using the information provided herein, such as the nucleotide sequence in FIGS. 6A-B (SEQ ID NO:29), a nucleic acid molecule of the present invention encoding the HGPRBMY11v1 polypeptide may be obtained using standard cloning and screening procedures, such as those for cloning cDNAs using mRNA as starting material.

Using the information provided herein, such as the nucleotide sequence in FIGS. 15A-B (SEQ ID NO:54), a nucleic acid molecule of the present invention encoding the HGPRBMY11v1 polypeptide may be obtained using standard cloning and screening procedures, such as those for cloning cDNAs using mRNA as starting material.

A "polynucleotide" of the present invention also includes those polynucleotides capable of hybridizing, under stringent hybridization conditions, to sequences contained in SEQ ID NO:1, SEQ ID NO:29, SEQ ID NO:54, the complements thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO: 1", "SEQ ID NO:29", and "SEQ ID NO:54" refer to polynucleotide sequences, while "SEQ ID NO:2", "SEQ ID NO:30", and "SEQ ID NO:55" refers to polypeptide sequences, all of these sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about ten-fold less activity, and most preferably, not more than about three-fold less activity relative to the polypeptide of the present invention).

As will be appreciated by the skilled practitioner, should the amino acid fragment comprise an antigenic epitope, for example, biological function per se need not be maintained. The terms HGPRBMY11 polypeptide and HGPRBMY11 protein are used interchangeably herein to refer to the encoded product of the HGPRBMY11 nucleic acid sequence according to the present invention.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

It is another aspect of the present invention to provide modulators of the HGPRBMY11 protein and HGPRBMY11 peptide targets which can affect the function or activity of HGPRBMY11 in a cell in which HGPRBMY11 function or activity is to be modulated or affected. In addition, modulators of HGPRBMY11 can affect downstream systems and molecules that are regulated by, or which interact with, HGPRBMY11 in the cell. Modulators of HGPRBMY11 include compounds, materials, agents, drugs, and the like, that antagonize, inhibit, reduce, block, suppress, diminish, decrease, or eliminate HGPRBMY11 function and/or activity. Such compounds, materials, agents, drugs and the like can be collectively termed "antagonists". Alternatively, modulators of HGPRBMY11 include compounds, materials, agents, drugs, and the like, that agonize, enhance, increase, augment, or amplify HGPRBMY11 function in a cell. Such compounds, materials, agents, drugs and the like can be collectively termed "agonists".

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321-9, (1995); and Ann. N.Y. Acad. Sci., 7; 766:279-81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

As used herein the terms "modulate or modulates" refer to an increase or decrease in the amount, quality or effect of a particular activity, DNA, RNA, or protein.

Polynucleotides and Polypeptides of the Invention
Features of the Polypeptide Encoded by Gene No: 1

The polypeptide of this gene provided as SEQ ID NO:2 (FIGS. 1A-B), encoded by the polynucleotide sequence according to SEQ ID NO:1 (FIGS. 1A-B), and/or encoded by the polynucleotide contained within the deposited clone, has significant homology at the nucleotide and amino acid level to a number of G-protein coupled receptors, which include, for example, the chick purinergic receptor protein (P2YR_CHICK; Genbank Accession No:gi|P34996; SEQ ID NO:3), the turkey purinergic receptor protein, also known as, 6H1 orphan receptor (P2YR_MELGA; Genbank Accession No:gi|P49652; SEQ ID NO:4), the rat purinergic receptor (P2YR_RAT; Genbank Accession No:gi|P49651; SEQ ID NO:5), the human cysteinyl leukotriene receptor protein (Genbank Accession No.: g|11422069; SEQ ID NO:6); the chick purinergic receptor 5 protein (P2Y5_CHICK; Genbank Accession No.:gi|P32250; SEQ ID NO:7); and the human G-protein-coupled receptor GPR17 (GPRH_HUMAN; Genbank Accession No. gi|Q13304; SEQ ID NO:8). An alignment of the HGPRBMY11 polypeptide with these proteins is provided in FIGS. 2A-B.

The determined nucleotide sequence of the HGPRBMY11 cDNA in FIGS. 1A-B (SEQ ID NO:1) contains an open reading frame encoding a protein of about 330 amino acid residues, with a deduced molecular weight of about 37.7 kDa. The amino acid sequence of the predicted HGPRBMY11 polypeptide is shown in FIGS. 1A-B (SEQ ID NO:2). The HGPRBMY11 protein shown in FIGS. 1A-B is about 30% identical and 45% similar to the chick purinergic receptor protein (P2YR_CHICK; Genbank Accession No:gi|P34996; SEQ ID NO:3); about 30% identical and 45% similar to the turkey purinergic receptor protein, also known as, 6H1 orphan receptor (P2YR_MELGA; Genbank Accession No:gi|P49652; SEQ ID NO:4); about 30% identical and 44% similar to the rat purinergic receptor (P2YR_RAT; Genbank Accession No:gi|P49651; SEQ ID NO:5); about 37% identical and 49% similar to the human cysteinyl leukotriene receptor protein (Genbank Accession No.: gi|1422069; SEQ ID NO:6); about 36% identical and 46% identical to the chick purinergic receptor 5 protein (P2Y5_CHICK; Genbank Accession No.: gi|P32250; SEQ ID NO:7); and about 36% identical and 46% similar to the human G-protein-coupled receptor GPR17 (GPRH_H MAN; Genbank Accession No. gi|Q13304; SEQ ID NO:8) as shown in FIG. 5.

The GPR17 protein is a G-protein coupled receptor that is predominately expressed in the brain and is believed to represent a chemokine receptor (J. Leukoc. Biol. 59 (1), 18-23 (1996)). As a result, the GPR17 protein may modulate the potent chemoattractant and activation activities for leukocytes. GPR17 was also found to be localized to chromosome band 2q21 which may suggest a potential disease association (J. Neurochem. 70 (4), 1357-1365 (1998)).

The chick P2YR protein receptor is a G-protein coupled receptor for extracellular adenine nucleotides such as ATP and ADP and seems to mediate its action via a pertussis toxin insensitive G-protein, probably belonging to the GQ family that activates a phosphatidylinositol-calcium second messenger system. The chick P2YR protein is expressed specifically in brain, spinal cord, gastrointestinal tract, spleen and leg muscle suggested a putative association of P2YR to disorders in these tissues. Expression of the chick P2YR (cRNA) in Xenopus oocytes resulted in a slowly-developing inward current was observed in response to application of ATP—which emphasized its identity as a P2Y receptor (FEBS Lett. 324 (2), 219-225 (1993)). The 3D structure of this receptor has been described (Drug Des Discov 13 (2), 133-154 (1995)). Based upon the conservation of critical residues within the HGPRBMY11 protein, it is likely that HGPRBMY11 shares similar structure, and potentially function to the chich P2YR receptor.

The HGPRBMY11 polypeptide was predicted to comprise 7 transmembrane domains using the TMPRED program (K Hofmann, W Stoffel, Biol. Chem., 347:166, 1993). The predicted transmembrane domains of the HGPRBMY11 polypeptide have been termed TM1 thru TM7 and are located from about amino acid 24 to about amino acid 48 (TM1; SEQ ID NO:12); from about amino acid 59 to about amino acid 83 (TM2; SEQ ID NO:13); from about amino acid 104 to about amino acid 125 (TM3; SEQ ID NO:14); from about amino acid 139 to about amino acid 158 (TM4; SEQ ID NO:15); from about amino acid 188 to about amino acid 206 (TM5; SEQ ID NO:16); from about amino acid 229 to about amino acid 250 (TM6; SEQ ID NO:17); and/or from about amino acid 270 to about amino acid 292 (TM7; SEQ ID NO:18) of SEQ ID NO:2 (FIGS. 1A-B). The predicted transmembrane domains aligned with the predicted transmembrane domains of related GPCRs at the sequence level (see FIG. 2). The seven transmembrane domains of the present invention are characteristic of G-protein coupled receptors as described more particularly elsewhere herein. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: FFPIVYLIIFFWGVLGNGLSIYVFL (SEQ ID NO:12), VFMLNLAISDLLFISTLPFRADYYL (SEQ ID NO:13), VNMYSSIYFLTVLSVVRFLAMV (SEQ ID NO:14), AWILCGIIWILIMASSIMLL (SEQ ID NO:15), IALVVGCLLPFFTLSICYL (SEQ ID NO:16), ALTTIIITLI-IFFLCFLPYHTL (SEQ ID NO:17), and/or ALVITLA-LAAANACFNPLLYYFA (SEQ ID NO:18). Polynucleotides encoding these polypeptides are also provided. The present invention also encompasses the use of the HGPRBMY11 transmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the HGPRBMY11 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., GPCR extracellular or intracellular loops) the HGPRBMY11 TM1 thru TM7 transmembrane domain polypeptides as antigenic and/or immunogenic epitopes.

In preferred embodiments, the present invention encompasses a polynucleotide lacking the initiating start codon, in addition to, the resulting encoded polypeptide of HGPRBMY11. Specifically, the present invention encompasses the polynucleotide corresponding to nucleotides 518 thru 1504 of SEQ ID NO:1, and the polypeptide corresponding to amino acids 2 thru 330 of SEQ ID NO:2. Also encompassed are recombinant vectors comprising said encoding sequence, and host cells comprising said vector.

The HGPRBMY11 polynucleotide (SEQ ID NO:1) was also determined to have an alternative initiating start codon just 5' of the indicated start codon (see FIGS. 1A-B). The encoded polypeptide of this alternative start codon is encompassed by the present invention (SEQ ID NO:55).

Specifically, in preferred embodiments, the following polypeptide is encompassed by the present invention and is referred to herein as HGPRBMY1 v2: MSLQPSISVSEME-PNGTFSNNNSRNCTIENFKREFF-PIVYLIIFFWGVLGNGLSIYVFLQ PYKKSTSVN-VFMLNLAISDLLFISTLPFRADYYLRGSNWIFGDLA CRIMSYSLYVNMY SSIYFLTVLSVVRFLAMVHPFR-LLHVTSIRSAWILCGIIWILIMASSIMLLDSGSEQNGS VTSCLELNLYKIAKLQTMNYIALVVG-CLLPFFTLSICYLLIIRVLLKVEVPESGLRVSH RKALT-TIIITLIIFFLCFLPYHTLRTVHLT-TWKVGLCKDRLHKALVITLALAAANACFN PLLYYFAGENFKDRLKSALRKGHPQKAK-TKCVFPVSVWLRKETRV (SEQ ID NO: 55). Polynucleotide sequences encoding this polypeptide are also provided: ATGTCCTTGCAACCATCCATCTCCGTAT-CAGAAATGGAACCAAATGGCACCTTCA GCAATAA-CAACAGCAGGAACTGCACAAT-TGAAAACTTCAAGAGAGAATTTTCC CAATTGTATATCT-GATAATATTTTTCTGGGGAGTCTTGG-GAAATGGGTTGTCCAT ATATGTTTTCCTGCAGCCT- TATAAGAAGTCCACATCTGTGAACGTTTTCATGCTAA
ATCTGGCCATTTCAGATCTCCTGTTCAT-
AAGCACGCTTCCCTTCAGGGCTGACTAT TATCTTA-
GAGGCTCCAATTGGATATTTGGAGAC-
CTGGCCTGCAGGATTATGTCTT
ATTCCTTGTATGTCAACATGTACAGCAG-
TATTTATTTCCTGACCGTGCTGAGTGTT
GTGCGTTTCCTGGCAATGGTTCAC-
CCCTTTCGGCTTCTGCATGTCACCAGCATCAG
GAGTGCCTGGATCCTCTGTGGGAT-
CATATGGATCCTTATCATGGCTTCCTCAATA
ATGCTCCTGGACAGTGGCTCTGAGCA-
GAACGGCAGTGTCACATCATGCTTAGAGC
TGAATCTCTATAAAATTGCTAAGCTGCA-
GACCATGAACTATATTGCCTTGGTGGT GGGCTGC-
CTGCTGCCATTTTTCACACTCAGCATCT-
GTTATCTGCTGATCATTCGGG
TTCTGTTAAAAGTGGAGGTCCCA-
GAATCGGGCTGCGGGTTTCTCACAGGAAGG
CACTGACCACCATCATCATCACCTTGAT-
CATCTTCTTCTTGTGTTTCCTGCCCTAT CACACACT-
GAGGACCGTCCACTTGACGACATG-
GAAAGTGGGTTTATGCAAAGAC
AGACTGCATAAAGCTTTGGTTATCA-
CACTGGCCTTGGCAGCAGCCAATGCCTGCT
TCAATCCTCTGCTCTAT-
TACTTTGCTGGGGAGAATTTTAAGGACA-
GACTAAAGTC TGCACTCAGAAAAGGCCATCCACA-
GAAGGCAAAGACAAAGTGTGTTTTCCCTGT
TAGTGTGTGGTTGAGAAAGGAAACAAGAGTATAA
(SEQ ID NO:54). The present invention also encompasses the use of this HGPRBMY11v2 polypeptide as an immunogenic and/or antigenic epitope as described elsewhere herein.

In preferred embodiments, the present invention encompasses a polynucleotide lacking the initiating start codon, in addition to, the resulting encoded polypeptide of HGPRBMY11v2. Specifically, the present invention encompasses the polynucleotide corresponding to nucleotides 4 thru 1023 of SEQ ID NO:53, and the polypeptide corresponding to amino acids 2 thru 341 of SEQ ID NO:54. Also encompassed are recombinant vectors comprising said encoding sequence, and host cells comprising said vector.

Also preferred are the encoding polynucleotides of HGPRBMY11 containing the stop codon at the 3' end of the coding sequence, specifically nucleotides 515 to 1507 of SEQ ID NO:1 are encompassed by the present invention.

Assays designed to determine whether the HGPRBMY11 polypeptide (SEQ ID NO:2) is capable of physiological coupling have shown that HGPRBMY11 does couple (see Example 4). Moreover, the results also indicated that HGPRBMY11 constitutively activates gene expression through the NFAT/CRE response element. This finding is significant as other versions of the HGPRBMY11 polypeptide have been described herein (e.g., HGPRBMY11v1), and/or in the art that have a longer N-terminus. The results described herein demonstrate that the additional N-terminal amino acid residues of HGPRBMY11 are not required for functional HGPRBMY11 coupling.

Based upon the strong homology to members of the G-protein coupled receptor proteins, the HGPRBMY11 polypeptide is expected to share at least some biological activity with G-protein coupled receptors, and preferably with purinergic receptor GPCR members, and more preferably with cysteinal leukotriene GPCR family members.

Expression profiling designed to measure the steady state mRNA levels encoding the HGPRBMY11 polypeptide showed predominately high expression levels in heart tissue, significant expression levels in spleen, spinal cord, and small intestine, and to a lesser extent, in lymph node, thymus, bone marrow, and prostate tissue (See FIG. 4).

Expanded analysis of HGPRBMY11 expression levels by TaqMan™ quantitative PCR (see FIG. 16) confirmed that the HGPRBMY11 polypeptide is expressed in heart, and spleen (FIG. 4). HGPRBMY11 mRNA was expressed predominately in the heart (approximately 500 fold compared to the lowest tissue observed, muscle. HGPRBMY11 was also expressed at high levels in the fallopian tube and the adrenal gland. Appreciable expression was observed in the parenchyma cells of the spleen and the medulla of the kidney. Expression is also observed across all the brain sub regions analyzed. Collectively, the expanded expression data provides additional evidence that HGPRBMY11, and modulators thereof, is useful for treating cardiovascular disorders, in addition to disorders of the female reproductive tract, including carcinomas and infertility as well as those of the adrenal gland, including Addison's disease, secondary adrenal insufficiency, adrenal cortical hyperfunction, adrenal virilism, Cushing's syndrome, hyperaldosteronism, pheochromcytoma and various multiple endocrine neoplasia syndromes.

Importantly, HGPRBMY11 was found to be differentially expressed in colon tissue isolated from patients with active Crohn's disease relative to normal colon tissue (see FIG. 18). The differentially expression was statistically significant with a p value equal to 0.0024347, or more than 20 fold less than the art accepted statistically significant cutoff of 0.05. These results umabiguously establish that HGPRBMY11 polynucleotides and polypeptides, including its splice variants HGPRBMY11v1 and HGPRBMY11v2, are useful in diagnosing patients to detect the incidence of Crohn's disease, or a patients suspectibility of acquiring Crohn's disease. Moreover, antagosists of HGPRBMY11, and/or its variants HGPRBMY11v1 and HGPRBMY11v2, may be useful in the treatment of Crohn's disease.

The association of HGPRBMY11 to the incidence of Crohn's disease is consistent with its association to NFkB (see below) and inflammatory pathways, in general.

Additional expression profiling analysis of HGPRBMY11 expression levels in various cancer cell lines by SYBR green real-time-PCR (see FIG. 17) determined that HGPRBMY11 is expressed in ovarian and cervical cancer cell lines, significantly in a lung and melanoma cell lines, and to a lesser extent in other human tumor cell lines as shown. The data suggests the HGPRBMY11 polypeptide may play a critical role in the development of a transformed phenotype leading to the development of cancers and/or a proliferative condition, either directly or indirectly. Alternatively, the HGPRBMY11 polypeptide may play a protective role and could be activated in response to a cancerous or proliferative phenotype. Whether HGPRBMY11 plays a role in directing transformation, or plays the role of protecting cells in response to a transformed phenotype, its role in ovarian, cervical, lung, and/or melanoma tumors is likely to be enhanced relative to normal tissues. Therefore, antagonists or agonists of the HGPRBMY11 polypeptide may be useful in the treatment, amelioration, and/or prevention of a variety of proliferative conditions, including, but not limited to ovarian tumors, in addition to cervical, lung, and/or melanoma tumors or proliferative conditions.

These data suggests that HGPRBMY11 is involvement in diseases of the female reproductive tract, especially but not limited to cancers and proliferative conditions. Modulators of HGPRBMY11 activity may have utility in the treatment of such disorders. There was also very high expression in a cell line from lung origin (DMS 114 line) and a cell line from melanoma origin (SK-MEL 5). Expression in the DMS 114 line was over 29,000 fold higher than the lowest tissue, and expression in the SK-MEL-5 line was over 16,000 fold higher than the lowest tissue. These observations raise the possiblilty that this GPCR is involved in disease processes in other tissues as well, particularly cervical, lung, and melanoma, especially, but not limited to cancers.

Additional evidence that HGPRBMY11 plays a role in proliferative disorders has been elucidated using antisense oligonucleotides which led to the determination that HGPRBMY11 is involved in modulation of the NFkB pathway through the negative modulation of the IkB modulatory protein as described in Example 7 herein.

In preferred embodiments, HGPRBMY11 polynucleotides and polypeptides, including modulators and fragments thereof, are useful for treating, diagnosing, and/or ameliorating proliferative disorders, cancers, ischemia-reperfusion injury, heart failure, immuno compromised conditions, HIV infection, and renal diseases.

Moreover, HGPRBMY11 polynucleotides and polypeptides, including modulators and fragments thereof, are useful for decreasing NF-kB activity, increasing apoptotic events, and/or increasing IκBα expression or activity levels.

In preferred embodiments, antagonists directed against HGPRBMY11 are useful for treating, diagnosing, and/or ameliorating autoimmune disorders, disorders related to hyper immune activity, inflammatory conditions, disorders related to aberrant acute phase responses, hypercongenital conditions, birth defects, necrotic lesions, wounds, organ transplant rejection, conditions related to organ transplant rejection, disorders related to aberrant signal transduction, proliferating disorders, cancers, HIV, and HIV propagation in cells infected with other viruses.

Moreover, antagonists directed against HGPRBMY11 are useful for decreasing NF-kB activity, increasing apoptotic events, and/or increasing IκBα expression or activity levels.

In preferred embodiments, agonists directed against HGPRBMY11 are useful for treating, diagnosing, and/or ameliorating autoimmune diorders, disorders related to hyper immune activity, hypercongenital conditions, birth defects, necrotic lesions, wounds, disorders related to aberrant signal transduction, immuno compromised conditions, HIV infection, proliferating disorders, and/or cancers.

Moreover, agonists directed against HGPRBMY11 are useful for increasing NF-kB activity, decreasing apoptotic events, and/or decreasing IκBα expression or activity levels.

The HGPRBMY11 polynucleotides and polypeptides of the present invention, including agonists and/or fragments thereof, have uses that include detecting, prognosing, treating, preventing, and/or ameliorating the following diseases and/or disorders, Alzheimer's, Parkinson's, diabetes, dwarfism, color blindness, retinal pigmentosa and asthma, depression, schizophrenia, sleeplessness, hypertension, anxiety, stress, renal failure, acute heart failure, hypotension, hypertension, endocrinal diseases, growth disorders, neuropathic pain, obesity, anorexia, HIV infections, cancers, bulimia, asthma, Parkinson's disease, osteoporosis, angina pectoris, myocardial infarction, psychotic, immune, metabolic, cardiovascular, and neurological disorders The HGPRBMY11 polynucleotides and polypeptides of the present invention, including agonists and/or fragments thereof, have uses that include modulating signal transduction activity, in various cells, tissues, and organisms, and particularly in mammalian heart, spleen, spinal cord, and small intestine tissue, preferably human tissue.

HGPRBMY11 polynucleotides and polypeptides of the present invention, including agonists and/or fragments thereof, may be useful in diagnosing, treating, prognosing, and/or preventing cardiovascular, metabolic, neurological, immune, and/or proliferative diseases or disorders.

The strong homology to human G-protein coupled receptors, combined with the predominate localized expression in heart tissue suggests the HGPRBMY11 polynucleotides and polypeptides may be useful in treating, diagnosing, prognosing, and/or preventing cardiovascular diseases and/or disorders, which include, but are not limited to: myocardio infarction, congestive heart failure, arrthymias, cardiomyopathy, atherosclerosis, arterialsclerosis, microvascular disease, embolism, thrombosis, pulmonary edema, palpitation, dyspnea, angina, hypotension, syncope, heart murmer, aberrant ECG, hypertrophic cardiomyopathy, the Marfan syndrome, sudden death, prolonged QT syndrome, congenital defects, cardiac viral infections, valvular heart disease, and hypertension.

Similarly, HGPRBMY11 polynucleotides and polypeptides may be useful for ameliorating cardiovascular diseases and symptoms which result indirectly from various non-cardiavascular effects, which include, but are not limited to, the following, obesity, smoking, Down syndrome (associated with endocardial cushion defect); bony abnormalities of the upper extremities (associated with atrial septal defect in the Holt-Oram syndrome); muscular dystrophies (associated with cardiomyopathy); hemochromatosis and glycogen storage disease (associated with myocardial infiltration and restrictive cardiomyopathy); congenital deafness (associated with prolonged QT interval and serious cardiac arrhythmias); Raynaud's disease (associated with primary pulmonary hypertension and coronary vasospasm); connective tissue disorders, i.e., the Marfan syndrome, Ehlers-Danlos and Hurler syndromes, and related disorders of mucopolysaccharide metabolism (aortic dilatation, prolapsed mitral valve, a variety of arterial abnormalities); acromegaly (hypertension, accelerated coronary atherosclerosis, conduction defects, cardiomyopathy); hyperthyroidism (heart failure, atrial fibrillation); hypothyroidism (pericardial effusion, coronary artery disease); rheumatoid arthritis (pericarditis, aortic valve disease); scleroderma (cor pulmonale, myocardial fibrosis, pericarditis); systemic lupus erythematosus (valvulitis, myocarditis, pericarditis); sarcoidosis (arrhythmias, cardiomyopathy); postmenopausal effects, Chlamydial infections, polycystic ovary disease, thyroid disease, alcoholism, diet, and exfoliative dermatitis (high-output heart failure), for example.

Alternatively, the strong homology to human G-protein coupled receptors, combined with the significant localized expression in various immune tissues, particularly spleen, thymus, lymph node, and bone marrow suggests the HGPRBMY11 polynucleotides and polypeptides may be useful in treating, diagnosing, prognosing, and/or preventing immune diseases and/or disorders. Representative uses are described in the "Immune Activity" and "Infectious Disease" sections below, and elsewhere herein. Briefly, the strong expression in immune tissue indicates a role in regulating the proliferation; survival; differentiation; and/or activation of hematopoietic cell lineages, including blood stem cells. Such roles for G-protein coupled receptors have been described. For example, the involvment of G-protein coupled receptorsin immune modulation have been determined experimentally, through the use of G-protein coupled receptor antagonists—namely cannabinoids, such as delta 9-tetrahydrocannabinol (delta 9-THC) as described by Kaminski, N. E., et al., Biochem-Pharmacol., 48(10):1899-908 (1994), and Schatz-A. R., et al., Life-Sci.; 51(6):PL25-30

(1992). Based upon these results, the authors were able to implicate a G-protein coupled receptor in modulating lymphocyte activation.

The HGPRBMY11 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may modulate the expression, either directly or indirectly, of a secreted factor that influences the differentiation or behavior of other blood cells, or that recruits hematopoietic cells to sites of injury. Thus, this gene product may be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

In addition, the strong homology to G-protein coupled receptors, combined with the expression in small intestine tissue suggests a potential utility for HGPRBMY11 polynucleotides and polypeptides in treating, diagnosing, prognosing, and/or preventing gastrointestinal disorders, such as, for example, ulcers, cancers, etc., in addition to those disorders related to aberrant function of immune cells or tissue within the small intestine (e.g., Peyer's patches, etc.).

Moreover, HGPRBMY11 polynucleotides and polypeptides, including fragments and agonists thereof, may have uses which include treating, diagnosing, prognosing, and/or preventing hyperproliferative disorders, particularly of the cardiovascular, immune, and gastrointestinal systems. Such disorders may include, for example, cancers, and metastasis.

As the polypeptide of the present invention may be involved in the regulation of cytokine production, antigen presentation, T-cell maturation, or other processes, either directly or indirectly, suggests the HGPRBMY11 polypeptide may be useful for the treatment of cancer (e.g. by boosting immune responses).

The HGPRBMY11 polynucleotides and polypeptides, including fragments and/or modulators thereof, may have uses which include identification of modulators of HGPRBMY11 function including antibodies (for detection or neutralization), naturally-occurring modulators and small molecule modulators. Antibodies to domains of the HGPRBMY11 protein could be used as diagnostic agents of cardiovascular and inflammatory conditions in patients, are useful in monitoring the activation of signal transduction pathways, and can be used as a biomarker for the involvement of G-protein couplded receptors in disease states, and in the evaluation of inhibitors of G-protein coupled receptors in vivo.

HGPRBMY11 polypeptides and polynucleotides have additional uses which include diagnosing diseases related to the over and/or under expression of HGPRBMY11 by identifying mutations in the HGPRBMY11 gene by using HGPRBMY11 sequences as probes or by determining HGPRBMY11 protein or mRNA expression levels. HGPRBMY11 polypeptides may be useful for screening compounds that affect the activity of the protein. HGPRBMY11 peptides can also be used for the generation of specific antibodies and as bait in yeast two hybrid screens to find proteins the specifically interact with HGPRBMY11 (described elsewhere herein).

As described elsewhere herein, the HGPRBMY11 polypeptide shares significant homology to human cysteinyl leukotriene receptors. Therefore, HGPRBMY11 polypeptides are expected to share at least some biological activity with cysteinyl leukotriene receptors. Cysteinyl leukotrienes (CysLTs), slow-reacting substances of anaphylaxis, are lipid mediators known to possess potent proinflammatory action. Pharmacological studies using CysLTs have shown that at least two classes of G protein-coupled receptors (GPCRs), named CysLT(1) and CysLT(2), exist; the former is sensitive and the latter is resistant to the CysLT(1) antagonists currently used to treat asthma. Despite the fact that a member of the CysLT(1) receptor group has been cloned, the molecular identity of members of the CysLT(2) group appear to be elusive.

Significant clinical data have directly implicated CysLTs to the increased incidence of asthma (Blain, J. F., Prostaglandins Leukot. Essent. Fatty. Acids., 62(6):361-8 (2000)), in addition to, the pathogenesis of aspirin-intolerant asthma (AIA) (Ishioka, S., et al., Hiroshima J. Med. Sci., 49(2):105-8 (2000)). The latter is consistent with the observed expression of HGPRBMY11 in diseased lung tissues.

A number of studies have shown CysLT receptor antagonists to have significant clinical efficacy in ameliorating diseases and symptoms associated with cysteinyl leukotrienes through therapeutic antileukotriene effects. Due to these effects, antileukotriene drugs have recently been approved for the treatment of asthma. Such CysLT receptor anatagonists include, the following, non-limiting examples: MK-571, pranlukast, montelukast (Jarvis, B., et al., Drugs., 59(4):891-928 (2000)).

In preferred embodiments, HGPRBMY11 polypeptide antagonists, including fragments thereof, may have uses which include modulating eosinophilic populations (e.g. increase or decrease), either directly or indirectly, in addition to, treating, prognosing, preventing, and/or ameliorating asthma, in addition to aspirin-intolerant asthma, and other disorders related to cysteinal leukotriene-dependent activation.

In addition, such CysLT receptor anatagonists have also been shown to exhibit antieosinophilic effects, further implicating a role for CysLT receptors in immune modulation (Yoshida, S., et al., Clin. Exp. Allergy., 30(7):1008-14 (2000); Lee, E., et al., Am J. Respir. Crit. Care. Med., 161(6):1881-6 (2000)). The latter is consistent with the observed expression of HGPRBMY11 in immune tissues, in addition to its association with the NFkB pathway.

In preferred embodiments, HGPRBMY11 polypeptide antagonists, including fragments thereof, may have uses which include treating, prognosing, preventing, and/or ameliorating immune disorders, particularly hypersensitivity, and other immune disorders related to cysteinal leukotriene-dependent activation.

Several animal studies have implicated CysLTs as playing an integral role in both vascular smooth muscle contraction and relaxation (Walch, L. et al., Am. J. Respir. Crit. Care. Med., 161(2 Pt 2):S107-11 (2000)). Activation of the receptor(s) on vascular smooth muscle provokes contraction whereas activation of the receptors on the endothelium produces contraction and/or relaxation. The vascular smooth muscle contractions are associated with activation of a single receptor subtype and in some vascular smooth muscles with activation of two receptor subtypes. However, the receptors implicated in the contraction of vessels such as pig pulmonary arteries and veins, dog inferior vena cava, and dog splenic and mesenteric veins remain to be established. There are sufficient data concerning some vascular tissues to suggest that relaxations induced by cysteinyl-leukotrienes via the stimulation of specific receptors present on the endothelium. The endothelium in human pulmonary arteries has one receptor (CysLT2) and activation induced the release of NO. However, in isolated human pulmonary veins two receptors are present, CysLT1 and CysLT2. Activation of the former induced the release of a contractile factor whereas activation of the CysLT2 receptor released NO. In guinea pig pulmonary artery and guinea pig thoracic aorta, one receptor has been demonstrated since the relaxations are blocked by ICI-198615. These data suggest the presence of a CysLT1 receptor. Activation of this receptor leads to the release of a relaxant factor, namely, nitric oxide. In contrast, in human pulmonary arteries and veins activation of a receptor that is resistant to ICI-198615 is associated with NO release. These results suggest that there may be species differences even when analogous vascular preparations are examined. While the cysteinyl-leukotrienes are known to relax vascular smooth muscle in a variety of preparations from different species, there are presently two pathways known to be involved in this response. One involves the metabolites of arachidonic acid via the cyclooxygenase enzymatic pathway and the other implicates products of the L-arginine enzymatic pathway. Although both pathways may be present and active in the endothelium of the vascular preparations only one of these enzymatic pathways may be dominant and responsible for the relaxations observed. Ortiz and coworkers have demonstrated that in pulmonary veins the dominant pathway for cysteinyl-leukotriene relaxations is the NO pathway. There are some reports from animal studies that support a dominant role for NO in pulmonary veins. In contrast, Allen and coworkers demonstrated that the LTC4-induced relaxations in isolated human saphenous veins were not modified by treatment of tissues with an NO inhibitor but were significantly enhanced after treatment with indomethacin. These authors suggested that a contracting factor derived from the arachidonic acid pathway was released in preparations challenged with LTC4. In addition, these investigators demonstrated that the NO inhibitor had no effect on the LTC4 relaxations. Together, these results suggest that cysteinyl-leukotriene effects in human pulmonary veins are dominated by the NO pathway whereas in human systemic veins these mediator effects are modified by metabolites of the cyclooxygenase pathway. Thus, the cysteinyl-leukotrienes may play a prominent role in the activation of these pathways.

In preferred embodiments, HGPRBMY11 polypeptides, including modulators, and fragments thereof, have uses which include, but are not limited to modulating vasoconstriction or vasodilation, either directly or indirectly, in addition to, treating, prognosing, preventing, ameliorating, and/or detecting vascular disorders, which include, for example, miscrovascular disease, vascular leak syndrome, aneurysm, stroke, embolism, thrombosis, coronary artery disease, arteriosclerosis, hypertension, hypotension, and/or atherosclerosis.

In preferred embodiments, HGPRBMY11 polypeptides, including modulators, and fragments thereof, have uses which include, for example, modulation of nitric oxide (NO) effects, modulation of nitric oxide vasculature effects, modulation of cyclooxygenase effects, modulation of cyclooxygenase vasculature effects, modulation of endothelin effects, and/or modulatoin of endothelin vasculature effects.

In preferred embodiments, HGPRBMY11 polypeptides, including modulators, and fragments thereof, have uses which include, for example, the treatment, detection, prevention, prognosis, and/or amelioration of pulmonary diseases, which include, for example chronic obstructive pulmonary disease (COPD) (Lee, E., et al., Am. J. Respir. Crit. Care. Med.,160(6):2079-85 (1999)), bronchial hyperresponsiveness, bronchial hypersensitivity (Yoshida, S., et al., Clin. Exp. Allergy.,30(1):64-70 (2000)), allergic rhinitis (Meltzer, E. O., Ann. Allergy. Asthma. Immunol., 84(2):176-85 (2000)).

Additionally, the HGPRBMY11 polypeptide also shares significant homology to puringergic receptors, which are described in more detail elsewhere herein. Such homology further emphasizes the potential role that the HGPRBMY11 polypeptide may play in cardiovascular, pulmonary, and immune modulation. For example, purinergic receptors have been implicated in playing roles in vasodilation, bronchoconstriction, immunosuppression, inhibition of platelet aggregation, and cardiac depression.

In preferred embodiments, the following N-terminal deletion mutants are encompassed by the present invention: M1-V330, E2-V330, P3-V330, N4-V330, G5-V330, T6-V330, F7-V330, S8-V330, N9-V330, N10-V330, N11-V330, S12-V330, R13-V330, N14-V330, C15-V330, T16-V330, I17-V330, E18-V330, N19-V330, F20-V330, K21-V330, R22-V330, E23-V330, F24-V330, F25-V330, P26-V330, I27-V330, V28-V330, Y29-V330, L30-V330, I31-V330, I32-V330, F33-V330, F34-V330, W35-V330, G36-V330, V37-V330, L38-V330, G39-V330, N40-V330, G41-V330, L42-V330, S43-V330, I44-V330, Y45-V330, V46-V330, F47-V330, L48-V330, Q49-V330, P50-V330, Y51-V330, K52-V330, K53-V330, S54-V330, T55-V330, S56-V330, V57-V330, N58-V330, V59-V330, F60-V330, M61-V330, L62-V330, N63-V330, L64-V330, A65-V330, I66-V330, S67-V330, D68-V330, L69-V330, L70-V330, F71-V330, I72-V330, S73-V330, T74-V330, L75-V330, P76-V330, F77-V330, R78-V330, A79-V330, D80-V330, Y81-V330, Y82-V330, L83-V330, R84-V330, G85-V330, S86-V330, N87-V330, W88-V330, I89-V330, F90-V330, G91-V330, D92-V330, L93-V330, A94-V330, C95-V330, R96-V330, I97-V330, M98-V330, S99-V330, Y100-V330, S101-V330, L102-V330, Y103-V330, V104-V330, N105-V330, M106-V330, Y107-V330, S108-V330, S109-V330, I110-V330, Y111-V330, F112-V330, L113-V330, T114-V330, V115-V330, L116-V330, S117-V330, V118-V330, V119-V330, R120-V330, F121-V330, L122-V330, A123-V330, M124-V330, V125-V330, H126-V330, P127-V330, F128-V330, R129-V330, L130-V330, L131-V330, H132-V330, V133-V330, T134-V330, S135-V330, I136-V330, R137-V330, S138-V330, A139-V330, W140-V330, I141-V330, L142-V330, C143-V330, G144-V330, I145-V330, I146-V330, W147-V330, I148-V330, L149-V330, 1150-V330, M151-V330, A152-V330, S153-V330, S154-V330, I155-V330, M156-V330, L157-V330, L158-V330, D159-V330, S160-V330, G161-V330, S162-V330, E163-V330, Q164-V330, N165-V330, G166-V330, S167-V330, V168-V330, T169-V330, S170-V330, C171-V330, L172-V330, E173-V330, L174-V330, N175-V330, L176-V330, Y177-V330, K178-V330, I179-V330, A180-V330, K181-V330, L182-V330, Q183-V330, T184-V330, M185-V330, N186-V330, Y187-V330, I188-V330, A189-V330, L190-V330, V191-V330, V192-V330, G193-V330, C194-V330, L195-V330, L196-V330, P197-V330, F198-V330, F199-V330, T200-V330, L201-V330, S202-V330, I203-V330, C204-V330, Y205-V330, L206-V330, L207-V330, I208-V330, I209-

V330, R210-V330, V211-V330, L212-V330, L213-V330, K214-V330, V215-V330, E216-V330, V217-V330, P218-V330, E219-V330, S220-V330, G221-V330, L222-V330, R223-V330, V224-V330, S225-V330, H226-V330, R227-V330, K228-V330, A229-V330, L230-V330, T231-V330, T232-V330, I233-V330, I234-V330, I235-V330, T236-V330, L237-V330, I238-V330, I239-V330, F240-V330, F241-V330, L242-V330, C243-V330, F244-V330, L245-V330, P246-V330, Y247-V330, H248-V330, T249-V330, L250-V330, R251-V330, T252-V330, V253-V330, H254-V330, L255-V330, T256-V330, T257-V330, W258-V330, K259-V330, V260-V330, G261-V330, L262-V330, C263-V330, K264-V330, D265-V330, R266-V330, L267-V330, H268-V330, K269-V330, A270-V330, L271-V330, V272-V330, I273-V330, T274-V330, L275-V330, A276-V330, L277-V330, A278-V330, A279-V330, A280-V330, N281-V330, A282-V330, C283-V330, F284-V330, N285-V330, P286-V330, L287-V330, L288-V330, Y289-V330, Y290-V330, F291-V330, A292-V330, G293-V330, E294-V330, N295-V330, F296-V330, K297-V330, D298-V330, R299-V330, L300-V330, K301-V330, S302-V330, A303-V330, L304-V330, R305-V330, K306-V330, G307-V330, H308-V330, P309-V330, Q310-V330, K311-V330, A312-V330, K313-V330, T314-V330, K315-V330, C316-V330, V317-V330, F318-V330, P319-V330, V320-V330, S321-V330, V322-V330, W323-V330, and/or L324-V330 of SEQ ID NO:2. Polynucleotide sequences encoding these polypeptides are also provided. The present invention also encompasses the use of the HGPRBMY11 N-terminal deletion polypeptides as immunogenic and/or antigenic epitopes as described elsewhere herein.

In preferred embodiments, the following C-terminal deletion mutants are encompassed by the present invention: M1-V330, M1-R329, M1-T328, M1-E327, M1-K326, M1-R325, M1-L324, M1-W323, M1-V322, M1-S321, M1-V320, M1-P319, M1-F318, M1-V317, M1-C316, M1-K315, M1-T314, M1-K313, M1-A312, M1-K311, M1-Q310, M1-P309, M1-H308, M1-G307, M1-K306, M1-R305, M1-L304, M1-A303, M1-S302, M1-K301, M1-L300, M1-R299, M1-D298, M1-K297, M1-F296, M1-N295, M1-E294, M1-G293, M1-A292, M1-F291, M1-Y290, M1-Y289, M1-L288, M1-L287, M1-P286, M1-N285, M1-F284, M1-C283, M1-A282, M1-N281, M1-A280, M1-A279, M1-A278, M1-L277, M1-A276, M1-L275, M1-T274, M1-I273, M1-V272, M1-L271, M1-A270, M1-K269, M1-H268, M1-L267, M1-R266, M1-D265, M1-K264, M1-C263, M1-L262, M1-G261, M1-V260, M1-K259, M1-W258, M1-T257, M1-T256, M1-L255, M1-H254, M1-V253, M1-T252, M1-R251, M1-L250, M1-T249, M1-H248, M1-Y247, M1-P246, M1-L245, M1-F244, M1-C243, M1-L242, M1-F241, M1-F240, M1-I239, M1-I238, M1-L237, M1-T236, M1-I235, M1-I234, M1-I233, M1-T232, M1-T231, M1-L230, M1-A229, M1-K228, M1-R227, M1-H226, M1-S225, M1-V224, M1-R223, M1-L222, M1-G221, M1-S220, M1-E219, M1-P218, M1-V217, M1-E216, M1-V215, M1-K214, M1-L213, M1-L212, M1-V211, M1-R210, M1-I209, M1-I208, M1-L207, M1-L206, M1-Y205, M1-C204, M1-I203, M1-S202, M1-L201, M1-T200, M1-F199, M1-F198, M1-P197, M1-L196, M1-L195, M1-C194, M1-G193, M1-V192, M1-V191, M1-L190, M1-A189, M1-I188, M1-Y187, M1-N186, M1-M185, M1-T184, M1-Q183, M1-L182, M1-K181, M1-A180, M1-I179, M1-K178, M1-Y177, M1-L176, M1-N175, M1-L174, M1-E173, M1-L172, M1-C171, M1-S170, M1-T169, M1-V168, M1-S167, M1-G166, M1-N165, M1-Q164, M1-E163, M1-S162, M1-G161, M1-S160, M1-D159, M1-L158, M1-L157, M1-M156, M1-I155, M1-S154, M1-S153, M1-A152, M1-M151, M1-I150, M1-L149, M1-I148, M1-W147, M1-I146, M1-I145, M1-G144, M1-C143, M1-L142, M1-I141, M1-W140, M1-A139, M1-S138, M1-R137, M1-I136, M1-S135, M1-T134, M1-V133, M1-H132, M1-L131, M1-L130, M1-R129, M1-F128, M1-P127, M1-H126, M1-V125, M1-M124, M1-A123, M1-L122, M1-F121, M1-R120, M1-V119, M1-V118, M1-S117, M1-L116, M1-V115, M1-T114, M1-L113, M1-F112, M1-Y111, M1-I110, M1-S109, M1-S108, M1-Y107, M1-M106, M1-N105, M1-V104, M1-Y103, M1-L102, M1-S101, M1-Y100, M1-S99, M1-M98, M1-I97, M1-R96, M1-C95, M1-A94, M1-L93, M1-D92, M1-G91, M1-F90, M1-I89, M1-W88, M1-N87, M1-S86, M1-G85, M1-R84, M1-L83, M1-Y82, M1-Y81, M1-D80, M1-A79, M1-R78, M1-F77, M1-P76, M1-L75, M1-T74, M1-S73, M1-I72, M1-F71, M1-L70, M1-L69, M1-D68, M1-S67, M1-I66, M1-A65, M1-L64, M1-N63, M1-L62, M1-M61, M1-F60, M1-V59, M1-N58, M1-V57, M1-S56, M1-T55, M1-S54, M1-K53, M1-K52, M1-Y51, M1-P50, M1-Q49, M1-L48, M1-F47, M1-V46, M1-Y45, M1-I44, M1-S43, M1-L42, M1-G41, M1-N40, M1-G39, M1-L38, M1-V37, M1-G36, M1-W35, M1-F34, M1-F33, M1-I32, M1-I31, M1-L30, M1-Y29, M1-V28, M1-I27, M1-P26, M1-F25, M1-F24, M1-E23, M1-R22, M1-K21, M1-F20, M1-N19, M1-E18, M1-I17, M1-T16, M1-C15, M1-N14, M1-R13, M1-S12, M1-N11, M1-N10, M1-N9, M1-S8, and/or M1-F7 of SEQ ID NO:2. Polynucleotide sequences encoding these polypeptides are also provided. The present invention also encompasses the use of the HGPRBMY11 C-terminal deletion polypeptides as immunogenic and/or antigenic epitopes as described elsewhere herein.

Alternatively, preferred polypeptides of the present invention may comprise polypeptide sequences corresponding to, for example, internal regions of the HGPRBMY11 polypeptide (e.g., any combination of both N- and C-terminal HGPRBMY11 polypeptide deletions) of SEQ ID NO:2. For example, internal regions could be defined by the equation: amino acid NX to amino acid CX, wherein NX refers to any N-terminal deletion polypeptide amino acid of HGPRBMY11 (SEQ ID NO:2), and where CX refers to any C-terminal deletion polypeptide amino acid of HGPRBMY11 (SEQ ID NO:2). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the HGPRBMY11 polypeptide.

In preferred embodiments, the following immunogenic and/or antigenic epitope polypeptides are encompassed by the present invention: amino acid residues from about amino acid 24 to about amino acid 48, from about amino acid 24 to about amino acid 32, from about amino acid 32 to about amino acid 40, from about amino acid 40 to about amino acid 48, from about amino acid 59 to about amino acid 83, from about amino acid 59 to about amino acid 68, from about amino acid 68 to about amino acid 76, from about amino acid 76 to about amino acid 83, from about amino acid 104 to about amino acid 125, from about amino acid 104 to about amino acid 112, from about amino acid 112 to about amino acid 120, from about amino acid 117 to about amino acid 125, from about amino acid 139 to about amino acid 158, from about amino acid 139 to about 148, from about 148 to about 156, from about 150 to about 158, from about 188 to about 206, from about 188 to about 196, from about 196 to about 204, from about 198 to about 206, from about 229 to about 250, from about 229 to about 238, from about 238 to about 246, from about 232 to about 250, from about 270 to about 292, from about 270 to about 278, from about 278 to about 286, and/or from about 284 to about 292 of SEQ ID NO:2 (FIGS. 1A-B). In this context, the term "about" may be construed to mean 1, 2, 3, 4, 5, 6, 7, 8, 9, or 10 amino acids beyond the N-terminus and/or C-terminus of the above referenced polypeptides. Polynucleotides encoding these polypeptides are also provided.

The HGPRBMY11 polypeptides of the present invention were determined to comprise several phosphorylation sites based upon the Motif algorithm (Genetics Computer Group, Inc.). The phosphorylation of such sites may regulate some biological activity of the HGPRBMY11 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the HGPRBMY11 polypeptide to associate with other polypeptides, particularly cognate ligand for HGPRBMY11, or its ability to modulate certain cellular signal pathways.

The HGPRBMY11 polypeptide was predicted to comprise four PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184(1986), and Kishimoto A., Nishiyama K., Nakanishi H., Uratsuji Y., Nomura H., Takeyama Y., Nishizuka Y., J. Biol. Chem. 260: 12492-12499(1985); which are hereby incorporated by reference herein.

In preferred embodiments, the following PKC phosphorylation site polypeptides are encompassed by the present invention: LLHVTSIRSAWIL (SEQ ID NO:19), SGLRVSHRKALTT (SEQ ID NO:20), FLPYHTLRTVHLT (SEQ ID NO:21), and/or TVHLTTWKVGLCK (SEQ ID NO:22). Polynucleotides encoding these polypeptides are also provided. The present invention also encompasses the use of the HGPRBMY11 PKC phosphorylation site polypeptides as immunogenic and/or antigenic epitopes as described elsewhere herein.

The HGPRBMY11 polypeptide was predicted to comprise two cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240-4245(1980); Glass D. B., Smith S. B., J. Biol. Chem. 258:14797-14803 (1983); and Glass D. B., El-Maghrabi M. R., Pilkis S. J., J. Biol. Chem. 261:2987-2993(1986); which is hereby incorporated herein in its entirety.

In preferred embodiments, the following cAMP- and cGMP-dependent protein kinase phosphorylation site polypeptide is encompassed by the present invention: FLQPYKKSTSVNVF (SEQ ID NO:56), and/or VSVWLRKETRV (SEQ ID NO:57). Polynucleotides encoding these polypeptides are also provided. The present invention also encompasses the use of these cAMP- and cGMP-dependent protein kinase phosphorylation site polypeptides as immunogenic and/or antigenic epitope as described elsewhere herein.

The HGPRBMY11 polypeptide was predicted to comprise two casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation sites may be found in reference to the following publication: Pinna L. A., Biochim. Biophys. Acta 1054:267-284(1990); which is hereby incorporated herein in its entirety.

In preferred embodiments, the following casein kinase II phosphorylation site polypeptide is encompassed by the present invention: IMLLDSGSEQNGSV (SEQ ID NO:58), and/or NGSVTSCLELNLYK (SEQ ID NO:59). Polynucleotides encoding these polypeptides are also provided. The present invention also encompasses the use of these casein kinase II phosphorylation site polypeptides as immunogenic and/or antigenic epitope as described elsewhere herein.

The HGPRBMY11 polypeptide was predicted to comprise six N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99(1988); and Grand R. J. A., Biochem. J. 258:625-638(1989); which is hereby incorporated herein in its entirety.

In preferred embodiments, the following N-myristoylation site polypeptides are encompassed by the present invention: MEPNGTFSNNNSRNC (SEQ ID NO:60), IIFFWGV-LGNGLSIYV (SEQ ID NO:61), FWGVLGNGLSIYVFLQ (SEQ ID NO:62), MLLDSGSEQNGSVTSC (SEQ ID NO:63), GSEQNGSVTSCLELNL (SEQ ID NO:64), and/or EVPESGLRVSHRKALT (SEQ ID NO:65). Polynucleotides encoding these polypeptides are also provided. The present invention also encompasses the use of these N-myristoylation site polypeptides as immunogenic and/or antigenic epitopes as described elsewhere herein.

The HGPRBMY11 polypeptide has been shown to comprise four glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

In preferred embodiments, the following asparagine glycosylation site polypeptides are encompassed by the present invention: MEPNGTFSNNNS (SEQ ID NO:23), GTF-SNNNSRNCTIE (SEQ ID NO:24), NNNSRNCTIENFKR (SEQ ID NO:25), and/or SGSEQNGSVTSCLE (SEQ ID NO:26). Polynucleotides encoding these polypeptides are also provided. The present invention also encompasses the use of the HGPRBMY11 asparagine glycosylation site polypeptides as immunogenic and/or antigenic epitopes as described elsewhere herein.

The present invention encompasses the identification of compounds and drugs which stimulate HGPRBMY11 on the one hand (i.e., agonists) and which inhibit the function of HGPRBMY11 on the other hand (i.e., antagonists). In general, such screening procedures involve providing appropriate cells which express the receptor polypeptide of the present invention on the surface thereof. Such cells may include, for example, cells from mammals, yeast, *Drosophila* or *E. coli*. In a preferred embodimenta, a polynucleotide encoding the receptor of the present invention may be employed to transfect cells to thereby express the HGPRBMY11 polypeptide. The expressed receptor may then be contacted with a test compound to observe binding, stimulation or inhibition of a functional response.

Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUSI-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1694 of SEQ ID NO:1, b is an integer between 15 to 1708, where both a and b correspond to the positions of nucleotide residues shown in SEQ ID NO:1, and where b is greater than or equal to a+14.

Features of the Polypeptide Encoded by Gene No:2

The polypeptide of this gene provided as SEQ ID NO:30 (FIGS. 6A-B), encoded by the polynucleotide sequence according to SEQ ID NO:29 (FIGS. 6A-B), has significant homology at the nucleotide and amino acid level to a number of G-protein coupled receptors, which include, for example, the chick purinergic receptor protein (P2YR_CHICK; Genbank Accession No:gi|P34996; SEQ ID NO:3), the turkey purinergic receptor protein, also known as, 6H1 orphan receptor (P2YR_MELGA; Genbank Accession No:gi|P49652; SEQ ID NO:4), the rat purinergic receptor (P2YR_RAT; Genbank Accession No:gi|P49651; SEQ ID NO:5), the human cysteinyl leukotriene receptor protein (Genbank Accession No.: gi|11422069; SEQ ID NO:6); the chick purinergic receptor 5 protein (P2Y5_CHICK; Genbank Accession No.: gi|P32250; SEQ ID NO:7); and the human G-protein-coupled receptor GPR17 (GPRH_HUMAN; Genbank Accession No. gi|Q13304; SEQ ID NO:8). An alignment of the HGPRBMY11v1 polypeptide with these proteins is provided in FIGS. 2A-B.

The determined nucleotide sequence of the HGPRBMY11v1 cDNA in FIGS. 6A-B (SEQ ID NO:29) contains an open reading frame encoding a protein of about 346 amino acid residues, with a deduced molecular weight of about 39.6 kDa. The amino acid sequence of the predicted HGPRBMY11v1 polypeptide is shown in FIGS. 6A-B (SEQ ID NO:30). The HGPRBMY11v1 protein shown in FIGS. 6A-B is about 29.5% identical and 43.9% similar to the chick purinergic receptor protein (P2YR_CHICK; Genbank Accession No:gi|P34996; SEQ ID NO:3); about 29.8% identical and 44.2% similar to the turkey purinergic receptor protein, also known as, 6H1 orphan receptor (P2YR_MELGA; Genbank Accession No:gi|P49652; SEQ ID NO:4); about 29.6% identical and 44% similar to the rat purinergic receptor (P2YR_RAT; Genbank Accession No:gi|P49651; SEQ ID NO:5); about 37.2% identical and 49% similar to the human cysteinyl leukotriene receptor protein (Genbank Accession No.: gi|11422069; SEQ ID NO:6); about 36.7% identical and 46.1% identical to the chick purinergic receptor 5 protein (P2Y5_CHICK; Genbank Accession No.: gi|P32250; SEQ ID NO:7); and about 36.2% identical and 46.1% similar to the human G-protein-coupled receptor GPR17 (GPRH_HUMAN; Genbank Accession No. gi|Q13304; SEQ ID NO:8) as shown in FIG. 5.

The GPR17 protein is a G-protein coupled receptor that is predominately expressed in the brain and is believed to represent a chemokine receptor (J. Leukoc. Biol. 59 (1), 18-23 (1996)). As a result, the GPR17 protein may modulate the potent chemoattractant and activation activities for leukocytes. GPR17 was also found to be localized to chromosome band 2q21 which may suggest a potential disease association (J. Neurochem. 70 (4), 1357-1365 (1998)).

The chick P2YR protein receptor is a G-protein coupled receptor for extracellular adenine nucleotides such as ATP and ADP and seems to mediate its action via a pertussis toxin insensitive G-protein, probably belonging to the GQ family that activates a phosphatidylinositol-calcium second messenger system. The chick P2YR protein is expressed specifically in brain, spinal cord, gastrointestinal tract, spleen and leg muscle suggested a putative association of P2YR to disorders in these tissues. Expression of the chick P2YR (cRNA) in *Xenopus* oocytes resulted in a slowly-developing inward current was observed in response to application of ATP—which emphasized its identity as a P2Y receptor (FEBS Lett. 324 (2), 219-225 (1993)). The 3D structure of this receptor has been described (Drug Des Discov 13 (2), 133-154 (1995)). Based upon the conservation of critical residues within the HGPRBMY11v1 protein, it is likely that HGPRBMY11v1 shares similar structure, and potentially function to the chich P2YR receptor.

The HGPRBMY11v1 polypeptide was predicted to comprise 7 transmembrane domains using the TMPRED program (K Hofmann, W Stoffel, Biol. Chem., 347:166, 1993). The predicted transmembrane domains of the HGPRBMY11v1 polypeptide have been termed TM1 thru TM7 and are located from about amino acid 40 to about amino acid 64 (TM1; SEQ ID NO:31); from about amino acid 75 to about amino acid 99 (TM2; SEQ ID NO:32); from about amino acid 120 to about amino acid 141 (TM3; SEQ ID NO:33); from about amino acid 155 to about amino acid 173 (TM4; SEQ ID NO:34); from about amino acid 195 to about amino acid 222 (TM5; SEQ ID NO:35); from about amino acid 245 to about amino acid 266 (TM6; SEQ ID NO:36); and/or from about amino acid 286 to about amino acid 308 (TM7; SEQ ID NO:37) of SEQ ID NO:30 (FIGS. 6A-B). The predicted transmembrane domains aligned with the predicted transmembrane domains of related GPCRs at the sequence level (see FIG. 2). The seven transmembrane domains of the present invention are characteristic of G-protein coupled receptors as described more particularly elsewhere herein. In this context, the term "about" may be construed to mean 1, 2, 3, 4, 5, 6, 7, 8, 9, or 10 amino acids beyond the N-Terminus and/or C-terminus of the above referenced polypeptide.

In preferred embodiments, the following transmembrane domain polypeptides are encompassed by the present invention: FFPIYLIIFFWGVLGNGLSIYVFL (SEQ ID NO:31), VFMLNLAISDLLFISTLPFRADYYL (SEQ ID NO:32), VNMYSSIYFLTVLSVVRFLAMV (SEQ ID NO:33), AWILCGIIWILIMASSIMLL (SEQ ID NO:34), IALVVGCLLPFFTLSICYL (SEQ ID NO:35), ALTTIIITLIIFFLCFLPYHTL (SEQ ID NO:36), and/or ALVITLALAAANACFNPLLYYFA (SEQ ID NO:37). Polynucleotides encoding these polypeptides are also provided. The present invention also encompasses the use of the HGPRBMY11v1 transmembrane domain polypeptides as immunogenic and/or antigenic epitopes as described elsewhere herein.

In preferred embodiments, the present invention encompasses the use of N-terminal deletions, C-terminal deletions, or any combination of N-terminal and C-terminal deletions of any one or more of the HGPRBMY11v1 TM1 thru TM7 transmembrane domain polypeptides as antigenic and/or immunogenic epitopes.

In preferred embodiments, the present invention also encompasses the use of N-terminal deletions, C-terminal deletions, or any combination of N-terminal and C-terminal deletions of any one or more of the amino acids intervening (i.e., GPCR extracellular or intracellular loops) the HGPRBMY11v1 TM1 thru TM7 transmembrane domain polypeptides as antigenic and/or immunogenic epitopes.

In preferred embodiments, the present invention encompasses a polynucleotide lacking the initiating start codon, in addition to, the resulting encoded polypeptide of HGPRBMY11v1. Specifically, the present invention encompasses the polynucleotide corresponding to nucleotides 4 thru 1038 of SEQ ID NO:29, and the polypeptide corresponding to amino acids 2 thru 346 of SEQ ID NO:30. Also encompassed are recombinant vectors comprising said encoding sequence, and host cells comprising said vector.

Based upon the strong homology to members of the G-protein coupled receptor proteins, the HGPRBMY11v1 polypeptide is expected to share at least some biological activity with G-protein coupled receptor, and preferably with purinergic receptor GPCR members, and more preferably with cysteinal leukotriene GPCR family members.

HGPRBMY11v1 polynucleltides and polypeptides are expected to have all of the same utilities asserted for HGPRBMY11 and HGPRBMY11v2 herein.

In preferred embodiments, the following N-terminal HGPRBMY11v1 deletion polypeptides are encompassed by the present invention: M1-V346, E2-V346, R3-V346, K4-V346, F5-V346, M6-V346, S7-V346, L8-V346, Q9-V346, P10-V346, S11-V346, I12-V346, S13-V346, V14-V346, S15-V346, and/or E16-V346 of SEQ ID NO:30. Polynucleotide sequences encoding these polypeptides are also provided. The present invention also encompasses the use of these N-terminal HGPRBMY11v1 deletion polypeptides as immunogenic and/or antigenic epitopes as described elsewhere herein.

In preferred embodiments, the following C-terminal HGPRBMY11v1 deletion polypeptides are encompassed by the present invention: M1-V346, M1-R345, M1-T344, M1-E343, M1-K342, M1-R341, M1-L340, M1-W339, M1-V338, M1-S337, M1-V336, M1-P335, M1-F334, M1-V333, M1-C332, M1-K331, M1-T330, M1-K329, M1-A328, M1-K327, M1-Q326, M1-P325, M1-H324, M1-G323, M1-K322, M1-R321, M1-L320, M1-A319, M1-S318, M1-K317, M1-L316, M1-R315, M1-D314, M1-K313, M1-F312, M1-N311, M1-E310, M1-G309, M1-A308, M1-F307, M1-Y306, M1-Y305, M1-L304, M1-L303, M1-P302, M1-N301, M1-F300, M1-C299, M1-A298, M1-N297, M1-A296, M1-A295, M1-A294, M1-L293, M1-A292, M1-L291, M1-T290, M1-I289, M1-V288, M1-L287, M1-A286, M1-K285, M1-H284, M1-L283, M1-R282, M1-D281, M1-K280, M1-C279, M1-L278, M1-G277, M1-V276, M1-K275, M1-W274, M1-T273, M1-T272, M1-L271, M1-H270, M1-V269, M1-T268, M1-R267, M1-L266, M1-T265, M1-H264, M1-Y263, M1-P262, M1-L261, M1-F260, M1-C259, M1-L258, M1-F257, M1-F256, M1-I255, M1-I254, M1-L253, M1-T252, M1-I251, M1-I250, M1-L249, M1-T248, M1-T247, M1-L246, M1-A245, M1-K244, M1-R243, M1-H242, M1-S241, M1-V240, M1-R239, M1-L238, M1-G237, M1-S236, M1-E235, M1-P234, M1-V233, M1-E232, M1-V231, M1-K230, M1-L229, M1-L228, M1-V227, M1-R226, M1-I225, M1-I224, M1-L223, M1-L222, M1-Y221, M1-C220, M1-L219, M1-S218, M1-L217, M1-T216, M1-F215, M1-F214, M1-P213, M1-L212, M1-L211, M1-C210, M1-G209, M1-V208, M1-V207, M1-L206, M1-A205, M1-I204, M1-Y203, M1-N202, M1-M201, M1-T200, M1-Q199, M1-L198, M1-K197, M1-A196, M1-I195, M1-K194, M1-Y193, M1-L192, M1-N191, M1-L190, M1-E189, M1-L188, M1-C187, M1-S186, M1-T185, M1-V184, M1-S183, M1-G182, M1-N181, M1-Q180, M1-E179, M1-S178, M1-G177, M1-S176, M1-D175, M1-L174, M1-L173, M1-M172, M1-I71, M1-S170, M1-S169, M1-A168, M1-M167, M1-I66, M1-L165, M1-I164, M1-W163, M1-I162, M1-I161, M1-G160, M1-C159, M1-L158, M1-I157, M1-W156, M1-A155, M1-S154, M1-R153, M1-I152, M1-S151, M1-T150, M1-V149, M1-H148, M1-L147, M1-L146, M1-R145, M1-F144, M1-P143, M1-H142, M1-V141, M1-M140, M1-A139, M1-L138, M1-F137, M1-R136, M1-V135, M1-V134, M1-S133, M1-L132, M1-V131, M1-T130, M1-L129, M1-F128, M1-Y127, M1-I126, M1-S125, M1-S124, M1-Y123, M1-M122, M1-N121, M1-V120, M1-Y119, M1-L118, M1-S117, M1-Y116, M1-S115, M1-M114, M1-I113, M1-R112, M1-C111, M1-A110, M1-L109, M1-D108, M1-G107, M1-F106, M1-I105, M1-W104, M1-N103, M1-S102, M1-G101, M1-R100, M1-L99, M1-Y98, M1-Y97, M1-D96, M1-A95, M1-R94, M1-F93, M1-P92, M1-L91, M1-T90, M1-S89, M1-I88, M1-F87, M1-L86, M1-L85, M1-D84, M1-S83, M1-I82, M1-A81, M1-L80, M1-N79, M1-L78, M1-M77, M1-F76, M1-V75, M1-N74, M1-V73, M1-S72, M1-T71, M1-S70, M1-K69, M1-K68, M1-Y67, M1-P66, M1-Q65, M1-L64, M1-F63, M1-V62, M1-Y61, M1-I60, M1-S59, M1-L58, M1-G57, M1-N56, M1-G55, M1-L54, M1-V53, M1-G52, M1-W51, M1-F50, M1-F49, M1-I48, M1-I47, M1-L46, M1-Y45, M1-V44, M1-I43, M1-P42, M1-F41, M1-F40, M1-E39, M1-R38, M1-K37, M1-F36, M1-N35, M1-E34, M1-I33, M1-T32, M1-C31, M1-N30, M1-R29, M1-S28, M1-N27, M1-N26, M1-N25, M1-S24, M1-F23, M1-T22, M1-G21, M1-N20, M1-P19, and/or M1-E18 of SEQ ID NO:30. Polynucleotide sequences encoding these polypeptides are also provided. The present invention also encompasses the use of these C-terminal HGPRBMY11v1 deletion polypeptides as immunogenic and/or antigenic epitopes as described elsewhere herein.

Alternatively, preferred polypeptides of the present invention may comprise polypeptide sequences corresponding to, for example, internal regions of the HGPRBMY11v1 polypeptide (e.g., any combination of both N- and C-terminal HGPRBMY11v1 polypeptide deletions) of SEQ ID NO:30. For example, internal regions could be defined by the equation: amino acid NX to amino acid CX, wherein NX refers to any N-terminal deletion polypeptide amino acid of HGPRBMY11v1 (SEQ ID NO:30), and where CX refers to any C-terminal deletion polypeptide amino acid of HGPRBMY11v1 (SEQ ID NO:30). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the HGPRBMY11v1 polypeptide.

In preferred embodiments, the following immunogenic and/or antigenic epitope polypeptides are encompassed by the present invention: amino acid residues from about amino acid 24 to about amino acid 48, from about amino acid 24 to about amino acid 32, from about amino acid 32 to about amino acid 40, from about amino acid 40 to about amino acid 48, from about amino acid 59 to about amino acid 83, from about amino acid 59 to about amino acid 68, from about amino acid 68 to about amino acid 76, from about amino acid 76 to about amino acid 83, from about amino acid 104 to about amino acid 125, from about amino acid 104 to about amino acid 112, from about amino acid 112 to about amino acid 120, from about amino acid 117 to about amino acid 125, from about amino acid 139 to about amino acid 158, from about 139 to about 148, from about 148 to about 156, from about 150 to about 158, from about 188 to about 206, from about 188 to about 196, from about 196 to about 204, from about 198 to about 206, from about 229 to about 250, from about 229 to about 238, from about 238 to about 246, from about 232 to about 250, from about 270 to about 292, from about 270 to about 278, from about 278 to about 286, and/or from about 284 to about 292 of SEQ ID NO:30 (FIGS. 6A-B). In this context, the term "about" may be construed to mean 1, 2, 3, 4, 5, 6, 7, 8, 9, or 10 amino acids beyond the N-terminus and/or C-terminus of the above referenced polypeptides. Polynucleotides encoding these polypeptides are also provided.

The HGPRBMY11v1 polypeptides of the present invention were determined to comprise several phosphorylation sites based upon the Motif algorithm (Genetics Computer Group, Inc.). The phosphorylation of such sites may regulate some biological activity of the HGPRBMY11v1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the HGPRBMY11v1 polypeptide to associate with other polypeptides, particularly cognate ligand for HGPRBMY11v1, or its ability to modulate certain cellular signal pathways.

The HGPRBMY11v1 polypeptide was predicted to comprise four PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177-184(1986), and Kishimoto A., Nishiyama K., Nakanishi H., Uratsuji Y., Nomura H., Takeyama Y., Nishizuka Y., J. Biol. Chem. 260: 12492-12499(1985); which are hereby incorporated by reference herein.

In preferred embodiments, the following PKC phosphorylation site polypeptides are encompassed by the present invention: LLHVTSIRSAWIL (SEQ ID NO:38), SGL-RVSHRKALTT (SEQ ID NO:39), FLPYHTLRTVHLT (SEQ ID NO:40), and/or TVHLTTWKVGLCK (SEQ ID NO:41). Polynucleotides encoding these polypeptides are also provided. The present invention also encompasses the use of the HGPRBMY11v1 PKC phosphorylation site polypeptides as immunogenic and/or antigenic epitopes as described elsewhere herein.

The HGPRBMY11v1 polypeptide was predicted to comprise two cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240-4245(1980); Glass D. B., Smith S. B., J. Biol. Chem. 258:14797-14803 (1983); and Glass D. B., E1-Maghrabi M. R., Pilkis S. J., J. Biol. Chem. 261:2987-2993(1986); which is hereby incorporated herein in its entirety.

In preferred embodiments, the following cAMP- and cGMP-dependent protein kinase phosphorylation site polypeptide is encompassed by the present invention: FLQPYKKSTSVNVF (SEQ ID NO:66), and/or VSVWLR-KETRV (SEQ ID NO:67). Polynucleotides encoding these polypeptides are also provided. The present invention also encompasses the use of these cAMP- and cGMP-dependent protein kinase phosphorylation site polypeptides as immunogenic and/or antigenic epitope as described elsewhere herein.

The HGPRBMY11v1 polypeptide was predicted to comprise two casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation sites may be found in reference to the following publication: Pinna L. A., Biochim. Biophys. Acta 1054:267-284(1990); which is hereby incorporated herein in its entirety.

In preferred embodiments, the following casein kinase II phosphorylation site polypeptide is encompassed by the present invention: LQPSISVSEMEPNG (SEQ ID NO:68), PSISVSEMEPNGTF (SEQ ID NO:69), IMLLDSGSE-QNGSV (SEQ ID NO:70), and/or NGSVTSCLELNLYK (SEQ ID NO:71). Polynucleotides encoding these polypeptides are also provided. The present invention also encompasses the use of these casein kinase II phosphorylation site polypeptides as immunogenic and/or antigenic epitope as described elsewhere herein.

The HGPRBMY11v1 polypeptide was predicted to comprise six N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69-99(1988); and Grand R. J. A., Biochem. J. 258:625-638(1989); which is hereby incorporated herein in its entirety.

In preferred embodiments, the following N-myristoylation site polypeptides are encompassed by the present invention: MEPNGTFSNNNSRNC (SEQ ID NO:72), IIFFWGV-LGNGLSIYV (SEQ ID NO:73), FWGVLGNGLSIYVFLQ (SEQ ID NO:74), MLLDSGSEQNGSVTSC (SEQ ID NO:75), GSEQNGSVTSCLELNL (SEQ ID NO:76), and/or EVPESGLRVSHRKALT (SEQ ID NO:77). Polynucleotides encoding these polypeptides are also provided. The present invention also encompasses the use of these N-myristoylation site polypeptides as immunogenic and/or antigenic epitopes as described elsewhere herein.

The HGPRBMY11v1 polypeptide has been shown to comprise four glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

In preferred embodiments, the following asparagine glycosylation site polypeptides are encompassed by the present invention: SEMEPNGTFSNNNS (SEQ ID NO:42), GTF-SNNNSRNCTE (SEQ ID NO:43), NNNSRNCTIENFKR (SEQ ID NO:44), and/or SGSEQNGSVTSCLE (SEQ ID NO:45). Polynucleotides encoding these polypeptides are also provided. The present invention also encompasses the use of the HGPRBMY11v1 asparagine glycosylation site polypeptides as immunogenic and/or antigenic epitopes as described elsewhere herein.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1027 of SEQ ID NO:29, b is an integer between 15 to 1041, where both a and b correspond to the positions of nucleotide residues shown in SEQ ID NO:29, and where b is greater than or equal to a+14.

TABLE I

| Gene No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | HGPRBMY11 - (also referred to as GPCR74; and/or GPCR 81) | PTA-2766 Dec. 08, 2000 | PSport1 | 1 | 1708 | 515 | 1504 | 2 | 330 |
| 2. | HGPRBMY11v1 - (also referred to as GPCR74 and/or GPCR 81 splice variant) | N/A | N/A | 29 | 1041 | 1 | 1038 | 30 | 346 |
| 3. | HGPRBMY11v2 | N/A | N/A | 54 | 1026 | 1 | 1023 | 55 | 341 |

Table I summarizes the information corresponding to each "Gene No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC deposit No:PTA-2766 and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1, 29, and/or 54 and the predicted translated amino acid sequence identified as SEQ ID NO:2, 30, and/or 55, but also a sample of plasmid DNA containing a cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, 29, and/or 54, SEQ ID NO:2, 30, and/or 55, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, 29, and/or 54, SEQ ID NO:2, 30, and/or 55, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, 29, and/or 54, and/or a cDNA provided in ATCC Deposit No:Z. The present invention also provides a polypeptide comprising, or alternatively consisting of, the sequence identified as SEQ ID NO:2, 30, and/or 55, and/or a polypeptide encoded by the cDNA provided in ATCC deposit No:PTA-2766. The present invention also provides polynucleotides encoding a polypeptide comprising, or alternatively consisting of the polypeptide sequence of SEQ ID NO:2, 30, and/or 55, and/or a polypeptide sequence encoded by the cDNA contained in ATCC deposit No:PTA-2766.

Preferably, the present invention is directed to a polynucleotide comprising, or alternatively consisting of, the sequence identified as SEQ ID NO:1, 29, and/or 54, and/or a cDNA provided in ATCC Deposit No:Z that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, 29, and/or 54, the sequence contained in a deposit, and/or the nucleic acid sequence encoding the sequence disclosed as SEQ ID NO:2, 30, and/or 55.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE II

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C.; 1 × SSC -or- 42° C.; 1 × SSC, 50% formamide | 65° C.; 0.3 × SSC |
| B | DNA:DNA | <50 | Tb*; 1 × SSC | Tb*; 1 × SSC |
| C | DNA:RNA | > or equal to 50 | 67° C.; 1 × SSC -or- 45° C.; 1 × SSC, 50% formamide | 67° C.; 0.3 × SSC |
| D | DNA:RNA | <50 | Td*; 1 × SSC | Td*; 1 × SSC |
| E | RNA:RNA | > or equal to 50 | 70° C.; 1 × SSC -or- 50° C.; 1 × SSC, 50% formamide | 70° C.; 0.3 × SSC |
| F | RNA:RNA | <50 | Tf*; 1 × SSC | Tf*; 1 × SSC |
| G | DNA:DNA | > or equal to 50 | 65° C.; 4 × SSC -or- 45° C.; 4 × SSC, 50% formamide | 65° C.; 1 × SSC |
| H | DNA:DNA | <50 | Th*; 4 × SSC | Th*; 4 × SSC |
| I | DNA:RNA | > or equal to 50 | 67° C.; 4 × SSC -or- 45° C.; 4 × SSC, 50% formamide | 67° C.; 1 × SSC |
| J | DNA:RNA | <50 | Tj*; 4 × SSC | Tj*; 4 × SSC |
| K | RNA:RNA | > or equal to 50 | 70° C.; 4 × SSC -or- 40° C.; 6 × SSC, 50% formamide | 67° C.; 1 × SSC |
| L | RNA:RNA | <50 | Tl*; 2 × SSC | Tl*; 2 × SSC |
| M | DNA:DNA | > or equal to 50 | 50° C.; 4 × SSC -or- 40° C. 6 × SSC, 50% formamide | 50° C.; 2 × SSC |
| N | DNA:DNA | <50 | Tn*; 6 × SSC | Tn*; 6 × SSC |
| O | DNA:RNA | > or equal to 50 | 55° C.; 4 × SSC -or- 42° C.; 6 × SSC, 50% formamide | 55° C.; 2 × SSC |
| P | DNA:RNA | <50 | Tp*; 6 × SSC | Tp*; 6 × SSC |
| Q | RNA:RNA | > or equal to 50 | 60° C.; 4 × SSC -or- 45° C.; 6 × SSC, 50% formamide | 60° C.; 2 × SSC |
| R | RNA:RNA | <50 | Tr*; 4 × SSC | Tr*; 4 × SSC |

‡The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g, MegAlign program of the DNA * Star suite of programs, etc).
†SSPE (1 × SSPE is 0.15M NaCl, 10 mM NaH2PO4, and 1.25 mM EDTA, pH 7.4) can be substituted for SSC (1 × SSC is 0.15M NaCl and 15 mM sodium citrate) in the hybridization and wash buffers; washes are performed for 15 minutes after hybridization is complete. The hybridizations and washes may additionally include 5X Denhardt's reagent, .5-1.0% SDS, 100 ug/ml denatured, fragmented salmon sperm DNA, 0.5% sodium pyrophosphate, and up to 50% formamide.
*Tb-Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6(log$_{10}$[Na+]) + 0.41(%G + C) − (600/N), where N is the number of bases in the hybrid, and [Na+] is the concentration of sodium ions in the hybridization buffer ([NA+]) for 1 × SSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487-491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643-1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:1, 29, and/or 54, the complementary strand thereto, and/or the cDNA sequence contained in the deposited clone.

The present invention also encompasses variants of the polypeptide sequence, and/or fragments therein, disclosed in SEQ ID NO:2, 30, and/or 55, a polypeptide encoded by the polynucleotide sequence in SEQ ID NO:1, 29, and/or 54, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a HGPRBMY11 related polypeptide having an amino acid sequence as shown in the sequence listing and described in SEQ ID NO:1, 29, and/or 54 or the cDNA contained in ATCC deposit No:PTA-2766; (b) a nucleotide sequence encoding a mature HGPRBMY11 related polypeptide having the amino acid sequence as shown in the sequence listing and described in SEQ ID NO:1, 29, and/or 54 or the cDNA contained in ATCC deposit No:PTA-2766; (c) a nucleotide sequence encoding a biologically active fragment of a HGPRBMY11 related polypeptide having an amino acid sequence shown in the sequence listing and described in SEQ ID NO:1, 29, and/or 54 or the cDNA contained in ATCC deposit No:PTA-2766; (d) a nucleotide sequence encoding an antigenic fragment of a HGPRBMY11 related polypeptide having an amino acid sequence sown in the sequence listing and described in SEQ ID NO:1, 29, and/or 54 or the cDNA contained in ATCC deposit No:PTA-2766; (e) a nucleotide sequence encoding a HGPRBMY11 related polypeptide comprising the complete amino acid sequence encoded by a human cDNA plasmid contained in SEQ ID NO:1, 29, and/or 54 or the cDNA contained in ATCC deposit No:PTA-2766; (f) a nucleotide sequence encoding a mature HGPRBMY11 related polypeptide having an amino acid sequence encoded by a human cDNA plasmid contained in SEQ ID NO:1, 29, and/or 54 or the cDNA contained in ATCC deposit No:PTA-2766; (g) a nucleotide sequence encoding a biologically active fragment of a HGPRBMY11 related polypeptide having an amino acid sequence encoded by a human cDNA plasmid contained in SEQ ID NO:1, 29, and/or 54 or the cDNA contained in ATCC deposit No:PTA-2766; (h) a nucleotide sequence encoding an antigenic fragment of a HGPRBMY11 related polypeptide having an amino acid sequence encoded by a human cDNA plasmid contained in SEQ ID NO:1, 29, and/or 54 or the cDNA contained in ATCC deposit No:PTA-2766; (i) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a HGPRBMY11 related polypeptide having an amino acid sequence as shown in the sequence listing and descried in Table I; (b) a nucleotide sequence encoding a mature HGPRBMY11 related polypeptide having the amino acid sequence as shown in the sequence listing and descried in Table I; (c) a nucleotide sequence encoding a biologically active fragment of a HGPRBMY11 related polypeptide having an amino acid sequence as shown in the sequence listing and descried in Table I; (d) a nucleotide sequence encoding an antigenic fragment of a HGPRBMY11 related polypeptide having an amino acid sequence as shown in the sequence listing and descried in Table I; (e) a nucleotide sequence encoding a HGPRBMY11 related polypeptide comprising the complete amino acid sequence encoded by a human cDNA in a cDNA plasmid contained in the ATCC Deposit and described in Table I; (f) a nucleotide sequence encoding a mature HGPRBMY11 related polypeptide having an amino acid sequence encoded by a human cDNA in a cDNA plasmid contained in the ATCC Deposit and described in Table I: (g) a nucleotide sequence encoding a biologically active fragment of a HGPRBMY11 related polypeptide having an amino acid sequence encoded by a human cDNA in a cDNA plasmid contained in the ATCC Deposit and described in Table I; (h) a nucleotide sequence encoding an antigenic fragment of a HGPRBMY11 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, 30, and/or 55, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, 30, and/or 55, a polypeptide sequence encoded by the nucleotide sequence in SEQ ID NO:1, 29, and/or 54, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected.

Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):46734680, (1994)), which is based on the algorithm of Higgins, D. G., et al., Computer Applications in the Biosciences (CABIOS), 8(2):189-191, (1992). In a sequence alignment the query and subject sequences are both amino acid sequences. The result of said global sequence alignment is in percent identity. Preferred parameters used in a CLUSTALW alignment of polypeptide sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)).

Moreover, ample evidence demonstrates that variants often retain a biological activity similar to that of the naturally occurring protein. For example, Gayle and coworkers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-bomo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Mg, D-Arg, homo-Arg, D-homo-Arg, Met, D-Met, Ile, D-Ile, Orn, D-Orn |
| Methionine | M | D-Met, S-Me-Cys, lIe, D-Ile, Leu, D-Leu, Val, D-Val |
| Phenylalanine | F | D-Phe, Tyr, D-Thr, L-Dopa, His, D-His, Trp, D-Trp, Trans-3, 4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, aIlo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

Moreover, the invention further includes polypeptide variants created through the application of molecular evolution ("DNA Shuffling") methodology to the polynucleotide disclosed as SEQ ID NO:1, 29, and/or 54, the sequence of the clone submitted in a deposit, and/or the cDNA encoding the polypeptide disclosed as SEQ ID NO:2, 30, and/or 55. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 29, and/or 54 or the complementary strand thereto, or is a portion of a polynucleotide sequence encoding the polypeptide of SEQ ID NO:2, 30, and/or 55. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1, 29, and/or 54. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:1, 29, and/or 54, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2, 30, and/or 55 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1-60, can be deleted from the amino terminus of the full-length polypeptide. Similarly, any number of amino acids, ranging from 1-30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2, 30, and/or 55 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, 30, and/or 55, or an epitope of the polypeptide sequence encoded by a polynucleotide sequence contained in ATCC Deposit No:Z or encoded by a polynucleotide that hybridizes to the complement of the sequence of SEQ ID NO:1, 29, and/or 54 or contained in ATCC Deposit No:Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1, 29, and/or 54 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, 30, and/or 55, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multi-specific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$M, $5 \times 10^{-15}$ M, or $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem . . . 272(17):11295-11301 (1997); Taryman et al., Neuron 14(4):755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the HGPRBMY11 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an HGPRBMY11 polypeptide or, more preferably, with a HGPRBMY11 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225-232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240: 1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807, 715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522-525 (1986); Reichmann et al., Nature, 332:323-327 (1988); Verhoeyen et al., Science, 239: 1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature 332:323-329 (1988) and Presta, Curr. Op. Struct. Biol., 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779-783 (1992); Lonberg et al., Nature 368:856-859 (1994); Fishwild et al., Nature Biotechnol., 14:845-51 (1996); Neuberger, Nature Biotechnol., 14:826 (1996); Lonberg and Huszer, Intern. Rev. Immunol., 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the HGPRBMY11 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HUV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, 30, and/or 55.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRS) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5 K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem . . . 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media; and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2, 30, and/or 55 may be fused or conjugated to the above antibody portions to increase the in vivo half life of the polypeptides or for use in immunoassays using methods known in the art. Further, the polypeptides corresponding to SEQ ID NO:2, 30, and/or 55 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270: 9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760-5, (2001); Dickert, F, L., Hayden, O., Halikias, K, P, Analyst., 126(6):766-71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179-85, (2001); Jenkins, A, L., Yin, R., Jensen, J. L, Analyst., 126(6):798-802, (2001); Jenkins, A, L., Yin, R., Jensen, J. L, Analyst., 126(6): 798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795-802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072-3, (2001); and Quaglia, M., Chenon, K., Hall, A, J., De, Lorenzi, E., Sellergren, B, J. Am. Chem, Soc., 123(10): 2146-54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp147-158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions, particularly Crohn's disease. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming any of the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331:84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3-22 (1995)). For example, the c-myc tag and the 8F9, 3C7, 6E10, G4m B7 and 9E10 antibodies thereto (Evan et al., Molecular and Cellular Biology 5:3610-3616 (1985)); the Herpes Simplex virus glycoprotein D (gD) tag and its antibody (Paborsky et al., Protein Engineering, 3(6): 547-553 (1990), the Flag-peptide—i.e., the octapeptide sequence DYKDDDDK (SEQ ID NO:2, 30, and/or 558), (Hopp et al., Biotech. 6:1204-1210 (1988); the KT3 epitope peptide (Martin et al., Science, 255:192-194 (1992)); a-tubulin epitope peptide (Skinner et al., J. Biol. Chem., 266:15136-15166, (1991)); the T7 gene 10 protein peptide tag (Lutz-Freyermuth et al., Proc. Natl. Sci. USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999; 886:233-5), or HC toxin (Tonukari N.J., et al., Plant Cell. 2000 February;12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express the polypeptide of the present invention in a eukaryotic system. Pichia pastoris is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111-21 (1985); Koutz, P. J, et al., Yeast 5:167-77 (1989); Tschopp, J. F., et al., Nucl. Acids Res. 15:3859-76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat.

No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group.

Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 30, and/or 55 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1, 29, and/or 54. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1, 29, and/or 54 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_{.sub.m}$) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; and (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, antiinflammatory proteins (See for example, Mutat. Res. 400(1-2):447-55 (1998), Med Hypotheses.50(5):423-33 (1998), Chem. Biol. Interact. Apr 24; 111-112:23-34 (1998), J Mol Med.76(6):402-12 (1998), Int. J. Tissue React. 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231: 125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., Cell 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., Biotech. 9:630-634 (1991); Folkman et al., N. Engl. J. Med., 333:1757-1763 (1995); Auerbach et al., J. Microvasc. Res. 29:401-411 (1985); Folkman, Advances in Cancer Research, eds. Klein and Weinhouse, Academic Press, New York, pp. 175-203 (1985); Patz, Am. J. Opthalmol. 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442-447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704-710 (1978) and Gartner et al., Surv. Ophthal. 22:291-312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/ or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human HGPRBMY11 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a HGPRBMY11 polypeptide, or a bindable peptide fragment, of this invention, comprising providing a plurality of compounds, combining the HGPRBMY11 polypeptide, or a bindable peptide fragment, with each of a plurality of compounds for a time sufficient to allow binding under suitable conditions and detecting binding of the HGPRBMY11 polypeptide or peptide to each of the plurality of test compounds, thereby identifying the compounds that specifically bind to the HGPRBMY11 polypeptide or peptide.

Methods of identifying compounds that modulate the activity of the novel human HGPRBMY11 polypeptides and/or peptides are provided by the present invention and comprise combining a potential or candidate compound or drug modulator of G-protein coupled receptor biological activity with an HGPRBMY11 polypeptide or peptide, for example, the HGPRBMY11 amino acid sequence as set forth in SEQ ID NO:2, and measuring an effect of the candidate compound or drug modulator on the biological activity of the HGPRBMY11 polypeptide or peptide. Such measurable effects include, for example, physical binding interaction; the ability to cleave a suitable G-protein coupled receptor substrate; effects on native and cloned HGPRBMY11-expressing cell line; and effects of modulators or other G-protein coupled receptor-mediated physiological measures.

Another method of identifying compounds that modulate the biological activity of the novel HGPRBMY11 polypeptides of the present invention comprises combining a potential or candidate compound or drug modulator of a G-protein coupled receptor biological activity with a host cell that expresses the HGPRBMY11 polypeptide and measuring an effect of the candidate compound or drug modulator on the biological activity of the HGPRBMY11 polypeptide. The host cell can also be capable of being induced to express the HGPRBMY11 polypeptide, e.g., via inducible expression. Physiological effects of a given modulator candidate on the HGPRBMY11 polypeptide can also be measured. Thus, cellular assays for particular G-protein coupled receptor modulators may be either direct measurement or quantification of the physical biological activity of the HGPRBMY11 polypeptide, or they may be measurement or quantification of a physiological effect. Such methods preferably employ a HGPRBMY11 polypeptide as described herein, or an overexpressed recombinant HGPRBMY11 polypeptide in suitable host cells containing an expression vector as described herein, wherein the HGPRBMY11 polypeptide is expressed, overexpressed, or undergoes upregulated expression.

Another aspect of the present invention embraces a method of screening for a compound that is capable of modulating the biological activity of a HGPRBMY11 polypeptide, comprising providing a host cell containing an expression vector harboring a nucleic acid sequence encoding a HGPRBMY11 polypeptide, or a functional peptide or portion thereof (e.g., SEQ ID NOS:2); determining the biological activity of the expressed HGPRBMY11 polypeptide in the absence of a modulator compound; contacting the cell with the modulator compound and determining the biological activity of the expressed HGPRBMY11 polypeptide in the presence of the modulator compound. In such a method, a difference between the activity of the HGPRBMY11 polypeptide in the presence of the modulator compound and in the absence of the modulator compound indicates a modulating effect of the compound.

Essentially any chemical compound can be employed as a potential modulator or ligand in the assays according to the present invention. Compounds tested as G-protein coupled receptor modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel HGPRBMY11 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept Prot. Res.*, 37:487-493; and Houghton et al., 1991, *Nature*, 354:84-88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909-6913), vinylogous polypeptides (Hagihara et al., 1992, *J. Amer. Chem. Soc.*, 114:6568), non-peptidal peptidomimetics with glucose scaffolding (Hirschmann et al., 1992, *J. Amer. Chem. Soc.*, 114:9217-9218), analogous organic synthesis of small compound libraries (Chen et al., 1994, *J. Amer. Chem. Soc.*, 116:2661), oligocarbamates (Cho et al., 1993, *Science*, 261:1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309-314) and PCT/US96/10287), carbohydrate libraries (e.g., Liang et al., 1996, *Science*, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a HGPRBMY11 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a HGPRBMY11 polypeptide or peptide to measure a biological binding or ligand binding activity, the source may be a whole cell lysate that can be prepared by successive freeze-thaw cycles (e.g., one to three) in the presence of standard protease inhibitors. The HGPRBMY11 polypeptide may be partially or completely purified by standard protein purification methods, e.g., affinity chromatography using specific antibody described infra, or by ligands specific for an epitope tag engineered into the recombinant HGPRBMY11 polypeptide molecule, also as described herein. Binding activity can then be measured as described.

Compounds which are identified according to the methods provided herein, and which modulate or regulate the biological activity or physiology of the HGPRBMY11 polypeptides according to the present invention are a preferred embodiment of this invention. It is contemplated that such modulatory compounds may be employed in treatment and therapeutic methods for treating a condition that is mediated by the novel HGPRBMY11 polypeptides by administering to an individual in need of such treatment a therapeutically effective amount of the compound identified by the methods described herein.

In addition, the present invention provides methods for treating an individual in need of such treatment for a disease, disorder, or condition that is mediated by the HGPRBMY11 polypeptides of the invention, comprising administering to the individual a therapeutically effective amount of the HGPRBMY11-modulating compound identified by a method provided herein.

Having generally described the invention, the same will be more readily understood by reference to the following examples, which are provided by way of illustration and are not intended as limiting.

REFERENCES

F Horn, G Vriend. G protein-coupled receptors in silico. J. Mol. Med. 76: 464-468, 1998.

Y Feng, C C Broder, P E Kennedy, E A Berger. HIV-1 entry cofactor: functional cDNA cloning of a seven-transmembrane, G protein-coupled receptor. Science 272:872-877, 1996

F Horn, R Bywater, G Krause, W Kuipers, L Oliveira, A C M Paiva, C Sander, G Vriend. The interaction of class B G protein-coupled receptors and their hormones. Receptors and Channels 5:305-314, 1998

S F Altschul, T L Madden, A A Schaffer, J Zhang, Z Zhang, W Miller, D J Lipman. Gapped BLAST and PSI-BLAST: a new generation of protein database search programs. Nucleic Acids Res 25:3389-3402, 1997.

K Hofmann, W Stoffel. TMbase—A database of membrane spanning proteins segments. Biol. Chem. Hoppe-Seyler 347:166, 1993.

EXAMPLES

Description of the Preferred Embodiments

Example 1

Bioinformatics Analysis

G-protein coupled receptor sequences were used as probes to search the human genomic sequence database. The search program used was gapped BLAST (S F Altschul, T L Madden, A A Schaffer, J Zhang, Z Zhang, W Miller, D J Lipman., Nucleic Acids Res 25:3389-3402, 1997). The top genomic exon hits from the BLAST results were searched back against the non-redundant protein and patent sequence databases. From this analysis, exons encoding potential novel GPCRs were identified based on sequence homology. Also, the genomic region surrounding the matching exons were analyzed. Based on this analysis, potential full-length sequence of a novel human GPCR, HGPRBMY11, was identified directly from the genomic sequence (BAC AL137118; Genbank Accession No. AL137118). The full-length clone of this GPCR was experimentally obtained using the sequence from genomic data to design cloning primers (see Example 2). The complete protein sequence of HGPRBMY11 was analyzed for potential transmembrane domains. TMPRED program (K Hofmann, W Stoffel, Biol. Chem. Hoppe-Seyler 347:166, 1993.) was used for transmembrane prediction. The program predicted seven transmembrane domains and the predicted domains match with the predicted transmembrane domains of related GPCRs at the sequence level. Based on the sequence, structure, and known GPCR signature sequences, the orphan protein, HGPRBMY11, has been determined to represent a novel human GPCR.

The HGPRBMY11 splice variant, HGPRBMY11v1, was identified based upon further inspection of the BAC AL137118 genomic sequence in comparison with the sequence of the cloned HGPRBMY11 gene (SEQ ID NO:29). Specifically, it was determined that the sequence 5' of the HGPRBMY11 encoding sequence (SEQ ID NO:1), incorrectly contained an additional nucleotide that prematurely truncated the open reading frame (ORF). Upon deletion of this nucleotide, the ORF was found to extend further in the 5' direction resulting in the full-length sequence of HGORBMY11 (SEQ ID NO:29). Comparison of the resulting encoded polypeptide, referred to as HGPRBMY11v1 (SEQ ID NO:30), to other GPCR homologues revealed several conserved amino acids within this extended region (see FIGS. 2A-B). As a result, the HGPRBMY11v1 polypeptide, in addition to its encoding polynucleotide, are believed to represent the physiologically relevant form of the HGPRBMY11 gene.

Example 2

Cloning of the Novel Human HGPRBMY11 G-Protein Coupled Receptor

Using the predict exon genomic sequence from bac AL137118, an antisense 80 bp oligo with biotin on the 5' end was designed with the following sequence:

```
                                          (SEQ ID NO:9)
5'bTTGGGAAATGGGTTGTCCATATATGTTTTCCTGCAGCCTTATAAGA

AGTCCACATCTGTGAACGTTTTCATGCTAAATCT -3'
```

One microliter (one hundred and fifty nanograms) of the biotinylated oligo was added to six microliters (six micrograms) of a mixture of single-stranded covalently closed circular liver, brain and testis cDNA libraries (These libraries are commercially available from Life Technologies, Rockville, Md.) and seven microliters of 100% formamide in a 0.5 ml PCR tube. The mixture was heated in a thermal cycler to 95° C. for 2 mins. Fourteen microliters of 2× hybridization buffer (50% formamide, 1.5 M NaCl, 0.04 M NaPO$_4$, pH 7.2, 5 mM EDTA, 0.2% SDS) was added to the heated probe/cDNA library mixture and incubated at 42° C. for 26 hours. Hybrids between the biotinylated oligo and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1×SSPE, 0.1% SDS at 45° C.

The single stranded cDNAs were release from the biotinlyated oligo/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspend in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10×PCR buffer. The mixture was heated to 95° C. for 20 seconds, then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitate and resuspended in 10 microliters of TE. Two microliters were electroporated in *E. coli* DH12S cells and resulting colonies were screen by PCR, using a primer pair designed from the genomic exonic sequence to identify the proper cDNAs.

Oligos used to identity the cDNAs by PCR:

```
AL137118-L1  GGCCATTTCAGATCTGCTGT    (SEQ ID NO:10)

AL137118-R1  CTGAAGGGAAGCGTGCTTAT    (SEQ ID NO:11)
```

Those cDNA clones that were positive by PCR had the inserts sized and two clones were chosen for DNA sequencing. Both clones had identical sequence.

The full-length nucleotide sequence and the encoded polypeptide for HGPRBMY11 is shown in FIGS. 1A-B. The sequence was analyzed and plotted in a hydrophobicity plot showing the seven transmembrane domains characterisitic of G-protein coupled receptors (see FIG. 3).

Example 3

Expression Profiling of the Novel Human HGPRBMY11 Polypeptide

The same PCR primer pair that was used to identify the novel HGPRBMY11 cDNA clones (SEQ ID NO:9 and 10) was used to measure the steady state levels of mRNA by quantitative PCR. Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the novel HGPRBMY11. The PCR data was converted into a relative assessment of the difference in transcript abundance amongst the tissues tested and the data is presented in FIG. 4. Transcripts corresponding to HGPRBMY11 were expressed highly in the lymph node, and to a lesser extent in thumus, small intestine, and spleen.

Example 4

Functional Characterization of the Novel Human GPCR, HGPRBMY11

The use of mammalian cell reporter assays to demonstrate functional coupling of known GPCRs (G Protein Coupled Receptors) has been well documented in the literature (Gilman, 1987, Boss et al., 1996; Alam & Cook, 1990; George et al., 1997; Selbie & Hill, 1998; Rees et al., 1999). In fact, reporter assays have been successfully used for identifying novel small molecule agonists or antagonists against GPCRs as a class of drug targets (Zlokarnik et al., 1998; George et al., 1997; Boss et al., 1996; Rees et al, 2001). In such reporter assays, a promoter is regulated as a direct consequence of activation of specific signal transduction cascades following agonist binding to a GPCR (Alam & Cook 1990; Selbie & Hill, 1998; Boss et al., 1996; George et al., 1997; Gilman, 1987).

A number of response element-based reporter systems have been developed that enable the study of GPCR function. These include cAMP response element (CRE)-based reporter genes for G alpha i/o, G alpha s-coupled GPCRs, Nuclear Factor Activator of Transcription (NFAT)-based reporters for G alpha q/11 or the promiscuous G protein G alpha 15/16-coupled receptors and MAP kinase reporter genes for use in Galpha i/o coupled receptors (Selbie & Hill, 1998; Boss et al., 1996; George et al., 1997; Blahos, et al., 2001; Offermann & Simon, 1995; Gilman, 1987; Rees et al., 2001). Transcriptional response elements that regulate the expression of Beta-Lactamase within a CHO K1 cell line (Cho/NFAT-CRE: Aurora Biosciences™) (Zlokarnik et al., 1998) have been implemented to characterize the function of the orphan HGPRBMY11 polypeptide of the present invention. The system enables demonstration of constitutive G-protein coupling to endogenous cellular signaling components upon intracellular overexpression of orphan receptors. Overexpression has been shown to represent a physiologically relevant event. For example, it has been shown that overexpression occurs in nature during metastatic carcinomas, wherein defective expression of the monocyte chemotactic protein 1 receptor, CCR2, in macrophages is associated with the incidence of human ovarian carcinoma (Sica, et al., 2000; Salcedo et al., 2000). Indeed, it has been shown that overproduction of the Beta 2 Adrenergic Receptor in transgenic mice leads to constitutive activation of the receptor signaling pathway such that these mice exhibit increased cardiac output (Kypson et al., 1999; Dorn et al., 1999). These are only a few of the many examples demonstrating constitutive activation of GPCRs whereby many of these receptors are likely to be in the active, R*, conformation (J. Wess 1997).

Materials and Methods

DNA Constructs

The putative GPCR HGPRBMY11 cDNA was PCR amplified using PFU™ (Stratagene). The primers used in the PCR reaction were specific to the HGPRBMY11 polynucleotide and were ordered from Gibco BRL (5 prime primer:5'-CCGCTAGCGCATGGAAAATGGCACCT-TCAGCAATAA-3' (SEQ ID NO:78), The following 3 prime primer was used to add a Flag-tag epitope to the HGPRBMY11 polypeptide for immunocytochemistry: 5'-CGGCGGCCGCTTATACTCTTGTTTCCTTTC TCAACCA-3'(SEQ ID NO:79). The product from the PCR reaction was isolated from a 0.8% Agarose gel (Invitrogen) and purified using a Gel Extraction Kit™ from Qiagen.

The purified product was then digested overnight along with the pcDNA3.1 Hygro™ mammalian expression vector from Invitrogen using the HindIII and BamHI restriction enzymes (New England Biolabs). These digested products were then purified using the Gel Extraction Kit™ from Qiagen and subsequently ligated to the pcDNA3.1 Hygro™ expression vector using a DNA molar ratio of 4 parts insert: 1 vector. All DNA modification enzymes were purchased from NEB. The ligation was incubated overnight at 16 degrees Celsius, after which time, one microliter of the mix was used to transform DH5 alpha cloning efficiency competent *E. coli*™ (Gibco BRL). A detailed description of the pcDNA3.1 Hygro™ mammalian expression vector is available at the Invitrogen web site (www.Invitrogen.com). The plasmid DNA from the ampicillin resistant clones were isolated using the Wizard DNA Miniprep System™ from Promega. Positive clones were then confirmed and scaled up for purification using the Qiagen Maxiprep™ plasmid DNA purification kit.

Cell Line Generation

The pcDNA3.1hygro vector containing the orphan HGPRBMY11 cDNA were used to transfect Cho/NFAT-CRE, HEK/CRE or the Cho/NFAT G alpha 15 (Aurora Biosciences) cells using Lipofectamine 2000™ according to the manufacturers specifications (Gibco BRL). Two days later, the cells were split 1:3 into selective media (DMEM 11056, 600 ug/ml Hygromycin, 200 ug/mil Zeocin, 10% FBS). All cell culture reagents were purchased from Gibco BRL-Invitrogen.

The Cho/NFAT-CRE or Cho/NFAT G alpha 15 cell lines, transiently or stably transfected with the orphan HGPRBMY11 GPCR, were analyzed using the FACS Vantage SE™ (BD), fluorescence microscopy (Nikon), and the LJL Analyst™ (Molecular Devices). In this system, changes in real-time gene expression, as a consequence of constitutive G-protein coupling of the orphan HGPRBMY11 GPCR, is examined by analyzing the fluorescence emission of the transformed cells at 447 nm and 518 nm. The changes in gene expression can be visualized using Beta-Lactamase as a reporter, that, when induced by the appropriate signaling cascade, hydrolyzes an intracellularly loaded, membrane-permeant ester substrate (CCF2/AM™ Aurora Biosciences; Zlokarnik, et al., 1998). The CCF2/AM™ substrate is a 7-hydroxycoumarin cephalosporin with a fluorescein attached through a stable thioether linkage. Induced expression of the Beta-Lactamase enzyme is readily apparent since each enzyme molecule produced is capable of changing the fluorescence of many CCF2/AM™ substrate molecules. A schematic of this cell based system is shown below.

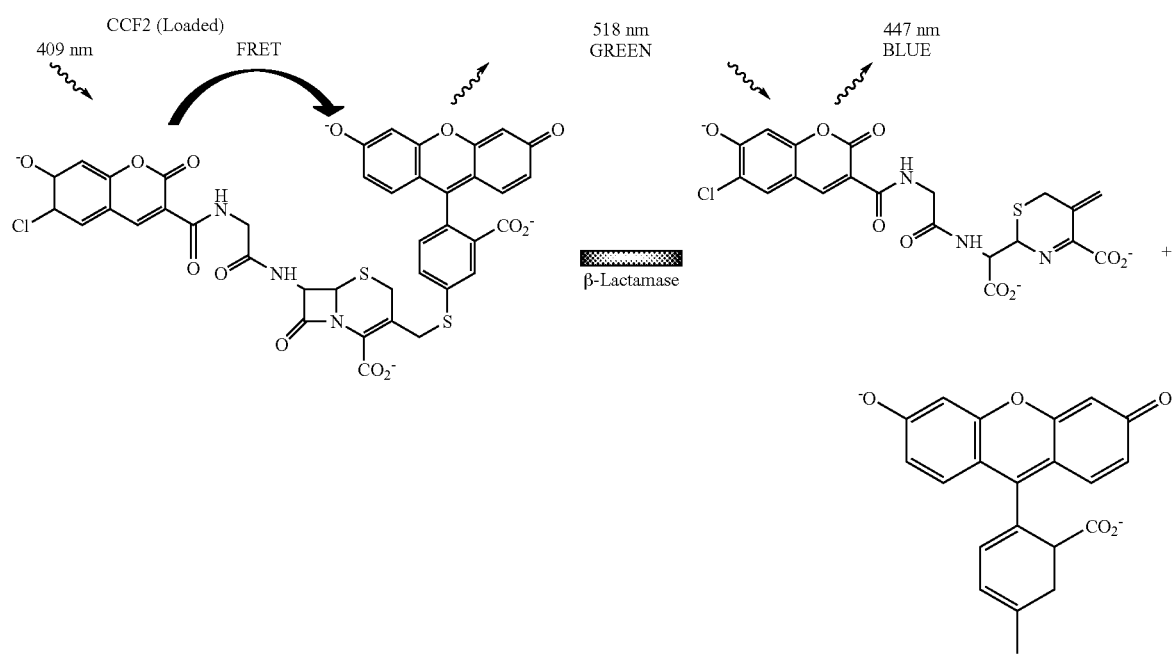

In summary, CCF2/AM™ is a membrane permeant, intracellularly-trapped, fluorescent substrate with a cephalosporin core that links a 7-hydroxycoumarin to a fluorescein. For the intact molecule, excitation of the coumarin at 409 nm results in Fluorescence Resonance Energy Transfer (FRET) to the fluorescein which emits green light at 518 nm. Production of active Beta-Lactamase results in cleavage of the Beta-Lactam ring, leading to disruption of FRET, and excitation of the coumarin only—thus giving rise to blue fluorescent emission at 447 nm.

Fluorescent emissions were detected using a Nikon-TE300 microscope equipped with an excitation filter (D405/10x-25), dichroic reflector (430DCLP), and a barrier filter for dual DAPI/FITC (510 nM) to visually capture changes in Beta-Lactamase expression. The FACS Vantage SE is equiped with a Coherent Enterprise II Argon Laser and a Coherent 302C Krypton laser. In flow cytometry, LV excitation at 351-364 nm from the Argon Laser or violet excitation at 407 nm from the Krypton laser are used. The optical filters on the FACS Vantage SE are HQ460/50m and HQ535/40m bandpass separated by a 490 dichroic mirror.

Prior to analyzing the fluorescent emissions from the cell lines as described above, the cells were loaded with the CCF2/AM substrate. A 6×CCF2/AM loading buffer was prepared whereby 1 mM CCF2/AM (Aurora Biosciences) was dissolved in 100% DMSO (Sigma). 12 ul of this stock solution was added to 60 ul of 100 mg/ml Pluronic F127 (Sigma) in DMSO containing 0.1% Acetic Acid (Sigma). This solution was added while vortexing to 1 mL of Sort Buffer (PBS minus calcium and magnesium-Gibco-25 mM HEPES-Gibco-pH 7.4, 0.1% BSA). Cells were placed in serum-free media and the 6×CCF2/AM was added to a final concentration of 1×. The cells were then loaded at room temperature for one to two hours, and then subjected to fluorescent emission analysis as described herein. Additional details relative to the cell loading methods and/or instrument settings may be found by reference to the following publications: see Zlokarnik, et al., 1998; Whitney et al., 1998; and BD Biosciences, 1999.

Immunocytochemistry

The cell lines transfected and selected for expression of Flag-epitope tagged orphan GPCRs were analyzed by immunocytochemistry. The cells were plated at 1×10^3 in each well of a glass slide (VWR). The cells were rinsed with PBS followed by acid fixation for 30 minutes at room temperature using a mixture of 5% Glacial Acetic Acid/90% ETOH. The cells were then blocked in 2% BSA and 0.1% Triton in PBS, incubated for 2 h at room temperature or overnight at 4° C. A monoclonal anti-Flag FITC antibody was diluted at 1:50 in blocking solution and incubated with the cells for 2 h at room temperature. Cells were then washed three times with 0.1% Triton in PBS for five minutes. The slides were overlayed with mounting media dropwise with Biomedia—Gel Mount™ (Biomedia; Containing Anti-Quenching Agent). Cells were examined at 10× magnification using the Nikon TE300 equiped with FITC filter (535 nm).

Results—HGPRBMY11 Constitutively Activates Gene Expression Through the NFAT/CRE Response Element There is strong evidence that certain GPCRs exhibit a cDNA concentration-dependent constitutive activity through cAMP response element (CRE) luciferase reporters (Chen et al., 1999). In an effort to demonstrate functional coupling of HGPRBMY11 to known GPCR second messenger pathways, the HGPRBMY11 polypeptide was expressed at high constitutive levels in the Cho-NFAT/CRE cell line. To this end, the HGPRBMY11 cDNA was PCR amplified and subcloned into the pcDNA3.1 hygro™ mammalian expression vector as described herein. Early passage Cho-NFAT/CRE cells were then transfected with the resulting pcDNA3.1 hygro™/HGPRBMY11 construct. Transfected and non-transfected Cho-NFAT/CRE cells (control) were loaded with the CCF2 substrate and stimulated with 10 nM PMA, and 1 uM Thapsigargin (NFAT stimulator) or 10 uM Forskolin (CRE stimulator) to fully activate the NFAT/CRE element. The cells were then analyzed for fluorescent emission by FACS.

The FACS profile demonstrates the constitutive activity of HGPRBMY11 in the Cho-NFAT/CRE line as evidenced by the significant population of cells with blue fluorescent emission at 447 nm (see FIG. 8: Blue Cells). As expected, the NFAT/CRE response element in the untransfected control cell line was not activated (i.e., beta lactamase not induced), enabling the CCF2 substrate to remain intact, and resulting in the green fluorescent emission at 518 nM (see FIG. 7-Green Cells). A very low level of leaky Beta Lactamase expression was detectable as evidenced by the small population of cells emitting at 447 nm. Analysis of a stable pool of cells transfected with HGPRBMY11 revealed constitutive coupling of the cell population to the NFAT/CRE response element, activation of Beta Lactamase and cleavage of the substrate (FIG. 8-B*lue* Cells). These results demonstrate that overexpression of HGPRBMY11 leads to constitutive coupling of signaling pathways known to be mediated by Gq/11 or Gs coupled receptors that converge to activate either the NFAT or CRE response elements respectively (Boss et al., 1996; Chen et al., 1999).

To further examine the functional coupling, we examined the ability of HGPRBMY11 to couple to the cAMP response element (CRE) independent of the NFAT response element. To this end, we transfected HEK-CRE cell line that contained only the integrated 3XCRE linked to the Beta-Lactamase reporter. In this stable pool, we found that HGPRBMY11 does not constitutively couple to the cAMP mediated second messenger pathways (FIG. 10). As expected, the CRE response element in the untransfected control cell line was not activated (i.e., beta lactamase not induced), enabling the CCF2 substrate to remain intact, and resulting in the green fluorescent emission at 518 nM (see FIG. 9-Green Cells). Indeed, we have found that known Gs coupled receptors do demonstrate constitutive activation when overexpressed in this cell line. Direct activation of adenylate cyclase using 10 uM Forskolin activates CRE and induces Beta-Lactamase in the HEK-CRE cell line (data not shown). We conclude that HGPRBMY11 is a functional GPCR analogous to known Gq coupled receptors where we find constitutive activation of the NFAT response element. Therefore constitutive expression of HGPRBMY11 in the CHO Nfat/CRE cell line leads to NFAT activation through accumulation of intracellular $Ca^{2+}$ as has been demonstrated for the M3 muscarinic receptor (Boss et al., 1996).

In an effort to further characterize the observed functional coupling of the HGPRBMY11 polypeptide, its ability to couple to a G protein was examined. To this end, the promiscuous G protein, G alpha 15 was utilized. Specific domains of alpha subunits of G proteins have been shown to control coupling to GPCRs (Blahos et al., 2001). It has been shown that the extreme C-terminal 20 amino acids of either G alpha 15 or 16 confer the unique ability of these G proteins to couple to many GPCRs, including those that naturally do not stimulate PLC (Blahos et al., 2001). Indeed, both G alpha 15 and 16 have been shown to couple a wide variety of GPCRs to Phospholipase C activation of calcium mediated signaling pathways (including the NFAT-signaling pathway) (Offermanns & Simon). To demonstrate that HGPRBMY11 was functioning as a GPCR, the Cho-NFAT G alpha 15 cell line that contained only the integrated NFAT response element linked to the Beta-Lactamase reporter was transfected with the pcDNA3.1 hygro™/HGPRBMY11 construct. Analysis of the fluorescence emission from this stable pool showed that HGPRBMY11 constitutively coupled to the NFAT mediated second messenger pathways via G alpha 15 (see FIGS. 11 and 11). In conclusion, the results are consistent with HGPRBMY11 representing a functional GPCR analogous to known G alpha 15 coupled receptors. Therefore, constitutive expression of HGPRBMY11 in the CHO/NFAT G alpha 15 cell line leads to NFAT activation through accumulation of intracellular $Ca^{2+}$.

In preferred embodiments, the HGPRBMY11 polynucleotides and polypeptides, including agonists, antagonists, and fragments thereof, are useful for modulating intracellular $Ca^{2+}$ levels, modulating $Ca^{2+}$ sensitive signaling pathways, and modulating NFAT element associated signaling pathways.

Demonstration of Cellular Expression

HGPRBMY11 was tagged at the C-terminus using the Flag epitope and inserted into the pcDNA3.1 hygro™ expression vector, as described herein. Immunocytochemistry of Cho NFAT G alpha 15 cell lines transfected with the Flag-tagged HGPRBMY11 construct with FITC conjugated Anti Flag monoclonal antibody demonstrated that HGPRBMY11 is indeed expressed in these cells. Briefly, Cho NFAT G alpha 15 cell lines were transfected with pcDNA3.1 hygro™/HGPRBMY11-Flag vector, fixed with 70% methanol, and permeablized with 0.1% TritonX100. The cells were then blocked with 1% Serum and incubated with a FITC conjugated Anti Flag monoclonal antibody at 1:50 dilution in PBS-Triton. The cells were then washed several times with PBS-Triton, overlayed with mounting solution, and fluorescent images were captured (see FIG. 13). The control cell line, non-transfected ChoNFAT G alpha 15 cell line, exhibited no detectable background fluorescence (FIG. 13). The HGPRBMY11-FLAG tagged expressing Cho NFAT G alpha 15 line exhibited cell specific expression as indicated (FIG. 13). These data provide clear evidence that HGPRBMY11 is expressed in these cells.

Screening Paradigm

The Aurora Beta-Lactamase technology provides a clear path for identifying agonists and antagonists of the HGPRBMY11 polypeptide. Cell lines that exhibit a range of constitutive coupling activity have been identified by sorting through HGPRBMY11 transfected cell lines using the FACS Vantage SE (see FIG. 14). For example, cell lines have been sorted that have an intermediate level of orphan GPCR expression, which also correlates with an intermediate coupling response, using the LJL analyst. Such cell lines will provide the opportunity to screen, indirectly, for both agonists and antagonists of HGPRBMY11 by looking for inhibitors that block the beta lactamase response, or agonists that increase the beta lactamase response. As described herein, modulating the expression level of beta lactamase directly correlates with the level of cleaved CCR2 substrate. For example, this screening paradigm has been shown to work for the identification of modulators of a known GPCR, 5HT6, that couples through Adenylate Cyclase, in addition to, the identification of modulators of the 5HT2c GPCR, that couples through changes in $[Ca^{2+}]i$. The data shown below represent cell lines that have been engineered with the desired pattern of HGPRBMY11 expression to enable the identification of potent small molecule agonists and antagonists. HGPRBMY11 modulator screens may be carried out using a variety of high throughput methods known in the art, though preferably using the fully automated Aurora UHTSS system. The uninduced, orphan-transfected Cho NFAT-CRE cell line represents the relative background level of beta lactamase expression (FIG. 14; panel a). Following treatment with a cocktail of 10 nM Forskolin, 1 uM Thapsigargin, and 100 nM PMA (FIG. 14; F/T/P; panel b), the cells fully activate the CRE-NFAT response element demonstrating the dynamic range of the assay. Panel C (FIG. 14) represents an orphan transfected Cho NFAT-CRE cell line that shows an intermediate level of beta lactamase expression post F/T/P stimulation, while panel D (FIG. 14) represents an orphan transfected Cho NFAT-CRE cell line that shows a high level of beta lactamase expression post F/T/P stimulation.

In preferred embodiments, the HGPRBMY11 transfected Cho NFAT-CRE cell lines of the present invention are useful for the identification of agonists and antagonists of the HGPRBMY11 polypeptide. Representative uses of these cell lines would be their inclusion in a method of identifying HGPRBMY11 agonists and antagonists. Preferably, the cell lines are useful in a method for identifying a compound that modulates the biological activity of the HGPRBMY11 polypeptide, comprising the steps of (a) combining a candidate modulator compound with a host cell expressing the HGPRBMY11 polypeptide having the sequence as set forth in SEQ ID NO:2; and (b) measuring an effect of the candidate modulator compound on the activity of the expressed HGPRBMY11 polypeptide. Representative vectors expressing the HGPRBMY11 polypeptide are referenced herein (e.g., pcDNA3.1 hygro™) or otherwise known in the art.

The cell lines are also useful in a method of screening for a compounds that is capable of modulating the biological activity of HGPRBMY11 polypeptide, comprising the steps of: (a) determining the biological activity of the HGPRBMY11 polypeptide in the absence of a modulator compound; (b) contacting a host cell expression the HGPRBMY11 polypeptide with the modulator compound; and (c) determining the biological activity of the HGPRBMY11 polypeptide in the presence of the modulator compound; wherein a difference between the activity of the HGPRBMY11 polypeptide in the presence of the modulator compound and in the absence of the modulator compound indicates a modulating effect of the compound. Additional uses for these cell lines are described herein or otherwise known in the art.

1. Rees, S., Brown, S., Stables, J.: Reporter gene systems for the study of G Protein Coupled Receptor signalling in mammalian cells. In Milligan G. (ed.): Signal Transduction: A practical approach. Oxford: Oxford University Press, 1999: 171-221.

2. Alam, J., Cook, J. L.: Reporter Genes: Application to the study of mammalian gene transcription. Anal. Biochem. 1990; 188: 245-254.

3. Selbie, L. A. and Hill, S. J.: G protein-coupled receptor cross-talk: The fine-tuning of multiple receptor-signaling pathways. TiPs. 1998; 19: 87-93.

4. Boss, V., Talpade, D. J., and Murphy, T. J.: Induction of NFAT mediated transcription by Gq-coupled Receptors in lympoid and non-lymphoid cells. JBC. 1996; 271: 10429-10432.

5. George, S. E., Bungay, B. J., and Naylor, L. H.: Functional coupling of endogenous serotonin (5-HT1B) and calcitonin (C1a) receptors in Cho cells to a cyclic AMP-responsive luciferase reporter gene. J. Neurochem. 1997; 69: 1278-1285.

6. Suto, C M, Igna D M: Selection of an optimal reporter for cell-based high throughput screening assays. J. Biomol. Screening. 1997; 2: 7-12.

7. Zlokarnik, G., Negulescu, P. A., Knapp, T. E., More, L., Burres, N., Feng, L., Whitney, M., Roemer, K., and Tsien, R. Y. Quantitation of transcription and clonal selection of single living cells with a B-Lactamase Reporter. Science. 1998; 279: 84-88.

8. S. Fiering et. al., Genes Dev. 4, 1823 (1990).

9. J. Karttunen and N. Shastri, PNAS 88, 3972 (1991).

10. Hawes, B. E., Luttrell. L. M., van Biesen, T., and Lefkowitz, R. J. (1996) JBC 271, 12133-12136.

11. Gilman, A. G. (1987) Annul. Rev. Biochem. 56, 615-649.

12. Maniatis et al., Cold Spring Harbor Press, 1989.

13. Salcedo, R., Ponce, M. L., Young, H. A., Wasserman, K., Ward, J. M., Kleinman, H. K., Oppenheim, J. J., Murphy, W. J. Human endothelial cells express CCR2 and respond to MCP-1: direct role of MCP-1 in angiogenesis and tumor progression. Blood. 2000; 96 (1): 3440.

14. Sica, A., Saccani, A., Bottazzi, B., Bernasconi, S., Allavena, P., Gaetano, B., LaRossa, G., Scotton, C., Balkwill F., Mantovani, A. Defective expression of the monocyte chemotactic protein 1 receptor CCR2 in macrophages associated with human ovarian carcinoma. J. Immunology. 2000; 164: 733-8.

15. Kypson, A., Hendrickson, S., Akhter, S., Wilson, K., McDonald, P., Lilly, R., Dolber, P., Glower, D., Lefkowitz, R., Koch, W. Adenovirus-mediated gene transfer of the B2 AR to donor hearts enhances cardiac function. Gene Therapy. 1999; 6: 1298-304.

16. Dorn, G. W., Tepe, N. M., Lorenz, J. N., Kock, W. J., Ligget, S. B. Low and high level transgenic expression of B2AR differentially affect cardiac hypertrophy and function in Galpha q-overexpressing mice. PNAS. 1999; 96: 6400-5.

17. J. Wess. G protein coupled receptor: molecular mechanisms involved in receptor activation and selectivity of G-protein recognition.

18. Whitney, M, Rockenstein, E, Cantin, G., Knapp, T., Zlokarnik, G., Sanders, P., Durick, K., Craig, F. F., and Negulescu, P. A. A genome-wide functional assay of signal transduction in living mammalian cells. 1998. Nature Biotech. 16: 1329-1333.

19. BD Biosciences: FACS Vantage SE Training Manual. Part Number 11-11020-00 Rev. A. August 1999.

20. Chen, G., Jaywickreme, C., Way, J., Armour S., Queen K., Watson., C., Ignar, D., Chen, W. J., Kenakin, T. Constitutive Receptor systems for drug discovery. J. Pharmacol. Toxicol. Methods 1999; 42: 199-206.

21. Blahos, J., Fischer, T., Brabet, I., Stauffer, D., Rovelli, G., Bockaert, J., and Pin, J.-P. A novel Site on the G alpha-protein that Rocognized Heptahelical Receptors. J. Biol. Chem. 2001; 275, No. 5, 3262-69.

22. Offermanns, S. & Simon, M. I. G alpha 15 and G alpha 16 Couple a Wide Variety of Receptors to Phospholipase C. J. Biol. Chem. 1995; 270, No. 25, 15175-80.

Example 5

Method of Assessing the Expression Profile of the Novel HGPRBMY11 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For HGPRBMY11, the primer probe sequences were as follows:

```
Forward Primer
5'-TTTATTTCCTGACCGTGCTGAGT -3'      (SEQ ID NO:82)

Reverse Primer
5'-GACATGGAGAAGCCGAAAGG -3'         (SEQ ID NO:83)

TaqMan Probe
5'-TGAACCATTGCCAGGAAACGCACAA -3'    (SEQ ID NO:84)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription Reaction and Sequence Detection 100 ng of Dnase-treated total RNA was annealed to 2.5 uM of the respective gene-specific reverse primer in the presence of 5.5 mM Magnesium Chloride by heating the sample to 72° C. for 2 min and then cooling to 55° C. for 30 min. 1.25 U/ul of MuLv reverse transcriptase and 500 uM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 uM forward and reverse primers, 2.0 uM of the TaqMan probe, 500 uM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$.

The expanded expression profile of the HGRBMY11 polypeptide is provided in FIG. 16 and described elsewhere herein.

An expanded expression profile of the HGRBMY11 polypeptide in normal and active Crohn's disease colon tissue is provided in FIG. 18 and described elsewhere herein.

Example 6

Method of Assessing the Expression Profile of the Novel HGPRBMY11 Polypeptides of the Present Invention in a Variety of Cancer Cell Lines RNA quantification may be performed using the SYBR green real-time-PCR fluorogenic assay. RT-PCR is one of the most precise methods for assaying the concentration of nucleic acid templates. PCR primer pairs were designed to the specific gene and used to measure the steady state levels of mRNA by quantitative PCR across a panel of RNA's isolated from proliferative cell lines.

All cell lines were grown using standard conditions: RPMI 1640 supplemented with 10% fetal bovine serum, 100 IU/ml penicillin, 100 mg/ml streptomycin, and 2 mM L-glutamine, 10 mM Hepes (all from GibcoBRL; Rockville, Md.). Eighty percent confluent cells were washed twice with phosphate-buffered saline (GibcoBRL) and harvested using 0.25% trypsin (GibcoBRL). RNA was prepared using the RNeasy Maxi Kit from Qiagen (Valencia, Calif.).

Briefly, first strand cDNA was made from several cell line RNA's and subjected to real time quantitative PCR using a PE 7900HT instrument (Applied Biosystems, Foster City, Calif.) which detects the amount of DNA amplified during each cycle by the fluorescent output of SYBR green, a DNA binding dye specific for double stranded DNA. The specificity of the primer pairs for their targets is verified by performing a thermal denaturation profile at the end of the run which gives an indication of the number of different DNA sequences present by determining melting temperature of double stranded amplicon(s). In the experiment, only one DNA fragment of the correct Tm was detected, having a homogeneous melting point.

Small variations in the amount of cDNA used in each tube was determined by performing parallel experiments using a primer pair for a gene expressed in equal amounts in all tissues, cyclophilin. These data were used to normalize the data obtained with the gene specific primer pairs. The PCR data was converted into a relative assessment of the difference in transcript abundance amongst the tissues tested and the data are presented in bar graph form for each transcript.

The formula for calculating the relative abundance is:

$$\text{Relative abundance} = 2^{-\Delta\Delta Ct}$$

Where $\Delta\Delta Ct$=(The Ct of the sample–the Ct for cyclophilin)– the Ct for a calibrator sample The calibrator sample is arbitrarily chosen as the tissue with the lowest abundance.

For each PCR reaction 10 uL of 2× SybrGreen Master Mix (PE Biosystems) was combined with 4.9 uL water, 0.05 uL of each PCR primer (at 100 uM concentration) and 5 uL of template DNA. The PCR reactions used the following conditions:

95° C. for 10 minutes, then 40 cycles of
95° C. for 30 seconds followed by 60° C. for 1 minute then the thermal denaturation protocol was begun at 60° C. and the flourescence measured as the temperature increased slowly to 95° C.

The sequence of the PCR primers were as follows:

```
Forward Primer
5'-CCATCCATCTCCGTATCAGA -3'     (SEQ ID NO:85)

Reverse Primer
5'-GACAACCCATTTCCCAAGAC -3'     (SEQ ID NO:86)
```

The 'Graph #' of Table IV corresponds to the tissue type position number of FIG. 17. Each cell line listed below represents a cancer cell line. The "Tissue" column provides the tissue source from which the cell line derives.

TABLE IV

| Graph # | Name | Tissue | Fold Difference |
|---|---|---|---|
| 1 | A-427 | lung | 1.89 |
| 2 | A-431 | squamous | 7.47 |
| 3 | A2780/DDP-S | ovarian | 89674.02 |
| 4 | A2780/DDP-R | ovarian | 17.90 |
| 5 | HCT116/epo5 | colon | 17.92 |
| 6 | A2780/TAX-R | ovarian | 440.17 |
| 7 | A2780/TAX-S | ovarian | 247.84 |
| 8 | A549 | lung | 14.31 |
| 9 | AIN4/myc | breast | 3.84 |
| 10 | AIN4T | breast | 1.84 |
| 11 | AIN4 | breast | 5.08 |
| 12 | BT-549 | breast | 2.76 |
| 13 | BT-20 | breast | 1.78 |
| 14 | C-33A | cervical | 7.31 |
| 15 | CACO-2 | colon | 5.16 |
| 16 | Calu-3 | lung | 28.95 |
| 17 | Calu-6 | lung | 17.25 |
| 18 | BT-474 | breast | 3.29 |
| 19 | CCRF-CEM | leukemia | 25.50 |
| 20 | ChaGo-K-1 | lung | 4.46 |
| 21 | DU4475 | breast | 39.26 |
| 22 | ES-2 | ovarian | 13.42 |
| 23 | H3396 | breast | 2.79 |
| 24 | HBL100 | breast | 127.87 |
| 25 | HCT116/VM46 | colon | 3.24 |
| 26 | HCT116/VP35 | colon | 3.35 |
| 27 | HCT116 | colon | 2.15 |
| 28 | A2780/epo5 | ovarian | 2268.92 |
| 29 | HCT116/ras | colon | 2.25 |
| 30 | HCT116/TX15CR | colon | 5.28 |
| 31 | HT-29 | colon | 5.06 |
| 32 | HeLa | cervical | 656.71 |
| 33 | MCF7/Her2 | breast | 6.11 |
| 34 | HL-60 | leukemia | 740.04 |
| 35 | HOC-76 | ovarian | 4.45 |
| 36 | Hs 294T | melanoma | 16.67 |
| 37 | HCT116/vivo | colon | 2.80 |
| 38 | HT-3 | cervical | 108.48 |
| 39 | K-562 | leukemia | 7.36 |
| 40 | SiHa | cervical | 31.96 |
| 41 | LS 174T | colon | 4.02 |
| 42 | LX-1 | lung | 4.44 |
| 43 | MCF7 | breast | 4.35 |
| 44 | MCF-7/AdrR | breast | 6.45 |
| 45 | MDA-MB-175-VII | breast | 9.77 |
| 46 | MDA-MB-231 | breast | 4.83 |
| 47 | ME-180 | cervical | 9.24 |
| 48 | SK-CO-1 | colon | 8.73 |
| 49 | LoVo | colon | 3.69 |

TABLE IV-continued

| Graph # | Name | Tissue | Fold Difference |
|---|---|---|---|
| 50 | SHP-77 | lung | 12.03 |
| 51 | DMS 114 | lung | 41540.92 |
| 52 | Sk-LU-1 | lung | 23.04 |
| 53 | SK-MES-1 | lung | 125.09 |
| 54 | SW1573 | lung | 6.72 |
| 55 | SW626 | ovarian | 3.62 |
| 56 | SW1271 | lung | 9.58 |
| 57 | SW756 | cervical | 61.73 |
| 58 | SW900 | lung | 15.01 |
| 59 | Colo201 | colon | 8.13 |
| 60 | PC-3 | prostate | 6.03 |
| 61 | OVCAR-3 | ovarian | 6.40 |
| 62 | SW480 | colon | 2.46 |
| 63 | SW620 | colon | 3.65 |
| 64 | PA-1 | ovarian | 1.00 |
| 65 | Caov-3 | ovarian | 6.04 |
| 66 | Ca Ski | cervical | 5.81 |
| 67 | HUVEC | endothelial | 27.96 |
| 68 | Jurkat | leukemia | 140.52 |
| 69 | HS804.SK | skin | 10.97 |
| 70 | WM373 | melanoma | 22.91 |
| 71 | WM852 | melanoma | 6.13 |
| 72 | NCI-N87 | gastric | 13.71 |
| 73 | RPMI-2650 | SCC | 44.14 |
| 74 | SCC-15 | SCC | 10.03 |
| 75 | SCC-4 | SCC | 5.45 |
| 76 | SCC-25 | SCC | 4.72 |
| 77 | SCC-9 | SCC | 10.98 |
| 78 | G-361 | melanoma | 1006.54 |
| 79 | C32 | melanoma | 16.65 |
| 80 | SK-MEL-1 | melanoma | 104.04 |
| 81 | SK-MEL-28 | melanoma | 132.75 |
| 82 | SK-MEL-5 | melanoma | 22531.12 |
| 83 | SK-MEL-3 | melanoma | 297.95 |
| 84 | CA-HPV-10 | prostate | 10.19 |
| 85 | 22Rv1 | prostate | 10.62 |
| 86 | LNCaP-FGC | prostate | 4.49 |
| 87 | RWPE-1 | prostate | 4.87 |
| 88 | RWPE-2 | prostate | 49.65 |
| 89 | PWR-1E | prostate | 14.37 |
| 90 | DU 145 | prostate | 11.78 |
| 91 | TOTAL RNA, FETAL LUNG | lung fetal | 627.01 |
| 92 | TOTAL RNA, OVARY | ovarian | 1046.88 |

Prior expression analysis of HGPRBMY11 transcripts determined that this GPCR was expressed in tissues of the female reproductive tract, specifcally in fallopian tube (see FIG. 16). Analysis of expression in several tumor cell lines serves to confirm and extend these claims. A pattern emerges where expression seems to be aberrant, in some cases very high, and some cases very low, in cell lines of ovarian and cervical tumor origin, as shown in Table V. The data from Table V represents the results of a second experiment using a subset of the cell lines provided in Table IV herein. As observed, the fold difference between the results obtained in Table IV and V are relatively similar and confirms other observations disclosed herein.

TABLE V

| Cell Line | Tissue Origin | Fold Difference from control |
|---|---|---|
| C-33A | Cervical | 7.55 |
| Ca Ski | Cervical | 31.12 |
| HeLa | Cervical | 854.83 |
| HT-3 | Cervical | 114.06 |
| ME-180 | Cervical | 8.78 |
| SiHa | Cervical | 27.09 |
| SW756 | Cervical | 7.21 |
| A2780/DDP-R | Ovarian | 8.72 |
| A2780/DDP-S | Ovarian | 77143.98 |
| A2780/epo5 | Ovarian | 1339.99 |

TABLE V-continued

| Cell Line | Tissue Origin | Fold Difference from control |
|---|---|---|
| A2780/TAX-R | Ovarian | 285.38 |
| A2780/TAX-S | Ovarian | 169.22 |
| Caov-3 | Ovarian | 3.56 |
| ES-2 | Ovarian | 7.54 |
| HOC-76 | Ovarian | 6.87 |
| OVCAR-3 | Ovarian | 6.31 |
| PA-1 | Ovarian | 1.00 |
| SW626 | Ovarian | 3.11 |
| Normal Ovary | Ovarian | 927.68 |

Example 7

Complementary Polynucleotides

Antisense molecules or nucleic acid sequences complementary to the HGPRBMY11 protein-encoding sequence, or any part thereof, was used to decrease or to inhibit the expression of naturally occurring HGPRBMY11. Although the use of antisense or complementary oligonucleotides comprising about 15 to 35 base-pairs is described, essentially the same procedure is used with smaller or larger nucleic acid sequence fragments. An oligonucleotide based on the coding sequence of HGPRBMY11 protein, as shown in FIGS. 1A-B, or as depicted in SEQ ID NO:1, for example, is used to inhibit expression of naturally occurring HGPRBMY11. The complementary oligonucleotide is typically designed from the most unique 5' sequence and is used either to inhibit transcription by preventing promoter binding to the coding sequence, or to inhibit translation by preventing the ribosome from binding to the HGPRBMY11 protein-encoding transcript, among others. However, other regions may also be targeted.

Using an appropriate portion of a 5' sequence of SEQ ID NO:1, an effective antisense oligonucleotide includes any of about 15-35 nucleotides spanning the region which translates into the signal or 5' coding sequence, among other regions, of the polypeptide as shown in FIGS. 1A-B (SEQ ID NO:2). Appropriate oligonucleotides are designed using OLIGO 4.06 software and the HGPRBMY11 protein coding sequence (SEQ ID NO:1). Preferred oligonucleotides are deoxynucleotide, or chimeric deoxynucleotide/ribonucleotide based and are provided below. The oligonucleotides were synthesized using chemistry essentially as described in U.S. Pat. No. 5,849,902; which is hereby incorporated herein by reference in its entirety.

| ID# | Sequence | |
|---|---|---|
| 13594 | CCAUCUUCCACGUUGCUCACACUGG | (SEQ ID NO:87) |
| 13595 | UCCCACAGAGGAUCCAGGCACUCCU | (SEQ ID NO:88) |
| 13596 | AUGUGACACUGCCGUUCUGCUCAGA | (SEQ ID NO:89) |
| 13597 | GGACCUUCUAUAGACUCCCUUGGAU | (SEQ ID NO:90) |
| 13598 | GGAAUAAGACAUAAUCCUGCAGGCC | (SEQ ID NO:91) |

The HGPRBMY11 polypeptide has been shown to be involved in the regulation of mammalian NF-κB and apoptosis pathways. Subjecting cells with an effective amount of a pool of all five of the above antisense oligoncleotides resulted in a significant increase in IκBα expression/activity providing convincing evidence that HGPRBMY11 at least regulates the activity and/or expression of IκBα either directly, or indirectly. Moreover, the results suggest that HGPRBMY11 is involved in the negative regulation of NF-κB/IκBα activity and/or expression, either directly or indirectly. The IκBα assay used is described below and was based upon the analysis of IκBα activity as a downstream marker for proliferative signal transduction events.

Transfection of Post-Quiescent A549 Cells with AntiSense Oligonucleotides Materials Needed A549 cells maintained in DMEM with high glucose (Gibco-BRL) supplemented with 10% Fetal Bovine Serum, 2 mM L-Glutamine, and 1× penicillin/streptomycin.
  Opti-MEM (Gibco-BRL)
  Lipofectamine 2000 (Invitrogen)
  Antisense oligomers (Sequitur)
  Polystyrene tubes.
  Tissue culture treated plates.
  Quiescent cells were prepared as follows:
  Day 0: 300, 000 A549 cells were seeded in a T75 tissue culture flask in 10 ml of A549 media (as specified above), and incubated in at 37° C., 5% $CO_2$ in a humidified incubator for 48 hours.
  Day 2: The T75 flasks were rocked to remove any loosely adherent cells, and the A549 growth media removed and replenished with 10 ml of fresh A549 media. The cells were cultured for six days without changing the media to create a quiescent cell population.
  Day 8: Quiescent cells were plated in multi-well format and transfected with antisense oligonucleotides.
  A549 cells were transfected according to the following:
  1. Trypsinize T75 flask containing quiescent population of A549 cells.
  2. Count the cells and seed 24-well plates with 60K quiescent A549 cells per well.
  3. Allow the cells to adhere to the tissue culture plate (approximately 4 hours).
  4. Transfect the cells with antisense and control oligonucleotides according to the following:
  a. A 10× stock of lipofectamine 2000 (10 ug/ml is 10×) was prepared, and diluted lipid was allowed to stand at RT for 15 minutes.
  Stock solution of lipofectamine 2000 was 1 mg/ml.
  10× solution for transfection was 10 ug/ml.
  To prepare 10× solution, dilute 10 ul of lipofectamine 2000 stock per 1 ml of Opti-MEM (serum free media).
  b. A 10× stock of each oligomer was prepared to be used in the transfection.
  Stock solutions of oligomers were at 100 uM in 20 mM HEPES, pH 7.5.
  10× concentration of oligomer was 0.25 uM.
  To prepare the 10× solutions, dilute 2.5 ul of oligomer per 1 ml of Opti-MEM.
  c. Equal volumes of the 11× lipofectamine 2000 stock and the 10× oligomer solutions were mixed well, and incubated for 15 minutes at RT to allow complexation of the oligomer and lipid. The resulting mixture was 5×.
  d. After the 15 minute complexation, 4 volumes of full growth media was added to the oligomer/lipid complexes (solution was 1×).
  e. The media was aspirated from the cells, and 0.5 ml of the 1× oligomer/lipid complexes added to each well.
  f. The cells were incubated for 16-24 hours at 37° C. in a humidified $CO_2$ incubator.
  g. Cell pellets were harvested for RNA isolation and Taq-Man analysis of downstream marker genes.

TaqMan Reactions

Quantitative RT-PCR analysis was performed on total RNA preps that had been treated with DNaseI or poly A selected RNA. The Dnase treatment may be performed using methods known in the art, though preferably using a Qiagen RNeasy kit to purify the RNA samples, wherein DNAse I treatment is performed on the column.

Briefly, a master mix of reagents was prepared according to the following table:

| Dnase I Treatment | |
|---|---|
| Reagent | Per r'xn (in uL) |
| 10× Buffer | 2.5 |
| Dnase I (1 unit/ul @1 unit per ug sample) | 2 |
| DEPC $H_2O$ | 0.5 |
| RNA sample @ 0.1 ug/ul (2-3 ug total) | 20 |
| Total | 25 |

Next, 5 ul of master mix was aliquoted per well of a 96-well PCR reaction plate (PE part # N801-0560). RNA samples were adjusted to 0.1 ug/ul with DEPC treated $H_2O$ (if necessary), and 20 ul was added to the aliquoted master mix for a final reaction volume of 25 ul.

The wells were capped using strip well caps (PE part # N801-0935), placed in a plate, and briefly spun in a plate centrifuge (Beckman) to collect all volume in the bottom of the tubes. Generally, a short spin up to 500 rpm in a Sorvall RT is sufficient The plates were incubated at 37° C. for 30 mins. Then, an equal volume of 0.1 mM EDTA in 10 mM Tris was added to each well, and heat inactivated at 70° C. for 5 min. The plates were stored at −80° C. upon completion.

RT Reaction

A master mix of reagents was prepared according to the following table:

| | RT reaction | |
|---|---|---|
| Reagent | RT Per Rx'n (in ul) | No RT Per Rx'n (in ul) |
| 10× RT buffer | 5 | 2.5 |
| $MgCl_2$ | 11 | 5.5 |
| DNTP mixture | 10 | 5 |
| Random Hexamers | 2.5 | 1.25 |
| Rnase inhibitors | 1.25 | 0.625 |
| RT enzyme | 1.25 | — |
| Total RNA 500 ng (100 ng no RT) | 19.0 max | 10.125 max |
| DEPC $H_2O$ | — | — |
| Total | 50 uL | 25 uL |

Samples were adjusted to a concentration so that 500 ng of RNA was added to each RT rx'n (100 ng for the no RT). A maximum of 19 ul can be added to the RT rx'n mixture (10.125 ul for the no RT.) Any remaining volume up to the maximum values was filled with DEPC treated $H_2O$, so that the total reaction volume was 50 ul (RT) or 25 ul (no RT).

On a 96-well PCR reaction plate (PE part # N801-0560), 37.5 ul of master mix was aliquoted (22.5 ul of no RT master mix), and the RNA sample added for a total reaction volume of 50 ul (25 ul, no RT). Control samples were loaded into two or even three different wells in order to have enough template for generation of a standard curve.

The wells were capped using strip well caps (PE part # N801-0935), placed in a plate, and spin briefly in a centrifuge to collect all volume in the bottom of the tubes. Generally, a short spin up to 500 rpm in a Sorvall RT is sufficient.

For the RT-PCR reaction, the following thermal profile was used:
25° C. for 10 min
48° C. for 30 min
95° C. for 5 min
4° C. hold (for 1 hour)
Store plate @–20° C. or lower upon completion.

TaqMan Reaction (Template Comes from RT Plate)

A master mix was prepared according to the following table:

| TaqMan reaction (per well) | |
| --- | --- |
| Reagent | Per Rx'n (in ul) |
| TaqMan Master Mix | 4.17 |
| 100 uM Probe (SEQ ID NO: 94) | .025 |
| 100 uM Forward primer (SEQ ID NO: 92) | .05 |
| 100 uM Reverse primer (SEQ ID NO: 93) | .05 |
| Template | — |
| DEPC H$_2$O | 18.21 |
| Total | 22.5 |

The primers used for the RT-PCR reaction is as follows: IκBα primer and probes:

```
                                    (SEQ ID NO:92)
Forward Primer:     GAGGATGAGGAGAGCTATGACACA (SEQ ID NO:93)
Reverse Primer:     CCCTTTGCACTCATAACGTCAG (SEQ ID NO:94)
TaqMan Probe:       AAACACACAGTCATCATAGGGCAGCTCGT
```

Using a Gilson P-10 repeat pipetter, 22.5 ul of master mix was aliquouted per well of a 96-well optical plate. Then, using P-10 pipetter, 2.5 ul of sample was added to individual wells. Generally, RT samples are run in triplicate with each primer/probe set used, and no RT samples are run once and only with one primer/probe set, often gapdh (or other internal control).

A standard curve is then constructed and loaded onto the plate. The curve has five points plus one no template control (NTC, =DEPC treated H$_2$O). The curve was made with a high point of 50 ng of sample (twice the amount of RNA in unknowns), and successive samples of 25, 10, 5, and 1 ng. The curve was made from a control sample(s) (see above).

The wells were capped using optical strip well caps (PE part # N801-0935), placed in a plate, and spun in a centrifuge to collect all volume in the bottom of the tubes. Generally, a short spin up to 500 rpm in a Sorvall RT is sufficient.

Plates were loaded onto a PE 5700 sequence detector making sure the plate is aligned properly with the notch in the upper right hand corner. The lid was tightened down and run using the 5700 and 5700 quantitation program and the SYBR probe using the following thermal profile:
50° C. for 2 min
95° C. for 10 min
and the following for 40 cycles:
95° C. for 15 sec
60° C. for 1 min
Change the reaction volume to 25 ul.

Once the reaction was complete, a manual threshold of around 0.1 was set to minimuze the background signal. Additional information relative to operation of the GeneAmp 5700 machine may be found in reference to the following manuals: "GeneAmp 5700 Sequence Detection System Operator Training CD"; and the "User's Manual for 5700 Sequence Detection System"; available from Perkin-Elmer and hereby incorporated by reference herein in their entirety.

Example 8

Method of Screening, In Vitro, Compounds that Bind to the HGPRBMY11 Polypeptide

In vitro systems can be designed to identify compounds capable of binding the HGPRBMY11 polypeptide of the invention. Compounds identified can be useful, for example, in modulating the activity of wild type and/or mutant HGPRBMY11 polypeptide, preferably mutant HGPRBMY11 polypeptide, can be useful in elaborating the biological function of the HGPRBMY11 polypeptide, can be utilized in screens for identifying compounds that disrupt normal HGPRBMY11 polypeptide interactions, or can in themselves disrupt such interactions.

The principle of the assays used to identify compounds that bind to the HGPRBMY11 polypeptide involves preparing a reaction mixture of the HGPRBMY11 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring HGPRBMY11 polypeptide or the test substance onto a solid phase and detecting HGPRBMY11 polypeptide/test compound complexes anchored on the solid phase at the end of the reaction. In one embodiment of such a method, the HGPRBMY11 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HGPRBMY11 polypeptide or the test compound to anchor any complexes formed in solution, and a labeled antibody specific for the other component of the possible complex to detect anchored complexes.

Another example of a screening assay to identify compounds that bind to HGPRBMY11, relates to the application of a cell membrane-based scintillation proximity assay ("SPA"). Such an assay would require the idenification of a ligand for HGPRBMY11 polypeptide. Once identified, unlabeled ligand is added to assay-ready plates that would serve as a positive control. The SPA beads and membranes are added next, and then $^{125}$I-labeled ligand is added. After an equilibration period of 2-4 hours at room temperature, the plates can be counted in a scintillation counting machine, and the percent inhibition or stimulation calculated. Such an SPA assay may be based upon a manual, automated, or semi-automated platform, and encompass 96, 384, 1536-well plates or more. Any number of SPA beads may be used as applicable to each assay. Examples of SPA beads include, for example, Leadseeker WGA PS (Amersham cat # RPNQ 0260), and SPA Beads (PVT-PEI-WGA-TypeA; Amersham cat # RPNQ0003). The utilized membranes may also be derived from a number of cell line and tissue sources depending upon the expression profile of the respective polypeptide and the adaptability of such a cell line or tissue source to the development of a SPA-based assay. Examples of membrane preparations include, for example, cell lines transformed to express the receptor to be assayed in CHO cells or HEK cells, for example. SPA-based assays are well known in the art and are encompassed by the present invention. One such assay is described in U.S. Pat. No. 4,568,649, which is incorporated herein by reference. The skilled artisan would acknowledge that certain modifications of known SPA assays may be required to adapt such assays to each respective polypeptide.

One such screening procedure involves the use of melanophores which are transfected to express the HGPRBMY11 polypeptide of the present invention. Such a screening technique is described in PCT WO 92/01810, published Feb. 6, 1992. Such an assay may be employed to screen for a compound which inhibits activation of the receptor polypeptide of the present invention by contacting the melanophore cells which encode the receptor with both the receptor ligand, such as LPA, and a compound to be screened. Inhibition of the signal generated by the ligand indicates that a compound is a potential antagonist for the receptor, i.e., inhibits activation of the receptor.

The technique may also be employed for screening of compounds which activate the receptor by contacting such cells with compounds to be screened and determining whether such compound generates a signal, i.e., activates the receptor. Other screening techniques include the use of cells which express the HGPRBMY11 polypeptide (for example, transfected CHO cells) in a system which measures extracellular pH changes caused by receptor activation. In this technique, compounds may be contacted with cells expressing the receptor polypeptide of the present invention. A second messenger response, e.g., signal transduction or pH changes, is then measured to determine whether the potential compound activates or inhibits the receptor.

Another screening technique involves expressing the HGPRBMY11 polypeptide in which the receptor is linked to phospholipase C or D. Representative examples of such cells include, but are not limited to, endothelial cells, smooth muscle cells, and embryonic kidney cells. The screening may be accomplished as hereinabove described by detecting activation of the receptor or inhibition of activation of the receptor from the phospholipase second signal.

Another method involves screening for compounds which are antagonists or agonists by determining inhibition of binding of labeled ligand, such as LPA, to cells which have the receptor on the surface thereof, or cell membranes containing the receptor. Such a method involves transfecting a cell (such as eukaryotic cell) with DNA encoding the HGPRBMY11 polypeptide such that the cell expresses the receptor on its surface. The cell is then contacted with a potential antagonist or agonist in the presence of a labeled form of a ligand, such as LPA. The ligand can be labeled, e.g., by radioactivity. The amount of labeled ligand bound to the receptors is measured, e.g., by measuring radioactivity associated with transfected cells or membrane from these cells. If the compound binds to the receptor, the binding of labeled ligand to the receptor is inhibited as determined by a reduction of labeled ligand which binds to the receptors. This method is called binding assay.

Another screening procedure involves the use of mammalian cells (CHO, HEK 293, *Xenopus* Oocytes, RBL-2H3, etc) which are transfected to express the receptor of interest. The cells are loaded with an indicator dye that produces a fluorescent signal when bound to calcium, and the cells are contacted with a test substance and a receptor agonist, such as LPA. Any change in fluorescent signal is measured over a defined period of time using, for example, a fluorescence spectrophotometer or a fluorescence imaging plate reader. A change in the fluorescence signal pattern generated by the ligand indicates that a compound is a potential antagonist or agonist for the receptor.

Another screening procedure involves use of mammalian cells (CHO, HEK293, *Xenopus* Oocytes, RBL-2H3, etc.) which are transfected to express the receptor of interest, and which are also transfected with a reporter gene construct that is coupled to activation of the receptor (for example, luciferase or beta-galactosidase behind an appropriate promoter). The cells are contacted with a test substance and the receptor agonist (ligand), such as LPA, and the signal produced by the reporter gene is measured after a defined period of time. The signal can be measured using a luminometer, spectrophotometer, fluorimeter, or other such instrument appropriate for the specific reporter construct used. Change of the signal generated by the ligand indicates that a compound is a potential antagonist or agonist for the receptor.

Another screening technique for antagonists or agonits involves introducing RNA encoding the HGPRBMY11 polypeptide into *Xenopus* oocytes (or CHO, HEK 293, RBL-2H3, etc.) to transiently or stably express the receptor. The receptor oocytes are then contacted with the receptor ligand, such as LPA, and a compound to be screened. Inhibition or activation of the receptor is then determined by detection of a signal, such as, cAMP, calcium, proton, or other ions.

Another method involves screening for HGPRBMY11 polypeptide inhibitors by determining inhibition or stimulation of HGPRBMY11 polypeptide-mediated cAMP and/or adenylate cyclase accumulation or dimunition. Such a method involves transiently or stably transfecting a eukaryotic cell with HGPRBMY11 polypeptide receptor to express the receptor on the cell surface.

The cell is then exposed to potential antagonists or agonists in the presence of HGPRBMY11 polypeptide ligand, such as LPA. The changes in levels of cAMP is then measured over a defined period of time, for example, by radio-immuno or protein binding assays (for example using Flashplates or a scintillation proximity assay). Changes in cAMP levels can also be determined by directly measuring the activity of the enzyme, adenylyl cyclase, in broken cell preparations. If the potential antagonist or agonist binds the receptor, and thus inhibits HGPRBMY11 polypeptide-ligand binding, the levels of HGPRBMY11 polypeptide-mediated cAMP, or adenylate cyclase activity, will be reduced or increased.

One preferred screening method involves co-transfecting HEK-293 cells with a mammalian expression plasmid encoding a G-protein coupled receptor (GPCR), such as HGPRBMY11, along with a mixture comprised of mammalian expression plasmids cDNAs encoding GU15 (Wilkie T. M. et al Proc Natl Acad Sci USA 1991 88: 10049-10053), GU16 (Amatruda T. T. et al Proc Natl Acad Sci USA 1991 8: 5587-5591, and three chimeric G-proteins refered to as Gqi5, Gqs5, and Gqo5 (Conklin B R et al Nature 1993 363: 274-276, Conklin B. R. et al Mol Pharmacol 1996 50: 885-890). Following a 24 h incubation the trasfected HEK-293 cells are plated into poly-D-lysine coated 96 well black/clear plates (Becton Dickinson, Bedford, Mass.).

The cells are assayed on FLIPR (Fluorescent Imaging Plate Reader, Molecular Devices, Sunnyvale, Calif.) for a calcium mobilization response following addition of test ligands. Upon identification of a ligand which stimulates calcium mobilization in HEK-293 cells expressing a given GPCR and the G-protein mixtures, subsequent experiments are performed to determine which, if any, G-protein is required for the functional response. HEK-293 cells are then transfected with the test GPCR, or co-transfected with the test GPCR and G015, GD16, GqiS, Gqs5, or Gqo5. If the GPCR requires the presence of one of the G-proteins for functional expression in HEK-293 cells, all subsequent experiments are performed with HEK-293 cell cotransfected with the GPCR and the G-protein which gives the best response. Alternatively, the receptor can be expressed in a different cell line, for example RBL-2H3, without additional Gproteins.

Another screening method for agonists and antagonists relies on the endogenous pheromone response pathway in the yeast, *Saccharomyces cerevisiae*. Heterothallic strains of yeast can exist in two mitotically stable haploid mating types, MATa and MATa. Each cell type secretes a small peptide hormone that binds to a G-protein coupled receptor on opposite mating type cells which triggers a MAP kinase cascade leading to G1 arrest as a prelude to cell fusion.

Genetic alteration of certain genes in the pheromone response pathway can alter the normal response to pheromone, and heterologous expression and coupling of human G-protein coupled receptors and humanized G-protein subunits in yeast cells devoid of endogenous pheromone receptors can be linked to downstream signaling pathways and reporter genes (e.g., U.S. Pat. Nos. 5,063,154; 5,482,835; 5,691,188). Such genetic alterations include, but are not limited to, (i) deletion of the STE2 or STE3 gene encoding the endogenous G-protein coupled pheromone receptors; (ii) deletion of the FAR1 gene encoding a protein that normally associates with cyclindependent kinases leading to cell cycle arrest; and (iii) construction of reporter genes fused to the FUS 1 gene promoter (where FUS 1 encodes a membrane-anchored glycoprotein required for cell fusion). Downstream reporter genes can permit either a positive growth selection (e.g., histidine prototrophy using the FUS1-HIS3 reporter), or a colorimetric, fluorimetric or spectrophotometric readout, depending on the specific reporter construct used (e.g., b-galactosidase induction using a FUS1-LacZ reporter).

The yeast cells can be further engineered to express and secrete small peptides from random peptide libraries, some of which can permit autocrine activation of heterologously expressed human (or mammalian) G-protein coupled receptors (Broach, J. R. and Thorner, J., Nature 384: 14-16, 1996; Manfredi et al., Mol. Cell. Biol. 16: 4700-4709, 1996). This provides a rapid direct growth selection (e.g, using the FUS 1-HIS3 reporter) for surrogate peptide agonists that activate characterized or orphan receptors. Alternatively, yeast cells that functionally express human (or mammalian) G-protein coupled receptors linked to a reporter gene readout (e.g., FUS1-LacZ) can be used as a platform for high-throughput screening of known ligands, fractions of biological extracts and libraries of chemical compounds for either natural or surrogate ligands.

Functional agonists of sufficient potency (whether natural or surrogate) can be used as screening tools in yeast cell-based assays for identifying G-protein coupled receptor antagonists. For example, agonists will promote growth of a cell with FUS-HIS3 reporter or give positive readout for a cell with FUSI-LacZ. However, a candidate compound which inhibits growth or negates the positive readout induced by an agonist is an antagonist. For this purpose, the yeast system offers advantages over mammalian expression systems due to its ease of utility and null receptor background (lack of endogenous G-protein coupled receptors) which often interferes with the ability to identify agonists or antagonists.

Example 9

Method of Assessing the Physiological Function of the HGPRBMY11 Polypeptide at the Cellular Level The physiological function of the HGPRBMY11 polypeptide may be assessed by expressing the sequences encoding HGPRBMY11 at physiologically elevated levels in mammalian cell culture systems. cDNA is subcloned into a mammalian expression vector containing a strong promoter that drives high levels of cDNA expression (examples are provided elsewhere herein). Vectors of choice include pCMV SPORT (Life Technologies) and pCR3.1 (Invitrogen, Carlsbad Calif.), both of which contain the cytomegalovirus promoter. 5-10, ug of recombinant vector are transiently transfected into a human cell line, preferably of endothelial or hematopoietic origin, using either liposome formulations or electroporation. 1-2 ug of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of HGPRBMY11 polypeptides on gene expression can be assessed using highly purified populations of cells transfected with sequences encoding HGPRBMY11 and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HGPRBMY11 polypeptides and other genes of interest can be analyzed by northern analysis or microarray techniques.

Example 10

Method of Assessing the Physiological Function of the HGPRBMY11 Polypeptides in *Xenopus* Oocytes Capped RNA transcripts from linearized plasmid templates encoding the receptor cDNAs of the invention are synthesized in vitro with RNA polymerases in accordance with standard procedures.

In vitro transcripts are suspended in water at a final concentration of 0.2 mg/ml. Ovarian lobes are removed from adult female toads, Stage V defolliculatedoocytes are obtained, and RNA transcripts (10 ng/oocyte) are injected in a 50 nl bolus using a microinjection apparatus. Two electrode voltage clamps are used to measure the currents from individual *Xenopus* oocytes in response to agonist exposure. Recordings are made in Ca2+ free Barth's medium at room temperature.

In a preferred embodiment, such a system can be used to screen known ligands and tissue/cell extracts for activating ligands. A number of GPCR ligands are known in the art and are encompassed by the present invention (see, for example, The G-Protein Linked Receptor Facts Book, referenced elsewhere herein).

Example 11

Method of Assessing the Physiological Function of the HGPRBMY11 Polypeptides Using Microphysiometric Assays Activation of a wide variety of secondary messenger systems results in extrusion of small amounts of acid from a cell. The acid formed is largely as a result of the increased metabolic activity required to fuel the intracellular signaling process. The pH changes in the media surrounding the cell are very small but are detectable by the CYTOSENSOR microphysiometer (Molecular Devices Ltd., Menlo Park, Calif.). The CYTOSENSOR is thus capable of detecting the activation of a receptor that is coupled to an energy utilizing intracellular signaling pathway such as the G-protein coupled receptor of the present invention.

Example 12

Method of Assessing the Physiological Function of the HGPRBMY11 Polypeptides Using Calcium and Camp Functional Assays A well known observation in the art relates to the fact that GPCR receptors which are expressed in HEK 293 cells have been shown to be functionally couple—leading to subsequent activation of phospoholipase C (PLC) and calcium mobilization, and/or cAMP stimuation or inhibition.

Based upon the above, calcium and cAMP assays may be useful in assessing the ability of HGPRBMY11 to serve as a GPCR. Briefly, basal calcium levels in the HEK 293 cells in HGPRBMY11-transfected or vector control cells can be observed to determine whether the levels fall within a normal physiological range, 100 nM to 200 nM. HEK 293 cells expressing recombinant receptors are then loaded with fura 2 and in a single day selected GPCR ligands or tissue/cell extracts are evaluated for agonist induced calcium mobilization. Similarly, HEK 293 cells expressing recombinant HGPRBMY11 receptors are evaluated for the stimulation or inhibition of cAMP production using standard cAMP quantitation assays. Agonists presenting a calcium transient or cAMP flucuation are tested in vector control cells to determine if the response is unique to the transfected cells expressing the HGPRBMY11 receptor.

Example 13

Method of Screening for Compounds that Interact with the HGPRBMY11 Polypeptide

The following assays are designed to identify compounds that bind to the HGPRBMY11 polypeptide, bind to other cellular proteins that interact with the HGPRBMY11 polypeptide, and to compounds that interfere with the interaction of the HGPRBMY11 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of HGPRBMY11 polypeptide transmembrane receptors, and members of random peptide libraries (see, e.g., Lam, K. S. et al., 1991, Nature 354:82-84; Houghton, R. et al., 1991, Nature 354:84-86), made of D- and/or L-configuration amino acids, phosphopeptides (including, but not limited to, members of random or partially degenerate phosphopeptide libraries; see, e.g., Songyang, Z., et al., 1993, Cell 72:767-778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the HGPRBMY11 polypeptide, and for ameliorating symptoms of tumor progression, for example. In instances, for example, whereby a tumor progression state or disorder results from a lower overall level of HGPRBMY11 expression, HGPRBMY11 polypeptide, and/or HGPRBMY11 polypeptide activity in a cell involved in the tumor progression state or disorder, compounds that interact with the HGPRBMY11 polypeptide can include ones which accentuate or amplify the activity of the bound HGPRBMY11 polypeptide. Such compounds would bring about an effective increase in the level of HGPRBMY11 polypeptide activity, thus ameliorating symptoms of the tumor progression disorder or state. In instances whereby mutations within the HGPRBMY11 polypeptide cause aberrant HGPRBMY11 polypeptides to be made which have a deleterious effect that leads to tumor progression, compounds that bind HGPRBMY11polypeptide can be identified that inhibit the activity of the bound HGPRBMY11 polypeptide. Assays for testing the effectiveness of such compounds are known in the art and discussed, elsewhere herein.

Example 14

Method of Screening, In Vitro, Compounds that Bind to The HGPRBMY11 Polypeptide

In vitro systems can be designed to identify compounds capable of binding the HGPRBMY11 polypeptide of the invention. Compounds identified can be useful, for example, in modulating the activity of wild type and/or mutant HGPRBMY11 polypeptide, preferably mutant HGPRBMY11 polypeptide, can be useful in elaborating the biological function of the HGPRBMY11 polypeptide, can be utilized in screens for identifying compounds that disrupt normal HGPRBMY11 polypeptide interactions, or can in themselves disrupt such interactions.

The principle of the assays used to identify compounds that bind to the HGPRBMY11 polypeptide involves preparing a reaction mixture of the HGPRBMY11 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring HGPRBMY11 polypeptide or the test substance onto a solid phase and detecting HGPRBMY11 polypeptide/test compound complexes anchored on the solid phase at the end of the reaction. In one embodiment of such a method, the HGPRBMY11 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HGPRBMY11 polypeptide or the test compound to anchor any complexes formed in solution, and a labeled antibody specific for the other component of the possible complex to detect anchored complexes.

Example 15

Method for Identifying a Putative Ligand for the HGCRBMY11 Polypeptide

Ligand binding assays provide a direct method for ascertaining receptor pharmacology and are adaptable to a high throughput format. A panel of known GPCR purified ligands may be radiolabeled to high specific activity (50-2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

A number of GPCR ligands are known in the art and are encompassed by the present invention (see, for example, The G-Protein Linked Receptor Facts Book, referenced elsewhere herein).

Alternatively, the HGPRBMY 11 polypeptide of the present invention may also be functionally screened (using calcium, cAMP, microphysiometer, oocyte electrophysiology, etc., functional screens) against tissue extracts to identify natural ligands. Extracts that produce positive functional responses can be sequencially subfractionated until an activating ligand is isolated identified using methods well known in the art, some of which are described herein.

Example 16

Method of Identifying Compounds that Interfere with HGPRBMY11 Polypeptide/Cellular Product Interaction The HGPRBMY11 polypeptide of the invention can, in vivo, interact with one or more cellular or extracellular macromolecules, such as proteins. Such macromolecules include, but are not limited to, polypeptides, particularly GPCR ligands, and those products identified via screening methods described, elsewhere herein. For the purposes of this discussion, such cellular and extracellular macromolecules are referred to herein as "binding partner(s)". For the purpose of the present invention, "binding partner" may also encompass polypeptides, small molecule compounds, polysaccarides, lipids, and any other molecule or molecule type referenced herein. Compounds that disrupt such interactions can be useful in regulating the activity of the HGPRBMY11 polypeptide, especially mutant HGPRBMY11 polypeptide. Such compounds can include, but are not limited to molecules such as antibodies, peptides, and the like described in elsewhere herein.

The basic principle of the assay systems used to identify compounds that interfere with the interaction between the HGPRBMY11 polypeptide and its cellular or extracellular binding partner or partners involves preparing a reaction mixture containing the HGPRBMY11 polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of HGPRBMY11 polypeptide and its cellular or extracellular binding partner. Control reaction mixtures are incubated without the test compound or with a placebo. The formation of any complexes between the HGPRBMY11 polypeptide and the cellular or extracellular binding partner is then detected. The formation of a complex in the control reaction, but not in the reaction mixture containing the test compound, indicates that the compound interferes with the interaction of the HGPRBMY11 polypeptide and the interactive binding partner. Additionally, complex formation within reaction mixtures containing the test compound and normal HGPRBMY11 polypeptide can also be compared to complex formation within reaction mixtures containing the test compound and mutant HGPRBMY11 polypeptide. This comparison can be important in those cases wherein it is desirable to identify compounds that disrupt interactions of mutant but not normal HGPRBMY11 polypeptide.

The assay for compounds that interfere with the interaction of the HGPRBMY11 polypeptide and binding partners can be conducted in a heterogeneous or homogeneous format. Heterogeneous assays involve anchoring either the HGPRBMY11 polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the HGPRBMY11 polypeptide and the binding partners, e.g., by competition, can be identified by conducting the reaction in the presence of the test substance; i.e., by adding the test substance to the reaction mixture prior to or simultaneously with the HGPRBMY11 polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the HGPRBMY11 polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the HGPRBMY11 polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the HGPRBMY11 polypeptide and the interactive cellular or extracellular binding partner product is prepared in which either the HGPRBMY11 polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt HGPRBMY11 polypeptide-cellular or extracellular binding partner interaction can be identified.

In a particular embodiment, the HGPRBMY11 polypeptide can be prepared for immobilization using recombinant DNA techniques known in the art. For example, the HGPRBMY11 polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-HGPRBMY11 polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the HGPRBMY11 polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-HGPRBMY11 polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the HGPRBMY11 polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 17

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84-86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

Human IgG Fc region:

(SEQ ID NO:27)
GGGATCCGGAGCCCAAATCTTCTGACAAAACTCACACATGGCCACCGTGC

CCAGCACCTGAATTGGAGGGTGCACCGTCAGTCTTCCTCTTCCCCCCAAA

AGCCAAGGACACCCTCATGATCTCCCGGACTCCTGAGGTCACATGCGTGG

TGGTGGACGTAAGCCACGAAGACCCTGAGGTCAAGTTCAACTGGTAGGTG

GAGGGGGTGGAGGTGCATAATGCGAAGACAAAGCCGCGGGAGGAGCAGTA

CAACAGCACGTAGCGTGTGGTCAGCGTCCTCACCGTCCTGCACCAGGACT

GGCTGAATGGGAAGGAGTACAAGTGCAAGGTCTCCAACAAAGCCCTCCGA

ACGCCCATCGAGAAAACCATCTCCAAAGCCAAAGGGCAGCCCCGAGAACC

ACAGGTGTAGAGCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGGTGGACTCCGACGGCTCCTTCTTCCTCTACAGCAAGGTCACCGTGG

AGAAGAGGAGGTGGCAGCAGGGGAACGTCTTGTCATGGTCCGTGATGCAT

GAGGCTCTGCACAACCACTACACGCAGAAGAGGGTCTCCCTGTCTCCGGG

TAAATGAGTGCGACGGCGGCGACTCTAGAGGAT

Example 18

Method of Enhancing the Biological Activity/Functional Characteristics of Invention through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered G-protein coupled receptor may be constitutively active upon binding of its cognate ligand. Alternatively, an engineered G-protein coupled receptor may be constitutively active in the absence of ligand binding. In yet another example, an engineered GPCR may be capable of being activated with less than all of the regulatory factors and/or conditions typically required for GPCR activation (e.g., ligand binding, phosphorylation, conformational changes, expression, etc.). Such GPCRs would be useful in screens to identify GPCR modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145-152, (1986), and Hill, D E, et al, Methods Enzymol., 55:559-568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2-4 ug of the DNA substrate(s) would be digested with 0.0015 units of Dnase I (Sigma) per ul in 100 ul of 50 mM Tris-HCL, pH 7.4/1 mM $MgCl_2$ for 10-20 min. at room temperature. The resulting fragments of 10-50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10-50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM $MgCl_2$, 50 mM KCl, 10 mM Tris•HCL, pH 9.0, and 0.1% Triton X-100, at a final fragment concentration of 10-30 ng/ul. No primers are added at this point. Taq DNA polymerase (Promega) would be used at 2.5 units per 100 ul of reaction mixture. A PCR program of 94 C for 60 s; 94 C for 30 s, 50-55 C for 30 s, and 72 C for 30 s using 3045 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to elsewhere herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6):1307-1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336-347, (1997), F. R., Cross, et al., Mol. Cell. Biol., 18:2923-2931, (1998), and A. Crameri., et al., Nat. Biotech., 15:436-438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436-438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 19

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 20

Method of Creating N- and C-Terminal Deletion Mutants corresponding to the HGPRBMY11, and HGPRBMY11v1, and HGPRBMY11v2 Polypeptides of the Present Invention As described elsewhere herein, the present invention encompasses the creation of N- and C-terminal deletion mutants, in addition to any combination of N- and C-terminal deletions thereof, corresponding to the HGPRBMY11, HGPRBMY11v1, and HGPRBMY11v2 polypeptides of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length HGPRBMY11, HGPRBMY11v1, or HGPRBMY11v2 polypeptide sequence, appropriate primers of about 15-25 nucleotides derived from the desired 5' and 3' positions of SEQ ID NO:1 SEQ ID NO:29, or SEQ ID NO:54 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the E23 to V330 HGPRBMY11 N-terminal deletion mutant, the following primers could be used to amplify a cDNA fragment corresponding to this deletion mutant:

```
5' Primer
                                        (SEQ ID NO:46)
5'-GCAGCA GCGGCCGC GAATTTTTCCCAATTGTATATCTG -3'
           NotI 3' Primer
                                        (SEQ ID NO:47)
5'- GCAGCA GTCGAC TTATACTCTTGTTTCCTTTCTCAAC -3'
           SalI
```

For example, in the case of the M1 to G293 HGPRBMY11 C-terminal deletion mutant, the following primers could be used to amplify a cDNA fragment corresponding to this deletion mutant:

```
5' Primer
                                        (SEQ ID NO:48)
5'- GCAGCA GCGGCCGC ATGGAACCAAATGGCACCTTCAGC -3'
           NotI 3' Primer
                                        (SEQ ID NO:49)
5'- GCAGCA GTCGAC CCCAGCAAAGTAATAGAGCAGAGG -3'
           SalI
```

For example, in the case of the E23 to V330 HGPRBMY11v1 N-terminal deletion mutant, the following primers could be used to amplify a cDNA fragment corresponding to this deletion mutant:

```
5' Primer
                                        (SEQ ID NO:50)
5'-GCAGCA GCGGCCGC GAATTTTTCCCAATTGTATATCTG -3'
           NotI 3' Primer
                                        (SEQ ID NO:51)
5'- GCAGCA GTCGAC TACTCTTGTTTCCTTTCTCAACCAC -3'
           SalI
```

For example, in the case of the M1 to G293 HGPRBMY11v1 C-terminal deletion mutant, the following primers could be used to amplify a cDNA fragment corresponding to this deletion mutant:

```
5' Primer
                                        (SEQ ID NO:52)
5'- GCAGCA GCGGCCGC ATGGAGAGAAAATTTATGTCCTTGC -3'
           NotI 3' Primer
                                        (SEQ ID NO:53)
5'- GCAGCA GTCGAC CCCAGCAAAGTAATAGAGCAGAGG -3'
           SalI
```

Representative PCR amplification conditions are provided below, although the skilled artisan would appreciate that other conditions may be required for efficient amplification. A 100 ul PCR reaction mixture may be prepared using long of the template DNA (cDNA clone of HGPRBMY11, HGPRBMY11v1, or HGPRBMY11v2), 200 uM 4dNTPs, 1 uM primers, 0.25 U Taq DNA polymerase (PE), and standard Taq DNA polymerase buffer. Typical PCR cycling condition are as follows:

20-25 cycles: 45 sec, 93 degrees
  2 min, 50 degrees
  2 min, 72 degrees
1 cycle: 10 min, 72 degrees After the final extension step of PCR, 5 U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent $E.\ coli$ cells using methods provided herein and/or otherwise known in the art.

The 5' primer sequence for amplifying any additional N-terminal deletion mutants may be determined by reference to the following formula: $(S+(X*3))$ to $((S+(X*3))+25)$, wherein 'S' is equal to the nucleotide position of the initiating start codon of the HGPRBMY11, HGPRBMY11v1 or HGPRBMY11v2 gene (SEQ ID NO:1, 29, or 54), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, 29 or 54. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: $(S+(X*3))$ to $((S+(X*3))-25)$, wherein 'S' is equal to the nucleotide position of the initiating start codon of the HGPRBMY11, and HGPRBMY11v1, or HGPRBMY11v2 gene (SEQ ID NO:1, 29, or 54), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, 29 or 54. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 21

Phage Display Methods for Identifying Peptide Ligands or Modulators of Orphan GPCRs Creation of Peptide Libraries To identify HGPRBMY11 binders, two types of libraries were created: i) libraries of 12- and 15-mer peptides, used to find peptides that may function as (ant-)agonists and ii) librar- ies of peptides with 23, 27, or 33 random residues, used to find natural ligands through database searches. The 15-mer library was constructed at Bristol-Myers Squibb using the M13KE vector (New England Biolabs) and a single-stranded library oligonucleotide extension method (S. S. Sidhu et al., *Methods Enzymol.*, 2000, 328:333-363). The 12-mer library was obtained as an aliquot of the M13KE-based 'PhD' 12-mer library (New England Biolabs). The libraries with 23, 27, or 33 random residues were constructed at Bristol-Myers Squibb in vector M13KE (New England Biolabs) using the method described in (S. S. Sidhu et al., Methods Enzymol., 2000, 328:333-363). All libraries in the M13KE vector utilized the standard NNK motif to encode the specified number of random residues, where N=A+G+C+T and where K=G+T. For screening, mixtures of the libraries were used, including Mix 1: 12-mer library and 15-mer library; and Mix 2: 23-mer library, 27-mer library, and 33-mer library.

Panning Method

To minimize cell lysis, especially during the multiple washes, top speeds were not exceeded for centrifugation. For eppendorf centrifuges, spins were carried out at a maximum of 3 K for 30 sec. For refrigerated benchtop centrifuges, spins were performed to reach 3 K, then stopped. Two days prior to panning, CHO-K1 cells were transfected with DNA encoding HGPRBMY11 (pcDNA3.1 Hygro™-HGPRBMY11 construct described in Example 5) using standard procedures. Cells were checked for sufficient expression 48 h post transfection. Sufficient cells were grown to produce a pellet corresponding to ~50 ul volume in an eppendorf tube (~$10^6$~$10^7$ cells). Typically, this corresponded to one P175 flask with near-confluent growth. A similar number of parental cells were grown for preadsorption. One day prior to panning, two or three 96-well Immulon plates were coated integrin. Plates were coated overnight at 4° C. in NaHCO₃, pH 9.5, with ~50 ng of ☐V☐3 integrin (Chemicon; Cat. # CC1020) per well per library.

On the day of panning, growth medium was discarded and cells were washed with 10 ml PBS by allowing the buffer to flow over the cells. The PBS was removed and 10 ml Tris-EDTA detaching buffer (Gibco Cat. # 13150-016; no trypsin) was added for 2 min. Plates were tapped and/or pipetted up and down to detach cells. This was done quickly to minimize the exposure of the cells to this reagent. Cells were pelleted by centrifugation at 3 K, and then washed with 20 ml PBS. Cells were resuspended cells in PBS with 2% milk blocking agent plus protease inhibitor (EDTA-free; Roche Cat. # 1 873 580). For each library, cell suspensions of ~500 ul were used. Cells were blocked for 30-60 min with gentle rocking at room temperature. The integrin-coated wells were washed 3× in PBST, then blocked with 2% BSA in PBS for 30 min or more. To preadsorb against integrin, input phage was added to the integrin-coated wells, and incubated for 30 min or more.

At this stage, the blocked parental cells were divided into the required number of aliquots (500 ul aliquot/library). The phage supernatants were added from the integrin-preadsorption step. Preadsorption against the parental cells was carried out for 30 min or more with gentle rocking. The blocked transfected cells were divided into the required number of aliquots (500 ul aliquot per library). The transfected cells were pelleted, and the supernatant was discarded. The phage supernatants from the two preadsorption steps were added, and cells were incubated with gentle rocking for 2 h or more. Cells were washed 6-8× with PBST at 5 min intervals. Each wash was performed by gently pipetting the cells up and down, and cells were centrifuged at low speed. To recover binding phage from the washed cell pellets, 500 ul 6M urea, pH 3.0 was added for 15 min. This was neutralized with 10 ul 2 M Tris (not adjusted for pH). The phage in the eluate were titered and amplified by standard procedures (NEB protocol for PhD phage libraries). In some cases, the eluate was viscous due to the presence of chromosomal DNA.

Sequencing of Bound Phage

Standard procedures were used. Phage in eluates were infected into E. coli host strain ER2738 (New England Biolabs) for all M13KE-based libraries, and cells were plated for plaques. Colonies were grown in liquid medium and analyzed by standard sequencing procedures. For sequencing, PCR products were generated with suitable primers (Primer 96 from NEB: 5'-GATAAACCGATACAATTAAAG-GCTCC-3' (SEQ ID NO:81)) that annealed adjacent to the library segments in the vectors, and the PCR products were sequenced using one primer of each PCR primer pair. Sequences were analyzed for homologies by visual inspection or by using the Vector NTI alignment tool.

Peptide Synthesis

Peptides are synthesized on Fmoc-Knorr amide resin [N-(9-fluorenyl)methoxycarbonyl-Knorr amide-resin, Midwest Biotech, Fishers, Ind.] with an Applied Biosystems (Foster City, Calif.) model 433A synthesizer and the FastMoc chemistry protocol (0.25 mmol scale) supplied with the instrument. Amino acids are double coupled as their N-alpha-Fmoc-derivatives and reactive side chains are protected as follows: Asp, Glu: t-Butyl ester (OtBu); Ser, Thr, Tyr: t-Butyl ether (tBu); Asn, Cys, Gln, His: Triphenylmethyl (Trt); Lys, Trp: t-Butyloxycarbonyl (Boc); Arg: 2,2,4,6,7-Pentamethyldihydrobenzofuran-5-sulfonyl (Pbf). After the final double coupling cycle, the N-terminal Fmoc group is removed by the multi-step treatment with piperidine in N-Methylpyrrolidone described by the manufacturer. The N-terminal free amines are then treated with 10% acetic anhydride, 5% Diisopropylamine in N-Methylpyrrolidone to yield the N-acetyl-derivative. The protected peptidyl-resins are simultaneously deprotected and removed from the resin by standard methods. The lyophilized peptides are purified on $C_{18}$ to apparent homogeneity as judged by RP-HPLC analysis. Predicted peptide molecular weights are verified by electrospray mass spectrometry. (J. Biol. Chem. vol. 273, pp. 12041-12046, 1998)

Cyclic analogs are prepared from the crude linear products. The cystine disulfide may be formed using one of the following methods:

Method 1: A sample of the crude peptide is dissolved in water at a concentration of 0.5 mg/mL and the pH adjusted to 8.5 with $NH_4OH$. The reaction is stirred, open to room air, and monitored by RP-HPLC.

Once complete, the reaction is brought to pH 4 with acetic acid and lyophilized. The product is purified and characterized as above.

Method 2: A sample of the crude peptide is dissolved at a concentration of 0.5 mg/mL in 5% acetic acid. The pH is adjusted to 6.0 with $NH_4OH$. DMSO (20% by volume) is added and the reaction is stirred overnight. After analytical RP-HPLC analysis, the reaction is diluted with $H_2O$ and triple lyophilized to remove DMSO. The crude product is purified by preparative RP-HPLC. (JACS. vol. 113, 6657, 1991)

| Peptide Modulators of HGPRBMY11: | |
|---|---|
| LFASSDWSSFPVLVF | (SEQ ID NO:81) |
| PLDWGLLPYLHFGSV | (SEQ ID NO:95) |
| THGFGHRVWSVPLRS | (SEQ ID NO:96) |

Assessing Affect of Peptides on GPCR Function

The effect of any one of these peptides on the function of the GPCR of the present invention may be determined by adding an effective amount of each peptide to each functional assay. Representative functional assays are described more specifically herein.

Uses of the Peptide Modulators of the Present Invention

The aforementioned peptides of the present invention are useful for a variety of purposes, though most notably for modulating the function of the GPCR of the present invention, and potentially with other GPCRs of the same G-protein coupled receptor subclass (e.g., peptide receptors, adrenergic receptors, purinergic receptors, etc.), and/or other subclasses known in the art. For example, the peptide modulators of the present invention may be useful as HGPRBMY11 agonists. Alternatively, the peptide modulators of the present invention may be useful as HGPRBMY11 antagonists of the present invention. In addition, the peptide modulators of the present invention may be useful as competitive inhibitors of the HGPRBMY11 cognate ligand(s), or may be useful as non-competitive inhibitors of the HGPRBMY11 cognate ligand(s).

Furthermore, the peptide modulators of the present invention may be useful in assays designed to either deorphan the HGPRBMY11 polypeptide of the present invention, or to identify other agonists or antagonists of the HGPRBMY11 polypeptide of the present invention, particularly small molecule modulators.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. A method of diagnosing Crohn's disease comprising:

a) measuring the expression level of naturally occurring RNA encoding a polypeptide comprising the sequence of SEQ ID NO:2 or a fragment thereof in a Crohn's colon test sample; and b) comparing said expression level of said RNA from a normal Crohn's colon sample; wherein an increased expression level of said RNA in said test sample relative to the expression level of said RNA in said normal sample is indicative of Crohn's disease or a predisposition to Crohn's disease.

2. The method according to claim 1, wherein said RNA measurement comprises specific hybridization between said RNA to the complementary sequence of a member of the group consisting of:

a.) an isolated polynucleotide consisting of SEQ ID NO:1;

b.) an isolated polynucleotide consisting of nucleotides 515 to 1504 of SEQ ID NO:1;

c.) an isolated polynucleotide consisting of nucleotides 518 to 1504 of SEQ ID NO:1; and d.) an isolated polynucleotide encoding the HGPRBMY11 polypeptide as encoded by the cDNA clone contained in ATCC Deposit No: PTA-2766 wherein said complementary polynucleotide sequence hybridizes under stringent conditions to a polynucleotide comprising nucleotides 518 to 1504 of SEQ ID NO:1, wherein said stringent conditions are at least as stringent as an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

3. The method according to claim 1, wherein said RNA measurement comprises specific hybridization between said RNA to an isolated polynucleotide consisting of a complete complement of at least 19 contiguous nucleotides of SEQ ID NO:1, wherein said hybridization is performed under conditions at least as stringent as hybridization in 2.2 mM MgCl2, 50 mM KCI, 10 mM Tris.HCL, pH 9, and 0.1% Triton X-100 at 42 C.

4. The method according to claim 3, wherein said RNA measurement further comprises a second isolated polynucleotide consisting of at least 19 contiguous nucleotides of SEQ ID NO:1, wherein said isolated polynucleotide of claim 3 is directed to the antisense strand, and said second isolated polynucleotide is directed to the sense strand, and wherein said hybridization is followed by at least one amplification step.

* * * * *

UNITED STATES PATENT AND TRADEMARK OFFICE
CERTIFICATE OF CORRECTION

PATENT NO.            : 7,531,310 B2                                      Page 1 of 1
APPLICATION NO.  : 11/403051
DATED                     : May 12, 2009
INVENTOR(S)          : John N. Feder and Chandra S. Ramanathan It is certified that error appears in the above-identified patent and that said Letters Patent is hereby corrected as shown below:

First Page,
Col. 2 (Other Publications)

Delete "vol," and insert -- vol. --
    Delete "Alam" and insert -- Alam, --
    Delete "NF $_k$B" and insert -- NF-$_k$B --

Column 222,
Line 59
    In Claim 2, delete "2766" and insert -- 2766, --

Column 223,
Line 9
    In Claim 3, delete "MgCl2" and insert -- MgCl$_2$ --
Line 10
    In Claim 3, delete "KCI" and insert -- KCl --
    In Claim 3, delete "Tris.HCL," and insert -- Tris•HCL, --
Line 11
    In Claim 3, delete "C." and insert -- degree C. --

Signed and Sealed this

Twenty-fifth Day of August, 2009

David J. Kappos
*Director of the United States Patent and Trademark Office*

SEQUENCE LISTING

<160> NUMBER OF SEQ ID NOS: 94

<210> SEQ ID NO 1
<211> LENGTH: 1708
<212> TYPE: DNA
<213> ORGANISM: homo sapiens
<220> FEATURE:
<221> NAME/KEY: CDS
<222> LOCATION: (515)..(1504)

<400> SEQUENCE: 1

```
cccacgcgtc cggggagctt gcactaacat ctacaatggc ttctaaaaag cacagatgac    60
ctgctacact tcctgacttg cttgctattg gttggcactg ttcataaata taatttgctc   120
tttcactttt ctttgaaatg agcaacctga attactcgga ggagaaaggc aggagagata   180
gaggcagcag aagccagggc agctgaaaga cagagacctt cagtctgaac caacaacaag   240
caaagttaaa ttatggatat ccaagggagt ctatagaagg tccatgcaag acattttgac   300
tacttgtctg aactagatat cccttgaatg tgcacacaaa aagtgaatgg gtcatttgat   360
aagggaaaac taggttccaa gatggctgaa taggaagagc tccagtctgc agatcccagt   420
gtgagcaacg tggaagatgg gtgatttctg catttccaac tgagcatgga gagaaaaatt   480
tatgtccttg caaccatcca tctccgtatc agaa atg gaa cca aat ggc acc ttc   535
                                     Met Glu Pro Asn Gly Thr Phe
                                       1               5 agc aat aac aac agc agg aac tgc aca att gaa aac ttc aag aga gaa   583
Ser Asn Asn Asn Ser Arg Asn Cys Thr Ile Glu Asn Phe Lys Arg Glu
         10                  15                  20 ttt ttc cca att gta tat ctg ata ata ttt ttc tgg gga gtc ttg gga   631
Phe Phe Pro Ile Val Tyr Leu Ile Ile Phe Phe Trp Gly Val Leu Gly
     25                  30                  35 aat ggg ttg tcc ata tat gtt ttc ctg cag cct tat aag aag tcc aca   679
Asn Gly Leu Ser Ile Tyr Val Phe Leu Gln Pro Tyr Lys Lys Ser Thr
40                  45                  50                  55 tct gtg aac gtt ttc atg cta aat ctg gcc att tca gat ctc ctg ttc   727
Ser Val Asn Val Phe Met Leu Asn Leu Ala Ile Ser Asp Leu Leu Phe
                 60                  65                  70 ata agc acg ctt ccc ttc agg gct gac tat tat ctt aga ggc tcc aat   775
Ile Ser Thr Leu Pro Phe Arg Ala Asp Tyr Tyr Leu Arg Gly Ser Asn
             75                  80                  85 tgg ata ttt gga gac ctg gcc tgc agg att atg tct tat tcc ttg tat   823
Trp Ile Phe Gly Asp Leu Ala Cys Arg Ile Met Ser Tyr Ser Leu Tyr
         90                  95                 100 gtc aac atg tac agc agt att tat ttc ctg acc gtg ctg agt gtt gtg   871
Val Asn Met Tyr Ser Ser Ile Tyr Phe Leu Thr Val Leu Ser Val Val
    105                 110                 115 cgt ttc ctg gca atg gtt cac ccc ttt cgg ctt ctg cat gtc acc agc   919
Arg Phe Leu Ala Met Val His Pro Phe Arg Leu Leu His Val Thr Ser
120                 125                 130                 135 atc agg agt gcc tgg atc ctc tgt ggg atc ata tgg atc ctt atc atg   967
Ile Arg Ser Ala Trp Ile Leu Cys Gly Ile Ile Trp Ile Leu Ile Met
                140                 145                 150 gct tcc tca ata atg ctc ctg gac agt ggc tct gag cag aac ggc agt  1015
Ala Ser Ser Ile Met Leu Leu Asp Ser Gly Ser Glu Gln Asn Gly Ser
            155                 160                 165 gtc aca tca tgc tta gag ctg aat ctc tat aaa att gct aag ctg cag  1063
Val Thr Ser Cys Leu Glu Leu Asn Leu Tyr Lys Ile Ala Lys Leu Gln
        170                 175                 180
```

```
acc atg aac tat att gcc ttg gtg gtg ggc tgc ctg ctg cca ttt ttc    1111
Thr Met Asn Tyr Ile Ala Leu Val Val Gly Cys Leu Leu Pro Phe Phe
    185                 190                 195 aca ctc agc atc tgt tat ctg ctg atc att cgg gtt ctg tta aaa gtg    1159
Thr Leu Ser Ile Cys Tyr Leu Leu Ile Ile Arg Val Leu Leu Lys Val
200                 205                 210                 215 gag gtc cca gaa tcg ggg ctg cgg gtt tct cac agg aag gca ctg acc    1207
Glu Val Pro Glu Ser Gly Leu Arg Val Ser His Arg Lys Ala Leu Thr
                220                 225                 230 acc atc atc atc acc ttg atc atc ttc ttc ttg tgt ttc ctg ccc tat    1255
Thr Ile Ile Ile Thr Leu Ile Ile Phe Phe Leu Cys Phe Leu Pro Tyr
            235                 240                 245 cac aca ctg agg acc gtc cac ttg acg aca tgg aaa gtg ggt tta tgc    1303
His Thr Leu Arg Thr Val His Leu Thr Thr Trp Lys Val Gly Leu Cys
        250                 255                 260 aaa gac aga ctg cat aaa gct ttg gtt atc aca ctg gcc ttg gca gca    1351
Lys Asp Arg Leu His Lys Ala Leu Val Ile Thr Leu Ala Leu Ala Ala
265                 270                 275 gcc aat gcc tgc ttc aat cct ctg ctc tat tac ttt gct ggg gag aat    1399
Ala Asn Ala Cys Phe Asn Pro Leu Leu Tyr Tyr Phe Ala Gly Glu Asn
280                 285                 290                 295 ttt aag gac aga cta aag tct gca ctc aga aaa ggc cat cca cag aag    1447
Phe Lys Asp Arg Leu Lys Ser Ala Leu Arg Lys Gly His Pro Gln Lys
                300                 305                 310 gca aag aca aag tgt gtt ttc cct gtt agt gtg tgg ttg aga aag gaa    1495
Ala Lys Thr Lys Cys Val Phe Pro Val Ser Val Trp Leu Arg Lys Glu
            315                 320                 325 aca aga gta taaggagctc ttagatgaga cctgttcttg tatccttgtg            1544
Thr Arg Val
        330 tccatcttca ttcactcata gtctccaaat gactttgtat ttacatcact cccaacaaat  1604 gttgattctt aatatttagt tgaccattac ttttgttaat aagacctact tcaaaatttt  1664 tattcagtgt aaaaaaaaaa aaaaaaaaaa aaaaaaaaaa aaaa                   1708

<210> SEQ ID NO 2
<211> LENGTH: 330
<212> TYPE: PRT
<213> ORGANISM: homo sapiens

<400> SEQUENCE: 2

Met Glu Pro Asn Gly Thr Phe Ser Asn Asn Ser Arg Asn Cys Thr
1               5                   10                  15

Ile Glu Asn Phe Lys Arg Glu Phe Phe Pro Ile Val Tyr Leu Ile Ile
                20                  25                  30

Phe Phe Trp Gly Val Leu Gly Asn Gly Leu Ser Ile Tyr Val Phe Leu
            35                  40                  45

Gln Pro Tyr Lys Lys Ser Thr Ser Val Asn Val Phe Met Leu Asn Leu
    50                  55                  60

Ala Ile Ser Asp Leu Leu Phe Ile Ser Thr Leu Pro Phe Arg Ala Asp
65                  70                  75                  80

Tyr Tyr Leu Arg Gly Ser Asn Trp Ile Phe Gly Asp Leu Ala Cys Arg
                85                  90                  95

Ile Met Ser Tyr Ser Leu Tyr Val Asn Met Tyr Ser Ser Ile Tyr Phe
                100                 105                 110

Leu Thr Val Leu Ser Val Val Arg Phe Leu Ala Met Val His Pro Phe
            115                 120                 125

Arg Leu Leu His Val Thr Ser Ile Arg Ser Ala Trp Ile Leu Cys Gly
```

```
                130                 135                 140
Ile Ile Trp Ile Leu Ile Met Ala Ser Ser Ile Met Leu Leu Asp Ser
145                 150                 155                 160

Gly Ser Glu Gln Asn Gly Ser Val Thr Ser Cys Leu Glu Leu Asn Leu
                165                 170                 175

Tyr Lys Ile Ala Lys Leu Gln Thr Met Asn Tyr Ile Ala Leu Val Val
                180                 185                 190

Gly Cys Leu Leu Pro Phe Phe Thr Leu Ser Ile Cys Tyr Leu Leu Ile
                195                 200                 205

Ile Arg Val Leu Leu Lys Val Glu Val Pro Glu Ser Gly Leu Arg Val
210                 215                 220

Ser His Arg Lys Ala Leu Thr Thr Ile Ile Thr Leu Ile Ile Phe
225                 230                 235                 240

Phe Leu Cys Phe Leu Pro Tyr His Thr Leu Arg Thr Val His Leu Thr
                245                 250                 255

Thr Trp Lys Val Gly Leu Cys Lys Asp Arg Leu His Lys Ala Leu Val
                260                 265                 270

Ile Thr Leu Ala Leu Ala Ala Ala Asn Ala Cys Phe Asn Pro Leu Leu
                275                 280                 285

Tyr Tyr Phe Ala Gly Glu Asn Phe Lys Asp Arg Leu Lys Ser Ala Leu
                290                 295                 300

Arg Lys Gly His Pro Gln Lys Ala Lys Thr Lys Cys Val Phe Pro Val
305                 310                 315                 320

Ser Val Trp Leu Arg Lys Glu Thr Arg Val
                325                 330

<210> SEQ ID NO 3
<211> LENGTH: 362
<212> TYPE: PRT
<213> ORGANISM: homo sapiens

<400> SEQUENCE: 3

Met Thr Glu Ala Leu Ile Ser Ala Ala Leu Asn Gly Thr Gln Pro Glu
1               5                   10                  15

Leu Leu Ala Gly Gly Trp Ala Ala Gly Asn Ala Thr Thr Lys Cys Ser
                20                  25                  30

Leu Thr Lys Thr Gly Phe Gln Phe Tyr Tyr Leu Pro Thr Val Tyr Ile
                35                  40                  45

Leu Val Phe Ile Thr Gly Phe Leu Gly Asn Ser Val Ala Ile Trp Met
                50                  55                  60

Phe Val Phe His Met Arg Pro Trp Ser Gly Ile Ser Val Tyr Met Phe
65                  70                  75                  80

Asn Leu Ala Leu Ala Asp Phe Leu Tyr Val Leu Thr Leu Pro Ala Leu
                85                  90                  95

Ile Phe Tyr Tyr Phe Asn Lys Thr Asp Trp Ile Phe Gly Asp Val Met
                100                 105                 110

Cys Lys Leu Gln Arg Phe Ile Phe His Val Asn Leu Tyr Gly Ser Ile
                115                 120                 125

Leu Phe Leu Thr Cys Ile Ser Val His Arg Tyr Thr Gly Val Val His
                130                 135                 140

Pro Leu Lys Ser Leu Gly Arg Leu Lys Lys Lys Asn Ala Val Tyr Val
145                 150                 155                 160

Ser Ser Leu Val Trp Ala Leu Val Val Ala Val Ile Ala Pro Ile Leu
                165                 170                 175
```

```
Phe Tyr Ser Gly Thr Gly Val Arg Arg Asn Lys Thr Ile Thr Cys Tyr
            180                 185                 190

Asp Thr Thr Ala Asp Glu Tyr Leu Arg Ser Tyr Phe Val Tyr Ser Met
        195                 200                 205

Cys Thr Thr Val Phe Met Phe Cys Ile Pro Phe Ile Val Ile Leu Gly
        210                 215                 220

Cys Tyr Gly Leu Ile Val Lys Ala Leu Ile Tyr Lys Asp Leu Asp Asn
225                 230                 235                 240

Ser Pro Leu Arg Arg Lys Ser Ile Tyr Leu Val Ile Ile Val Leu Thr
            245                 250                 255

Val Phe Ala Val Ser Tyr Leu Pro Phe His Val Met Lys Thr Leu Asn
            260                 265                 270

Leu Arg Ala Arg Leu Asp Phe Gln Thr Pro Gln Met Cys Ala Phe Asn
            275                 280                 285

Asp Lys Val Tyr Ala Thr Tyr Gln Val Thr Arg Gly Leu Ala Ser Leu
        290                 295                 300

Asn Ser Cys Val Asp Pro Ile Leu Tyr Phe Leu Ala Gly Asp Thr Phe
305                 310                 315                 320

Arg Arg Arg Leu Ser Arg Ala Thr Arg Lys Ser Ser Arg Arg Ser Glu
            325                 330                 335

Pro Asn Val Gln Ser Lys Ser Glu Glu Met Thr Leu Asn Ile Leu Thr
            340                 345                 350

Glu Tyr Lys Gln Asn Gly Asp Thr Ser Leu
            355                 360

<210> SEQ ID NO 4
<211> LENGTH: 362
<212> TYPE: PRT
<213> ORGANISM: homo sapiens

<400> SEQUENCE: 4

Met Thr Glu Ala Leu Ile Ser Ala Ala Leu Asn Gly Thr Gln Pro Glu
1               5                   10                  15

Leu Leu Ala Gly Gly Trp Ala Gly Asn Ala Ser Thr Lys Cys Ser
            20                  25                  30

Leu Thr Lys Thr Gly Phe Gln Phe Tyr Tyr Leu Pro Thr Val Tyr Ile
            35                  40                  45

Leu Val Phe Ile Thr Gly Phe Leu Gly Asn Ser Val Ala Ile Trp Met
        50                  55                  60

Phe Val Phe His Met Arg Pro Trp Ser Gly Ile Ser Val Tyr Met Phe
65                  70                  75                  80

Asn Leu Ala Leu Ala Asp Phe Leu Tyr Val Leu Thr Leu Pro Ala Leu
                85                  90                  95

Ile Phe Tyr Tyr Phe Asn Lys Thr Asp Trp Ile Phe Gly Asp Val Met
            100                 105                 110

Cys Lys Leu Gln Arg Phe Ile Phe His Val Asn Leu Tyr Gly Ser Ile
        115                 120                 125

Leu Phe Leu Thr Cys Ile Ser Val His Arg Tyr Thr Gly Val Val His
        130                 135                 140

Pro Leu Lys Ser Leu Gly Arg Leu Lys Lys Asn Ala Val Tyr Val
145                 150                 155                 160

Ser Ser Leu Val Trp Ala Leu Val Val Ala Val Ile Ala Pro Ile Leu
                165                 170                 175

Phe Tyr Ser Gly Thr Gly Val Arg Arg Asn Lys Thr Ile Thr Cys Tyr
            180                 185                 190
```

```
Asp Thr Thr Ala Asp Glu Tyr Leu Arg Ser Tyr Phe Val Tyr Ser Met
            195                 200                 205

Cys Thr Thr Val Phe Met Phe Cys Ile Pro Phe Ile Val Ile Leu Gly
        210                 215                 220

Cys Tyr Gly Leu Ile Val Lys Ala Leu Ile Tyr Lys Asp Leu Asp Asn
225                 230                 235                 240

Ser Pro Leu Arg Arg Lys Ser Ile Tyr Leu Val Ile Ile Val Leu Thr
                245                 250                 255

Val Phe Ala Val Ser Tyr Leu Pro Phe His Val Met Lys Thr Leu Asn
            260                 265                 270

Leu Arg Ala Arg Leu Asp Phe Gln Thr Pro Gln Met Cys Ala Phe Asn
        275                 280                 285

Asp Lys Val Tyr Ala Thr Tyr Gln Val Thr Arg Gly Leu Ala Ser Leu
    290                 295                 300

Asn Ser Cys Val Asp Pro Ile Leu Tyr Phe Leu Ala Gly Asp Thr Phe
305                 310                 315                 320

Arg Arg Arg Leu Ser Arg Ala Thr Arg Lys Ser Ser Arg Arg Ser Glu
                325                 330                 335

Pro Asn Val Gln Ser Lys Ser Glu Glu Met Thr Leu Asn Ile Leu Thr
            340                 345                 350

Glu Tyr Lys Gln Asn Gly Asp Thr Ser Leu
        355                 360

<210> SEQ ID NO 5
<211> LENGTH: 373
<212> TYPE: PRT
<213> ORGANISM: homo sapiens

<400> SEQUENCE: 5

Met Thr Glu Val Pro Trp Ser Ala Val Pro Asn Gly Thr Asp Ala Ala
1               5                   10                  15

Phe Leu Ala Gly Leu Gly Ser Leu Trp Gly Asn Ser Thr Ile Ala Ser
            20                  25                  30

Thr Ala Val Ser Ser Ser Phe Arg Cys Ala Leu Ile Lys Thr Gly
        35                  40                  45

Phe Gln Phe Tyr Tyr Leu Pro Ala Val Tyr Ile Leu Val Phe Ile Ile
    50                  55                  60

Gly Phe Leu Gly Asn Ser Val Ala Ile Trp Met Phe Val Phe His Met
65                  70                  75                  80

Lys Pro Trp Ser Gly Ile Ser Val Tyr Met Phe Asn Leu Ala Leu Ala
                85                  90                  95

Asp Phe Leu Tyr Val Leu Thr Leu Pro Ala Leu Ile Phe Tyr Tyr Phe
            100                 105                 110

Asn Lys Thr Asp Trp Ile Phe Gly Asp Val Met Cys Lys Leu Gln Arg
        115                 120                 125

Phe Ile Phe His Val Asn Leu Tyr Gly Ser Ile Leu Phe Leu Thr Cys
    130                 135                 140

Ile Ser Ala His Arg Tyr Ser Gly Val Val Tyr Pro Leu Lys Ser Leu
145                 150                 155                 160

Gly Arg Leu Lys Lys Lys Asn Ala Ile Tyr Val Ser Val Leu Val Trp
                165                 170                 175

Leu Ile Val Val Val Ala Ile Ser Pro Ile Leu Phe Tyr Ser Gly Thr
            180                 185                 190

Gly Ile Arg Lys Asn Lys Thr Val Thr Cys Tyr Asp Ser Thr Ser Asp
```

```
                195                 200                 205
Glu Tyr Leu Arg Ser Tyr Phe Ile Tyr Ser Met Cys Thr Thr Val Ala
    210                 215                 220

Met Phe Cys Ile Pro Leu Val Leu Ile Leu Gly Cys Tyr Gly Leu Ile
225                 230                 235                 240

Val Arg Ala Leu Ile Tyr Lys Asp Leu Asp Asn Ser Pro Leu Arg Arg
                245                 250                 255

Lys Ser Ile Tyr Leu Val Ile Val Leu Thr Val Phe Ala Val Ser
                260                 265                 270

Tyr Ile Pro Phe His Val Met Lys Thr Met Asn Leu Arg Ala Arg Leu
                275                 280                 285

Asp Phe Gln Thr Pro Glu Met Cys Asp Phe Asn Asp Arg Val Tyr Ala
            290                 295                 300

Thr Tyr Gln Val Thr Arg Gly Leu Ala Ser Leu Asn Ser Cys Val Asp
305                 310                 315                 320

Pro Ile Leu Tyr Phe Leu Ala Gly Asp Thr Phe Arg Arg Arg Leu Ser
                325                 330                 335

Arg Ala Thr Arg Lys Ala Ser Arg Arg Ser Glu Ala Asn Leu Gln Ser
                340                 345                 350

Lys Ser Glu Glu Met Thr Leu Asn Ile Leu Ser Glu Phe Lys Gln Asn
                355                 360                 365

Gly Asp Thr Ser Leu
        370

<210> SEQ ID NO 6
<211> LENGTH: 337
<212> TYPE: PRT
<213> ORGANISM: homo sapiens

<400> SEQUENCE: 6

Met Asp Glu Thr Gly Asn Leu Thr Val Ser Ser Ala Thr Cys His Asp
1               5                   10                  15

Thr Ile Asp Asp Phe Arg Asn Gln Val Tyr Ser Thr Leu Tyr Ser Met
                20                  25                  30

Ile Ser Val Val Gly Phe Phe Gly Asn Gly Phe Val Leu Tyr Val Leu
            35                  40                  45

Ile Lys Thr Tyr His Lys Lys Ser Ala Phe Gln Val Tyr Met Ile Asn
        50                  55                  60

Leu Ala Val Ala Asp Leu Leu Cys Val Cys Thr Leu Pro Leu Arg Val
65                  70                  75                  80

Val Tyr Tyr Val His Lys Gly Ile Trp Leu Phe Gly Asp Phe Leu Cys
                85                  90                  95

Arg Leu Ser Thr Tyr Ala Leu Tyr Val Asn Leu Tyr Cys Ser Ile Phe
                100                 105                 110

Phe Met Thr Ala Met Ser Phe Phe Arg Cys Ile Ala Ile Val Phe Pro
            115                 120                 125

Val Gln Asn Ile Asn Leu Val Thr Gln Lys Lys Ala Arg Phe Val Cys
        130                 135                 140

Val Gly Ile Trp Ile Phe Val Ile Leu Thr Ser Ser Pro Phe Leu Met
145                 150                 155                 160

Ala Lys Pro Gln Lys Asp Glu Lys Asn Asn Thr Lys Cys Phe Glu Pro
                165                 170                 175

Pro Gln Asp Asn Gln Thr Lys Asn His Val Leu Val Leu His Tyr Val
                180                 185                 190
```

```
Ser Leu Phe Val Gly Phe Ile Ile Pro Phe Val Ile Ile Val Cys
        195                 200                 205

Tyr Thr Met Ile Ile Leu Thr Leu Leu Lys Lys Ser Met Lys Lys Asn
        210                 215                 220

Leu Ser Ser His Lys Lys Ala Ile Gly Met Ile Met Val Val Thr Ala
225                 230                 235                 240

Ala Phe Leu Val Ser Phe Met Pro Tyr His Ile Gln Arg Thr Ile His
                245                 250                 255

Leu His Phe Leu His Asn Glu Thr Lys Pro Cys Asp Ser Val Leu Arg
                260                 265                 270

Met Gln Lys Ser Val Val Ile Thr Leu Ser Leu Ala Ala Ser Asn Cys
        275                 280                 285

Cys Phe Asp Pro Leu Leu Tyr Phe Phe Ser Gly Gly Asn Phe Arg Lys
        290                 295                 300

Arg Leu Ser Thr Phe Arg Lys His Ser Leu Ser Ser Val Thr Tyr Val
305                 310                 315                 320

Pro Arg Lys Lys Ala Ser Leu Pro Glu Lys Gly Glu Ile Cys Lys
                325                 330                 335

Val

<210> SEQ ID NO 7
<211> LENGTH: 308
<212> TYPE: PRT
<213> ORGANISM: homo sapiens

<400> SEQUENCE: 7

Met Val Ser Ser Asn Cys Ser Thr Glu Asp Ser Phe Lys Tyr Thr Leu
1               5                   10                  15

Tyr Gly Cys Val Phe Ser Met Val Phe Val Leu Gly Leu Ile Ala Asn
                20                  25                  30

Cys Val Ala Ile Tyr Ile Phe Thr Phe Thr Leu Lys Val Arg Asn Glu
            35                  40                  45

Thr Thr Thr Tyr Met Leu Asn Leu Ala Ile Ser Asp Leu Leu Phe Val
        50                  55                  60

Phe Thr Leu Pro Phe Arg Ile Tyr Tyr Phe Val Val Arg Asn Trp Pro
65                  70                  75                  80

Phe Gly Asp Val Leu Cys Lys Ile Ser Val Thr Leu Phe Tyr Thr Asn
                85                  90                  95

Met Tyr Gly Ser Ile Leu Phe Leu Thr Cys Ile Ser Val Asp Arg Phe
                100                 105                 110

Leu Ala Ile Val His Pro Phe Arg Ser Lys Thr Leu Arg Thr Lys Arg
            115                 120                 125

Asn Ala Arg Ile Val Cys Val Ala Val Trp Ile Thr Val Leu Ala Gly
        130                 135                 140

Ser Thr Pro Ala Ser Phe Phe Gln Ser Thr Asn Arg Gln Asn Asn Thr
145                 150                 155                 160

Glu Gln Arg Thr Cys Phe Glu Asn Phe Pro Glu Ser Thr Trp Lys Thr
                165                 170                 175

Tyr Leu Ser Arg Ile Val Ile Phe Ile Glu Ile Val Gly Phe Phe Ile
            180                 185                 190

Pro Leu Ile Leu Asn Val Thr Cys Ser Thr Met Val Leu Arg Thr Leu
        195                 200                 205

Asn Lys Pro Leu Thr Leu Ser Arg Asn Lys Leu Ser Lys Lys Lys Val
        210                 215                 220
```

```
Leu Lys Met Ile Phe Val His Leu Val Ile Phe Cys Phe Cys Phe Val
225                 230                 235                 240

Pro Tyr Asn Ile Thr Leu Ile Leu Tyr Ser Leu Met Arg Thr Gln Thr
                245                 250                 255

Trp Ile Asn Cys Ser Val Val Thr Ala Val Arg Thr Met Tyr Pro Val
            260                 265                 270

Thr Leu Cys Ile Ala Val Ser Asn Cys Cys Phe Asp Pro Ile Val Tyr
        275                 280                 285

Tyr Phe Thr Ser Asp Thr Asn Ser Glu Leu Asp Lys Lys Gln Gln Val
    290                 295                 300

His Gln Asn Thr
305

<210> SEQ ID NO 8
<211> LENGTH: 339
<212> TYPE: PRT
<213> ORGANISM: homo sapiens

<400> SEQUENCE: 8

Met Asn Gly Leu Glu Val Ala Pro Pro Gly Leu Ile Thr Asn Phe Ser
1               5                   10                  15

Leu Ala Thr Ala Glu Gln Cys Gly Gln Glu Thr Pro Leu Glu Asn Met
            20                  25                  30

Leu Phe Ala Ser Phe Tyr Leu Leu Asp Phe Ile Leu Ala Leu Val Gly
        35                  40                  45

Asn Thr Leu Ala Leu Trp Leu Phe Ile Arg Asp His Lys Ser Gly Thr
    50                  55                  60

Pro Ala Asn Val Phe Leu Met His Leu Ala Val Ala Asp Leu Ser Cys
65                  70                  75                  80

Val Leu Val Leu Pro Thr Arg Leu Val Tyr His Phe Ser Gly Asn His
                85                  90                  95

Trp Pro Phe Gly Glu Ile Ala Cys Arg Leu Thr Gly Phe Leu Phe Tyr
            100                 105                 110

Leu Asn Met Tyr Ala Ser Ile Tyr Phe Leu Thr Cys Ile Ser Ala Asp
        115                 120                 125

Arg Phe Leu Ala Ile Val His Pro Val Lys Ser Leu Lys Leu Arg Arg
    130                 135                 140

Pro Leu Tyr Ala His Leu Ala Cys Ala Phe Leu Trp Val Val Val Ala
145                 150                 155                 160

Val Ala Met Ala Pro Leu Leu Val Ser Pro Gln Thr Val Gln Thr Asn
                165                 170                 175

His Thr Val Val Cys Leu Gln Leu Tyr Arg Glu Lys Ala Ser His His
            180                 185                 190

Ala Leu Val Ser Leu Ala Val Ala Phe Thr Phe Pro Phe Ile Thr Thr
        195                 200                 205

Val Thr Cys Tyr Leu Leu Ile Ile Arg Ser Leu Arg Gln Gly Leu Arg
    210                 215                 220

Val Glu Lys Arg Leu Lys Thr Lys Ala Val Arg Met Ile Ala Ile Val
225                 230                 235                 240

Leu Ala Ile Phe Leu Val Cys Phe Val Pro Tyr His Val Asn Arg Ser
                245                 250                 255

Val Tyr Val Leu His Tyr Arg Ser His Gly Ala Ser Cys Ala Thr Gln
            260                 265                 270

Arg Ile Leu Ala Leu Ala Asn Arg Ile Thr Ser Cys Leu Thr Ser Leu
        275                 280                 285
```

```
Asn Gly Ala Leu Asp Pro Ile Met Tyr Phe Phe Val Ala Glu Lys Phe
    290                 295                 300

Arg His Ala Leu Cys Asn Leu Leu Cys Gly Lys Arg Leu Lys Gly Pro
305                 310                 315                 320

Pro Pro Ser Phe Glu Gly Lys Thr Asn Glu Ser Ser Leu Ser Ala Lys
                325                 330                 335

Ser Glu Leu

<210> SEQ ID NO 9
<211> LENGTH: 80
<212> TYPE: DNA
<213> ORGANISM: homo sapiens

<400> SEQUENCE: 9
ttgggaaatg ggttgtccat atatgttttc ctgcagcctt ataagaagtc cacatctgtg      60
aacgttttca tgctaaatct                                                  80

<210> SEQ ID NO 10
<211> LENGTH: 20
<212> TYPE: DNA
<213> ORGANISM: homo sapiens

<400> SEQUENCE: 10
ggccatttca gatctcctgt                                                  20

<210> SEQ ID NO 11
<211> LENGTH: 20
<212> TYPE: DNA
<213> ORGANISM: homo sapiens

<400> SEQUENCE: 11
ctgaagggaa gcgtgcttat                                                  20

<210> SEQ ID NO 12
<211> LENGTH: 25
<212> TYPE: PRT
<213> ORGANISM: homo sapiens

<400> SEQUENCE: 12

Phe Phe Pro Ile Val Tyr Leu Ile Ile Phe Phe Trp Gly Val Leu Gly
1               5                   10                  15

Asn Gly Leu Ser Ile Tyr Val Phe Leu
            20                  25

<210> SEQ ID NO 13
<211> LENGTH: 25
<212> TYPE: PRT
<213> ORGANISM: homo sapiens

<400> SEQUENCE: 13

Val Phe Met Leu Asn Leu Ala Ile Ser Asp Leu Leu Phe Ile Ser Thr
1               5                   10                  15

Leu Pro Phe Arg Ala Asp Tyr Tyr Leu
            20                  25

<210> SEQ ID NO 14
<211> LENGTH: 22
<212> TYPE: PRT
<213> ORGANISM: homo sapiens

<400> SEQUENCE: 14
```

Val Asn Met Tyr Ser Ser Ile Tyr Phe Leu Thr Val Leu Ser Val Val
1               5                   10                  15

Arg Phe Leu Ala Met Val
            20

<210> SEQ ID NO 15
<211> LENGTH: 20
<212> TYPE: PRT
<213> ORGANISM: homo sapiens

<400> SEQUENCE: 15

Ala Trp Ile Leu Cys Gly Ile Ile Trp Ile Leu Ile Met Ala Ser Ser
1               5                   10                  15

Ile Met Leu Leu
            20

<210> SEQ ID NO 16
<211> LENGTH: 19
<212> TYPE: PRT
<213> ORGANISM: homo sapiens

<400> SEQUENCE: 16

Ile Ala Leu Val Val Gly Cys Leu Leu Pro Phe Phe Thr Leu Ser Ile
1               5                   10                  15

Cys Tyr Leu

<210> SEQ ID NO 17
<211> LENGTH: 22
<212> TYPE: PRT
<213> ORGANISM: homo sapiens

<400> SEQUENCE: 17

Ala Leu Thr Thr Ile Ile Ile Thr Leu Ile Ile Phe Phe Leu Cys Phe
1               5                   10                  15

Leu Pro Tyr His Thr Leu
            20

<210> SEQ ID NO 18
<211> LENGTH: 23
<212> TYPE: PRT
<213> ORGANISM: homo sapiens

<400> SEQUENCE: 18

Ala Leu Val Ile Thr Leu Ala Leu Ala Ala Asn Ala Cys Phe Asn
1               5                   10                  15

Pro Leu Leu Tyr Tyr Phe Ala
            20

<210> SEQ ID NO 19
<211> LENGTH: 13
<212> TYPE: PRT
<213> ORGANISM: homo sapiens

<400> SEQUENCE: 19

Leu Leu His Val Thr Ser Ile Arg Ser Ala Trp Ile Leu
1               5                   10

<210> SEQ ID NO 20
<211> LENGTH: 13
<212> TYPE: PRT
<213> ORGANISM: homo sapiens

```
<400> SEQUENCE: 20

Ser Gly Leu Arg Val Ser His Arg Lys Ala Leu Thr Thr
1               5                   10

<210> SEQ ID NO 21
<211> LENGTH: 13
<212> TYPE: PRT
<213> ORGANISM: homo sapiens

<400> SEQUENCE: 21

Phe Leu Pro Tyr His Thr Leu Arg Thr Val His Leu Thr
1               5                   10

<210> SEQ ID NO 22
<211> LENGTH: 13
<212> TYPE: PRT
<213> ORGANISM: homo sapiens

<400> SEQUENCE: 22

Thr Val His Leu Thr Thr Trp Lys Val Gly Leu Cys Lys
1               5                   10

<210> SEQ ID NO 23
<211> LENGTH: 12
<212> TYPE: PRT
<213> ORGANISM: homo sapiens

<400> SEQUENCE: 23

Met Glu Pro Asn Gly Thr Phe Ser Asn Asn Asn Ser
1               5                   10

<210> SEQ ID NO 24
<211> LENGTH: 14
<212> TYPE: PRT
<213> ORGANISM: homo sapiens

<400> SEQUENCE: 24

Gly Thr Phe Ser Asn Asn Asn Ser Arg Asn Cys Thr Ile Glu
1               5                   10

<210> SEQ ID NO 25
<211> LENGTH: 14
<212> TYPE: PRT
<213> ORGANISM: homo sapiens

<400> SEQUENCE: 25

Asn Asn Asn Ser Arg Asn Cys Thr Ile Glu Asn Phe Lys Arg
1               5                   10

<210> SEQ ID NO 26
<211> LENGTH: 14
<212> TYPE: PRT
<213> ORGANISM: homo sapiens

<400> SEQUENCE: 26

Ser Gly Ser Glu Gln Asn Gly Ser Val Thr Ser Cys Leu Glu
1               5                   10

<210> SEQ ID NO 27
<211> LENGTH: 733
<212> TYPE: DNA
<213> ORGANISM: homo sapiens

<400> SEQUENCE: 27
```

```
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agcctccca accccatcg    360 agaaaaccat ctccaaagcc aaagggcagc ccgagaacc acaggtgtac accctgcccc   420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                     733
```

```
<210> SEQ ID NO 28
<211> LENGTH: 8
<212> TYPE: PRT
<213> ORGANISM: bacteriophage T7

<400> SEQUENCE: 28

Asp Tyr Lys Asp Asp Asp Asp Lys
 1               5

<210> SEQ ID NO 29
<211> LENGTH: 1041
<212> TYPE: DNA
<213> ORGANISM: Homo sapiens
<220> FEATURE:
<221> NAME/KEY: CDS
<222> LOCATION: (1)..(1038)

<400> SEQUENCE: 29
```

```
atg gag aga aaa ttt atg tcc ttg caa cca tcc atc tcc gta tca gaa    48
Met Glu Arg Lys Phe Met Ser Leu Gln Pro Ser Ile Ser Val Ser Glu
 1               5                  10                  15 atg gaa cca aat ggc acc ttc agc aat aac aac agc agg aac tgc aca    96
Met Glu Pro Asn Gly Thr Phe Ser Asn Asn Asn Ser Arg Asn Cys Thr
                 20                  25                  30 att gaa aac ttc aag aga gaa ttt ttc cca att gta tat ctg ata ata   144
Ile Glu Asn Phe Lys Arg Glu Phe Phe Pro Ile Val Tyr Leu Ile Ile
             35                  40                  45 ttt ttc tgg gga gtc ttg gga aat ggg ttg tcc ata tat gtt ttc ctg   192
Phe Phe Trp Gly Val Leu Gly Asn Gly Leu Ser Ile Tyr Val Phe Leu
         50                  55                  60 cag cct tat aag aag tcc aca tct gtg aac gtt ttc atg cta aat ctg   240
Gln Pro Tyr Lys Lys Ser Thr Ser Val Asn Val Phe Met Leu Asn Leu
 65                  70                  75                  80 gcc att tca gat ctc ctg ttc ata agc acg ctt ccc ttc agg gct gac   288
Ala Ile Ser Asp Leu Leu Phe Ile Ser Thr Leu Pro Phe Arg Ala Asp
                 85                  90                  95 tat tat ctt aga ggc tcc aat tgg ata ttt gga gac ctg gcc tgc agg   336
Tyr Tyr Leu Arg Gly Ser Asn Trp Ile Phe Gly Asp Leu Ala Cys Arg
                100                 105                 110 att atg tct tat tcc ttg tat gtc aac atg tac agc agt att tat ttc   384
Ile Met Ser Tyr Ser Leu Tyr Val Asn Met Tyr Ser Ser Ile Tyr Phe
            115                 120                 125
```

-continued

| | |
|---|---|
| ctg acc gtg ctg agt gtt gtg cgt ttc ctg gca atg gtt cac ccc ttt<br>Leu Thr Val Leu Ser Val Val Arg Phe Leu Ala Met Val His Pro Phe<br>130                         135                     140 | 432 |
| cgg ctt ctg cat gtc acc agc atc agg agt gcc tgg atc ctc tgt ggg<br>Arg Leu Leu His Val Thr Ser Ile Arg Ser Ala Trp Ile Leu Cys Gly<br>145                       150                      155                   160 | 480 |
| atc ata tgg atc ctt atc atg gct tcc tca ata atg ctc ctg gac agt<br>Ile Ile Trp Ile Leu Ile Met Ala Ser Ser Ile Met Leu Leu Asp Ser<br>                    165                     170                   175 | 528 |
| ggc tct gag cag aac ggc agt gtc aca tca tgc tta gag ctg aat ctc<br>Gly Ser Glu Gln Asn Gly Ser Val Thr Ser Cys Leu Glu Leu Asn Leu<br>        180                       185                     190 | 576 |
| tat aaa att gct aag ctg cag acc atg aac tat att gcc ttg gtg gtg<br>Tyr Lys Ile Ala Lys Leu Gln Thr Met Asn Tyr Ile Ala Leu Val Val<br>195                       200                     205 | 624 |
| ggc tgc ctg ctg cca ttt ttc aca ctc agc atc tgt tat ctg ctg atc<br>Gly Cys Leu Leu Pro Phe Phe Thr Leu Ser Ile Cys Tyr Leu Leu Ile<br>210                       215                     220 | 672 |
| att cgg gtt ctg tta aaa gtg gag gtc cca gaa tcg ggg ctg cgg gtt<br>Ile Arg Val Leu Leu Lys Val Glu Val Pro Glu Ser Gly Leu Arg Val<br>225                       230                     235                   240 | 720 |
| tct cac agg aag gca ctg acc acc atc atc atc acc ttg atc atc ttc<br>Ser His Arg Lys Ala Leu Thr Thr Ile Ile Ile Thr Leu Ile Ile Phe<br>                    245                     250                   255 | 768 |
| ttc ttg tgt ttc ctg ccc tat cac aca ctg agg acc gtc cac ttg acg<br>Phe Leu Cys Phe Leu Pro Tyr His Thr Leu Arg Thr Val His Leu Thr<br>        260                       265                     270 | 816 |
| aca tgg aaa gtg ggt tta tgc aaa gac aga ctg cat aaa gct ttg gtt<br>Thr Trp Lys Val Gly Leu Cys Lys Asp Arg Leu His Lys Ala Leu Val<br>275                       280                     285 | 864 |
| atc aca ctg gcc ttg gca gca gcc aat gcc tgc ttc aat cct ctg ctc<br>Ile Thr Leu Ala Leu Ala Ala Ala Asn Ala Cys Phe Asn Pro Leu Leu<br>290                       295                     300 | 912 |
| tat tac ttt gct ggg gag aat ttt aag gac aga cta aag tct gca ctc<br>Tyr Tyr Phe Ala Gly Glu Asn Phe Lys Asp Arg Leu Lys Ser Ala Leu<br>305                       310                     315                   320 | 960 |
| aga aaa ggc cat cca cag aag gca aag aca aag tgt gtt ttc cct gtt<br>Arg Lys Gly His Pro Gln Lys Ala Lys Thr Lys Cys Val Phe Pro Val<br>                    325                     330                   335 | 1008 |
| agt gtg tgg ttg aga aag gaa aca aga gta taa<br>Ser Val Trp Leu Arg Lys Glu Thr Arg Val<br>340                       345 | 1041 |

<210> SEQ ID NO 30
<211> LENGTH: 346
<212> TYPE: PRT
<213> ORGANISM: Homo sapiens

<400> SEQUENCE: 30

Met Glu Arg Lys Phe Met Ser Leu Gln Pro Ser Ile Ser Val Ser Glu
1               5                   10                 15

Met Glu Pro Asn Gly Thr Phe Ser Asn Asn Ser Arg Asn Cys Thr
                20                   25                   30

Ile Glu Asn Phe Lys Arg Glu Phe Phe Pro Ile Val Tyr Leu Ile Ile
                    35                   40                   45

Phe Phe Trp Gly Val Leu Gly Asn Gly Leu Ser Ile Tyr Val Phe Leu
    50                   55                   60

Gln Pro Tyr Lys Lys Ser Thr Ser Val Asn Val Phe Met Leu Asn Leu
65                  70                   75                   80

```
Ala Ile Ser Asp Leu Leu Phe Ile Ser Thr Leu Pro Phe Arg Ala Asp
                85                  90                  95

Tyr Tyr Leu Arg Gly Ser Asn Trp Ile Phe Gly Asp Leu Ala Cys Arg
            100                 105                 110

Ile Met Ser Tyr Ser Leu Tyr Val Asn Met Tyr Ser Ser Ile Tyr Phe
        115                 120                 125

Leu Thr Val Leu Ser Val Val Arg Phe Leu Ala Met Val His Pro Phe
    130                 135                 140

Arg Leu Leu His Val Thr Ser Ile Arg Ser Ala Trp Ile Leu Cys Gly
145                 150                 155                 160

Ile Ile Trp Ile Leu Ile Met Ala Ser Ser Ile Met Leu Leu Asp Ser
                165                 170                 175

Gly Ser Glu Gln Asn Gly Ser Val Thr Ser Cys Leu Glu Leu Asn Leu
            180                 185                 190

Tyr Lys Ile Ala Lys Leu Gln Thr Met Asn Tyr Ile Ala Leu Val Val
        195                 200                 205

Gly Cys Leu Leu Pro Phe Phe Thr Leu Ser Ile Cys Tyr Leu Leu Ile
    210                 215                 220

Ile Arg Val Leu Leu Lys Val Glu Val Pro Glu Ser Gly Leu Arg Val
225                 230                 235                 240

Ser His Arg Lys Ala Leu Thr Thr Ile Ile Thr Leu Ile Ile Phe
                245                 250                 255

Phe Leu Cys Phe Leu Pro Tyr His Thr Leu Arg Thr Val His Leu Thr
            260                 265                 270

Thr Trp Lys Val Gly Leu Cys Lys Asp Arg Leu His Lys Ala Leu Val
        275                 280                 285

Ile Thr Leu Ala Leu Ala Ala Asn Ala Cys Phe Asn Pro Leu Leu
    290                 295                 300

Tyr Tyr Phe Ala Gly Glu Asn Phe Lys Asp Arg Leu Lys Ser Ala Leu
305                 310                 315                 320

Arg Lys Gly His Pro Gln Lys Ala Lys Thr Lys Cys Val Phe Pro Val
                325                 330                 335

Ser Val Trp Leu Arg Lys Glu Thr Arg Val
            340                 345

<210> SEQ ID NO 31
<211> LENGTH: 25
<212> TYPE: PRT
<213> ORGANISM: Homo sapiens

<400> SEQUENCE: 31

Phe Phe Pro Ile Val Tyr Leu Ile Ile Phe Phe Trp Gly Val Leu Gly
1               5                   10                  15

Asn Gly Leu Ser Ile Tyr Val Phe Leu
            20                  25

<210> SEQ ID NO 32
<211> LENGTH: 25
<212> TYPE: PRT
<213> ORGANISM: Homo sapiens

<400> SEQUENCE: 32

Val Phe Met Leu Asn Leu Ala Ile Ser Asp Leu Leu Phe Ile Ser Thr
1               5                   10                  15

Leu Pro Phe Arg Ala Asp Tyr Tyr Leu
            20                  25
```

<210> SEQ ID NO 33
<211> LENGTH: 22
<212> TYPE: PRT
<213> ORGANISM: Homo sapiens

<400> SEQUENCE: 33

Val Asn Met Tyr Ser Ser Ile Tyr Phe Leu Thr Val Leu Ser Val Val
1               5                   10                  15

Arg Phe Leu Ala Met Val
            20

<210> SEQ ID NO 34
<211> LENGTH: 20
<212> TYPE: PRT
<213> ORGANISM: Homo sapiens

<400> SEQUENCE: 34

Ala Trp Ile Leu Cys Gly Ile Ile Trp Ile Leu Ile Met Ala Ser Ser
1               5                   10                  15

Ile Met Leu Leu
            20

<210> SEQ ID NO 35
<211> LENGTH: 28
<212> TYPE: PRT
<213> ORGANISM: Homo sapiens

<400> SEQUENCE: 35

Ile Ala Lys Leu Gln Thr Met Asn Tyr Ile Ala Leu Val Val Gly Cys
1               5                   10                  15

Leu Leu Pro Phe Phe Thr Leu Ser Ile Cys Tyr Leu
            20                  25

<210> SEQ ID NO 36
<211> LENGTH: 22
<212> TYPE: PRT
<213> ORGANISM: Homo sapiens

<400> SEQUENCE: 36

Ala Leu Thr Thr Ile Ile Ile Thr Leu Ile Ile Phe Phe Leu Cys Phe
1               5                   10                  15

Leu Pro Tyr His Thr Leu
            20

<210> SEQ ID NO 37
<211> LENGTH: 23
<212> TYPE: PRT
<213> ORGANISM: Homo sapiens

<400> SEQUENCE: 37

Ala Leu Val Ile Thr Leu Ala Leu Ala Ala Ala Asn Ala Cys Phe Asn
1               5                   10                  15

Pro Leu Leu Tyr Tyr Phe Ala
            20

<210> SEQ ID NO 38
<211> LENGTH: 13
<212> TYPE: PRT
<213> ORGANISM: Homo sapiens

<400> SEQUENCE: 38

```
Leu Leu His Val Thr Ser Ile Arg Ser Ala Trp Ile Leu
1               5                   10
```

<210> SEQ ID NO 39
<211> LENGTH: 13
<212> TYPE: PRT
<213> ORGANISM: Homo sapiens

<400> SEQUENCE: 39

```
Ser Gly Leu Arg Val Ser His Arg Lys Ala Leu Thr Thr
1               5                   10
```

<210> SEQ ID NO 40
<211> LENGTH: 13
<212> TYPE: PRT
<213> ORGANISM: Homo sapiens

<400> SEQUENCE: 40

```
Phe Leu Pro Tyr His Thr Leu Arg Thr Val His Leu Thr
1               5                   10
```

<210> SEQ ID NO 41
<211> LENGTH: 13
<212> TYPE: PRT
<213> ORGANISM: Homo sapiens

<400> SEQUENCE: 41

```
Thr Val His Leu Thr Thr Trp Lys Val Gly Leu Cys Lys
1               5                   10
```

<210> SEQ ID NO 42
<211> LENGTH: 14
<212> TYPE: PRT
<213> ORGANISM: Homo sapiens

<400> SEQUENCE: 42

```
Ser Glu Met Glu Pro Asn Gly Thr Phe Ser Asn Asn Asn Ser
1               5                   10
```

<210> SEQ ID NO 43
<211> LENGTH: 14
<212> TYPE: PRT
<213> ORGANISM: Homo sapiens

<400> SEQUENCE: 43

```
Gly Thr Phe Ser Asn Asn Asn Ser Arg Asn Cys Thr Ile Glu
1               5                   10
```

<210> SEQ ID NO 44
<211> LENGTH: 14
<212> TYPE: PRT
<213> ORGANISM: Homo sapiens

<400> SEQUENCE: 44

```
Asn Asn Asn Ser Arg Asn Cys Thr Ile Glu Asn Phe Lys Arg
1               5                   10
```

<210> SEQ ID NO 45
<211> LENGTH: 14
<212> TYPE: PRT
<213> ORGANISM: Homo sapiens

<400> SEQUENCE: 45

```
Ser Gly Ser Glu Gln Asn Gly Ser Val Thr Ser Cys Leu Glu
1               5                   10
```

<210> SEQ ID NO 46
<211> LENGTH: 38
<212> TYPE: DNA
<213> ORGANISM: Homo sapiens

<400> SEQUENCE: 46
gcagcagcgg ccgcgaattt ttcccaattg tatatctg             38

<210> SEQ ID NO 47
<211> LENGTH: 37
<212> TYPE: DNA
<213> ORGANISM: Homo sapiens

<400> SEQUENCE: 47
gcagcagtcg acttatactc ttgtttcctt tctcaac              37

<210> SEQ ID NO 48
<211> LENGTH: 38
<212> TYPE: DNA
<213> ORGANISM: Homo sapiens

<400> SEQUENCE: 48
gcagcagcgg ccgcatggaa ccaaatggca ccttcagc             38

<210> SEQ ID NO 49
<211> LENGTH: 36
<212> TYPE: DNA
<213> ORGANISM: Homo sapiens

<400> SEQUENCE: 49
gcagcagtcg accccagcaa agtaatagag cagagg               36

<210> SEQ ID NO 50
<211> LENGTH: 38
<212> TYPE: DNA
<213> ORGANISM: Homo sapiens

<400> SEQUENCE: 50
gcagcagcgg ccgcgaattt ttcccaattg tatatctg             38

<210> SEQ ID NO 51
<211> LENGTH: 37
<212> TYPE: DNA
<213> ORGANISM: Homo sapiens

<400> SEQUENCE: 51
gcagcagtcg actactcttg tttcctttct caaccac              37

<210> SEQ ID NO 52
<211> LENGTH: 39
<212> TYPE: DNA
<213> ORGANISM: Homo sapiens

<400> SEQUENCE: 52
gcagcagcgg ccgcatggag agaaaattta tgtccttgc            39

<210> SEQ ID NO 53
<211> LENGTH: 36
<212> TYPE: DNA
<213> ORGANISM: Homo sapiens

<400> SEQUENCE: 53

```
<210> SEQ ID NO 54
<211> LENGTH: 1026
<212> TYPE: DNA
<213> ORGANISM: Homo sapiens
<220> FEATURE:
<221> NAME/KEY: CDS
<222> LOCATION: (1)..(1023)

<400> SEQUENCE: 54
```

| | | | | | | | | | | | | | | | | |
|---|---|---|---|---|---|---|---|---|---|---|---|---|---|---|---|---|
| atg | tcc | ttg | caa | cca | tcc | atc | tcc | gta | tca | gaa | atg | gaa | cca | aat | ggc | 48 |
| Met | Ser | Leu | Gln | Pro | Ser | Ile | Ser | Val | Ser | Glu | Met | Glu | Pro | Asn | Gly | |
| 1 | | | | 5 | | | | | 10 | | | | | 15 | | |
| acc | ttc | agc | aat | aac | aac | agc | agg | aac | tgc | aca | att | gaa | aac | ttc | aag | 96 |
| Thr | Phe | Ser | Asn | Asn | Asn | Ser | Arg | Asn | Cys | Thr | Ile | Glu | Asn | Phe | Lys | |
| | | | | 20 | | | | | 25 | | | | | 30 | | |
| aga | gaa | ttt | ttc | cca | att | gta | tat | ctg | ata | ata | ttt | ttc | tgg | gga | gtc | 144 |
| Arg | Glu | Phe | Phe | Pro | Ile | Val | Tyr | Leu | Ile | Ile | Phe | Phe | Trp | Gly | Val | |
| | | 35 | | | | | 40 | | | | | 45 | | | | |
| ttg | gga | aat | ggg | ttg | tcc | ata | tat | gtt | ttc | ctg | cag | cct | tat | aag | aag | 192 |
| Leu | Gly | Asn | Gly | Leu | Ser | Ile | Tyr | Val | Phe | Leu | Gln | Pro | Tyr | Lys | Lys | |
| 50 | | | | | 55 | | | | | 60 | | | | | | |
| tcc | aca | tct | gtg | aac | gtt | ttc | atg | cta | aat | ctg | gcc | att | tca | gat | ctc | 240 |
| Ser | Thr | Ser | Val | Asn | Val | Phe | Met | Leu | Asn | Leu | Ala | Ile | Ser | Asp | Leu | |
| 65 | | | | | 70 | | | | | 75 | | | | | 80 | |
| ctg | ttc | ata | agc | acg | ctt | ccc | ttc | agg | gct | gac | tat | tat | ctt | aga | ggc | 288 |
| Leu | Phe | Ile | Ser | Thr | Leu | Pro | Phe | Arg | Ala | Asp | Tyr | Tyr | Leu | Arg | Gly | |
| | | | | 85 | | | | | 90 | | | | | 95 | | |
| tcc | aat | tgg | ata | ttt | gga | gac | ctg | gcc | tgc | agg | att | atg | tct | tat | tcc | 336 |
| Ser | Asn | Trp | Ile | Phe | Gly | Asp | Leu | Ala | Cys | Arg | Ile | Met | Ser | Tyr | Ser | |
| | | | | 100 | | | | | 105 | | | | | 110 | | |
| ttg | tat | gtc | aac | atg | tac | agc | agt | att | tat | ttc | ctg | acc | gtg | ctg | agt | 384 |
| Leu | Tyr | Val | Asn | Met | Tyr | Ser | Ser | Ile | Tyr | Phe | Leu | Thr | Val | Leu | Ser | |
| | | | | | 115 | | | | | 120 | | | | | 125 | |
| gtt | gtg | cgt | ttc | ctg | gca | atg | gtt | cac | ccc | ttt | cgg | ctt | ctg | cat | gtc | 432 |
| Val | Val | Arg | Phe | Leu | Ala | Met | Val | His | Pro | Phe | Arg | Leu | Leu | His | Val | |
| | | | 130 | | | | | 135 | | | | | 140 | | | |
| acc | agc | atc | agg | agt | gcc | tgg | atc | ctc | tgt | ggg | atc | ata | tgg | atc | ctt | 480 |
| Thr | Ser | Ile | Arg | Ser | Ala | Trp | Ile | Leu | Cys | Gly | Ile | Ile | Trp | Ile | Leu | |
| 145 | | | | | 150 | | | | | 155 | | | | | 160 | |
| atc | atg | gct | tcc | tca | ata | atg | ctc | ctg | gac | agt | ggc | tct | gag | cag | aac | 528 |
| Ile | Met | Ala | Ser | Ser | Ile | Met | Leu | Leu | Asp | Ser | Gly | Ser | Glu | Gln | Asn | |
| | | | | 165 | | | | | 170 | | | | | 175 | | |
| ggc | agt | gtc | aca | tca | tgc | tta | gag | ctg | aat | ctc | tat | aaa | att | gct | aag | 576 |
| Gly | Ser | Val | Thr | Ser | Cys | Leu | Glu | Leu | Asn | Leu | Tyr | Lys | Ile | Ala | Lys | |
| | | | | | 180 | | | | | 185 | | | | | 190 | |
| ctg | cag | acc | atg | aac | tat | att | gcc | ttg | gtg | gtg | ggc | tgc | ctg | ctg | cca | 624 |
| Leu | Gln | Thr | Met | Asn | Tyr | Ile | Ala | Leu | Val | Val | Gly | Cys | Leu | Leu | Pro | |
| | | | 195 | | | | | 200 | | | | | 205 | | | |
| ttt | ttc | aca | ctc | agc | atc | tgt | tat | ctg | ctg | atc | att | cgg | gtt | ctg | tta | 672 |
| Phe | Phe | Thr | Leu | Ser | Ile | Cys | Tyr | Leu | Leu | Ile | Ile | Arg | Val | Leu | Leu | |
| | | 210 | | | | | 215 | | | | | 220 | | | | |
| aaa | gtg | gag | gtc | cca | gaa | tcg | ggg | ctg | cgg | gtt | tct | cac | agg | aag | gca | 720 |
| Lys | Val | Glu | Val | Pro | Glu | Ser | Gly | Leu | Arg | Val | Ser | His | Arg | Lys | Ala | |
| 225 | | | | | 230 | | | | | 235 | | | | | 240 | |
| ctg | acc | acc | atc | atc | atc | acc | ttg | atc | atc | ttc | ttc | ttg | tgt | ttc | ctg | 768 |
| Leu | Thr | Thr | Ile | Ile | Ile | Thr | Leu | Ile | Ile | Phe | Phe | Leu | Cys | Phe | Leu | |
| | | | | 245 | | | | | 250 | | | | | 255 | | |
| ccc | tat | cac | aca | ctg | agg | acc | gtc | cac | ttg | acg | aca | tgg | aaa | gtg | ggt | 816 |
| Pro | Tyr | His | Thr | Leu | Arg | Thr | Val | His | Leu | Thr | Thr | Trp | Lys | Val | Gly | |

```
                260                 265                 270
tta tgc aaa gac aga ctg cat aaa gct ttg gtt atc aca ctg gcc ttg        864
Leu Cys Lys Asp Arg Leu His Lys Ala Leu Val Ile Thr Leu Ala Leu
        275                 280                 285 gca gcc aat gcc tgc ttc aat cct ctg ctc tat tac ttt gct ggg            912
Ala Ala Asn Ala Cys Phe Asn Pro Leu Leu Tyr Tyr Phe Ala Gly
    290                 295                 300 gag aat ttt aag gac aga cta aag tct gca ctc aga aaa ggc cat cca        960
Glu Asn Phe Lys Asp Arg Leu Lys Ser Ala Leu Arg Lys Gly His Pro
305                 310                 315                 320 cag aag gca aag aca aag tgt gtt ttc cct gtt agt gtg tgg ttg aga       1008
Gln Lys Ala Lys Thr Lys Cys Val Phe Pro Val Ser Val Trp Leu Arg
                325                 330                 335 aag gaa aca aga gta taa                                                1026
Lys Glu Thr Arg Val
            340

<210> SEQ ID NO 55
<211> LENGTH: 341
<212> TYPE: PRT
<213> ORGANISM: Homo sapiens

<400> SEQUENCE: 55

Met Ser Leu Gln Pro Ser Ile Ser Val Ser Glu Met Glu Pro Asn Gly
1               5                   10                  15

Thr Phe Ser Asn Asn Ser Arg Asn Cys Thr Ile Glu Asn Phe Lys
                20                  25                  30

Arg Glu Phe Phe Pro Ile Val Tyr Leu Ile Ile Phe Phe Trp Gly Val
            35                  40                  45

Leu Gly Asn Gly Leu Ser Ile Tyr Val Phe Leu Gln Pro Tyr Lys Lys
        50                  55                  60

Ser Thr Ser Val Asn Val Phe Met Leu Asn Leu Ala Ile Ser Asp Leu
65                  70                  75                  80

Leu Phe Ile Ser Thr Leu Pro Phe Arg Ala Asp Tyr Tyr Leu Arg Gly
                85                  90                  95

Ser Asn Trp Ile Phe Gly Asp Leu Ala Cys Arg Ile Met Ser Tyr Ser
            100                 105                 110

Leu Tyr Val Asn Met Tyr Ser Ser Ile Tyr Phe Leu Thr Val Leu Ser
        115                 120                 125

Val Val Arg Phe Leu Ala Met Val His Pro Phe Arg Leu Leu His Val
    130                 135                 140

Thr Ser Ile Arg Ser Ala Trp Ile Leu Cys Gly Ile Ile Trp Ile Leu
145                 150                 155                 160

Ile Met Ala Ser Ser Ile Met Leu Leu Asp Ser Gly Ser Glu Gln Asn
                165                 170                 175

Gly Ser Val Thr Ser Cys Leu Glu Leu Asn Leu Tyr Lys Ile Ala Lys
            180                 185                 190

Leu Gln Thr Met Asn Tyr Ile Ala Leu Val Val Gly Cys Leu Leu Pro
        195                 200                 205

Phe Phe Thr Leu Ser Ile Cys Tyr Leu Leu Ile Ile Arg Val Leu Leu
    210                 215                 220

Lys Val Glu Val Pro Glu Ser Gly Leu Arg Val Ser His Arg Lys Ala
225                 230                 235                 240

Leu Thr Thr Ile Ile Ile Thr Leu Ile Ile Phe Phe Leu Cys Phe Leu
                245                 250                 255

Pro Tyr His Thr Leu Arg Thr Val His Leu Thr Thr Trp Lys Val Gly
```

```
                    260                 265                 270
Leu Cys Lys Asp Arg Leu His Lys Ala Leu Val Ile Thr Leu Ala Leu
                275                 280                 285

Ala Ala Ala Asn Ala Cys Phe Asn Pro Leu Leu Tyr Tyr Phe Ala Gly
            290                 295                 300

Glu Asn Phe Lys Asp Arg Leu Lys Ser Ala Leu Arg Lys Gly His Pro
305                 310                 315                 320

Gln Lys Ala Lys Thr Lys Cys Val Phe Pro Val Ser Val Trp Leu Arg
                325                 330                 335

Lys Glu Thr Arg Val
            340

<210> SEQ ID NO 56
<211> LENGTH: 14
<212> TYPE: PRT
<213> ORGANISM: Homo sapiens

<400> SEQUENCE: 56

Phe Leu Gln Pro Tyr Lys Lys Ser Thr Ser Val Asn Val Phe
1               5                   10

<210> SEQ ID NO 57
<211> LENGTH: 11
<212> TYPE: PRT
<213> ORGANISM: Homo sapiens

<400> SEQUENCE: 57

Val Ser Val Trp Leu Arg Lys Glu Thr Arg Val
1               5                   10

<210> SEQ ID NO 58
<211> LENGTH: 14
<212> TYPE: PRT
<213> ORGANISM: Homo sapiens

<400> SEQUENCE: 58

Ile Met Leu Leu Asp Ser Gly Ser Glu Gln Asn Gly Ser Val
1               5                   10

<210> SEQ ID NO 59
<211> LENGTH: 14
<212> TYPE: PRT
<213> ORGANISM: Homo sapiens

<400> SEQUENCE: 59

Asn Gly Ser Val Thr Ser Cys Leu Glu Leu Asn Leu Tyr Lys
1               5                   10

<210> SEQ ID NO 60
<211> LENGTH: 15
<212> TYPE: PRT
<213> ORGANISM: Homo sapiens

<400> SEQUENCE: 60

Met Glu Pro Asn Gly Thr Phe Ser Asn Asn Ser Arg Asn Cys
1               5                   10              15

<210> SEQ ID NO 61
<211> LENGTH: 16
<212> TYPE: PRT
<213> ORGANISM: Homo sapiens

<400> SEQUENCE: 61
```

```
Ile Ile Phe Phe Trp Gly Val Leu Gly Asn Gly Leu Ser Ile Tyr Val
1               5                  10                  15
```

<210> SEQ ID NO 62
<211> LENGTH: 16
<212> TYPE: PRT
<213> ORGANISM: Homo sapiens

<400> SEQUENCE: 62

```
Phe Trp Gly Val Leu Gly Asn Gly Leu Ser Ile Tyr Val Phe Leu Gln
1               5                  10                  15
```

<210> SEQ ID NO 63
<211> LENGTH: 16
<212> TYPE: PRT
<213> ORGANISM: Homo sapiens

<400> SEQUENCE: 63

```
Met Leu Leu Asp Ser Gly Ser Glu Gln Asn Gly Ser Val Thr Ser Cys
1               5                  10                  15
```

<210> SEQ ID NO 64
<211> LENGTH: 16
<212> TYPE: PRT
<213> ORGANISM: Homo sapiens

<400> SEQUENCE: 64

```
Gly Ser Glu Gln Asn Gly Ser Val Thr Ser Cys Leu Glu Leu Asn Leu
1               5                  10                  15
```

<210> SEQ ID NO 65
<211> LENGTH: 16
<212> TYPE: PRT
<213> ORGANISM: Homo sapiens

<400> SEQUENCE: 65

```
Glu Val Pro Glu Ser Gly Leu Arg Val Ser His Arg Lys Ala Leu Thr
1               5                  10                  15
```

<210> SEQ ID NO 66
<211> LENGTH: 14
<212> TYPE: PRT
<213> ORGANISM: Homo sapiens

<400> SEQUENCE: 66

```
Phe Leu Gln Pro Tyr Lys Lys Ser Thr Ser Val Asn Val Phe
1               5                  10
```

<210> SEQ ID NO 67
<211> LENGTH: 11
<212> TYPE: PRT
<213> ORGANISM: Homo sapiens

<400> SEQUENCE: 67

```
Val Ser Val Trp Leu Arg Lys Glu Thr Arg Val
1               5                  10
```

<210> SEQ ID NO 68
<211> LENGTH: 14
<212> TYPE: PRT
<213> ORGANISM: Homo sapiens

<400> SEQUENCE: 68

```
Leu Gln Pro Ser Ile Ser Val Ser Glu Met Glu Pro Asn Gly
```

-continued

```
1               5                   10

<210> SEQ ID NO 69
<211> LENGTH: 14
<212> TYPE: PRT
<213> ORGANISM: Homo sapiens

<400> SEQUENCE: 69

Pro Ser Ile Ser Val Ser Glu Met Glu Pro Asn Gly Thr Phe
1               5                   10

<210> SEQ ID NO 70
<211> LENGTH: 14
<212> TYPE: PRT
<213> ORGANISM: Homo sapiens

<400> SEQUENCE: 70

Ile Met Leu Leu Asp Ser Gly Ser Glu Gln Asn Gly Ser Val
1               5                   10

<210> SEQ ID NO 71
<211> LENGTH: 14
<212> TYPE: PRT
<213> ORGANISM: Homo sapiens

<400> SEQUENCE: 71

Asn Gly Ser Val Thr Ser Cys Leu Glu Leu Asn Leu Tyr Lys
1               5                   10

<210> SEQ ID NO 72
<211> LENGTH: 15
<212> TYPE: PRT
<213> ORGANISM: Homo sapiens

<400> SEQUENCE: 72

Met Glu Pro Asn Gly Thr Phe Ser Asn Asn Ser Arg Asn Cys
1               5                   10                  15

<210> SEQ ID NO 73
<211> LENGTH: 16
<212> TYPE: PRT
<213> ORGANISM: Homo sapiens

<400> SEQUENCE: 73

Ile Ile Phe Phe Trp Gly Val Leu Gly Asn Gly Leu Ser Ile Tyr Val
1               5                   10                  15

<210> SEQ ID NO 74
<211> LENGTH: 16
<212> TYPE: PRT
<213> ORGANISM: Homo sapiens

<400> SEQUENCE: 74

Phe Trp Gly Val Leu Gly Asn Gly Leu Ser Ile Tyr Val Phe Leu Gln
1               5                   10                  15

<210> SEQ ID NO 75
<211> LENGTH: 16
<212> TYPE: PRT
<213> ORGANISM: Homo sapiens

<400> SEQUENCE: 75

Met Leu Leu Asp Ser Gly Ser Glu Gln Asn Gly Ser Val Thr Ser Cys
1               5                   10                  15
```

<210> SEQ ID NO 76
<211> LENGTH: 16
<212> TYPE: PRT
<213> ORGANISM: Homo sapiens

<400> SEQUENCE: 76

Gly Ser Glu Gln Asn Gly Ser Val Thr Ser Cys Leu Glu Leu Asn Leu
1               5                   10                  15

<210> SEQ ID NO 77
<211> LENGTH: 16
<212> TYPE: PRT
<213> ORGANISM: Homo sapiens

<400> SEQUENCE: 77

Glu Val Pro Glu Ser Gly Leu Arg Val Ser His Arg Lys Ala Leu Thr
1               5                   10                  15

<210> SEQ ID NO 78
<211> LENGTH: 36
<212> TYPE: DNA
<213> ORGANISM: Homo sapiens

<400> SEQUENCE: 78
ccgctagcgc atggaaaatg gcaccttcag caataa                          36

<210> SEQ ID NO 79
<211> LENGTH: 37
<212> TYPE: DNA
<213> ORGANISM: Homo sapiens

<400> SEQUENCE: 79
cggcggccgc ttatactctt gtttcctttc tcaacca                         37

<210> SEQ ID NO 80
<211> LENGTH: 26
<212> TYPE: DNA
<213> ORGANISM: Artificial Sequence
<220> FEATURE:
<223> OTHER INFORMATION: Synthesized Oligonucleotide.

<400> SEQUENCE: 80
gataaaccga tacaattaaa ggctcc                                     26

<210> SEQ ID NO 81
<211> LENGTH: 15
<212> TYPE: PRT
<213> ORGANISM: Artificial Sequence
<220> FEATURE:
<223> OTHER INFORMATION: Synthesized Polypeptide.

<400> SEQUENCE: 81

Leu Phe Ala Ser Ser Asp Trp Ser Ser Phe Pro Val Leu Val Phe
1               5                   10                  15

<210> SEQ ID NO 82
<211> LENGTH: 23
<212> TYPE: DNA
<213> ORGANISM: Homo sapiens

<400> SEQUENCE: 82
tttatttcct gaccgtgctg agt                                        23

<210> SEQ ID NO 83

```
<211> LENGTH: 20
<212> TYPE: DNA
<213> ORGANISM: Homo sapiens

<400> SEQUENCE: 83
gacatgcaga agccgaaagg                                               20

<210> SEQ ID NO 84
<211> LENGTH: 25
<212> TYPE: DNA
<213> ORGANISM: Homo sapiens

<400> SEQUENCE: 84
tgaaccattg ccaggaaacg cacaa                                         25

<210> SEQ ID NO 85
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 85
ccaucuucca cguugcucac acugg                                         25

<210> SEQ ID NO 86
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 86
ucccacagag gauccaggca cuccu                                         25

<210> SEQ ID NO 87
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 87
augugacacu gccguucugc ucaga                                         25

<210> SEQ ID NO 88
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 88
ggaccuucua uagacucccu uggau                                         25

<210> SEQ ID NO 89
<211> LENGTH: 25
<212> TYPE: DNA
<213> ORGANISM: Artificial Sequence
<220> FEATURE:
<223> OTHER INFORMATION: Synthesized Oligonucleotide.

<400> SEQUENCE: 89
ggaauaagac auaauccugc aggcc                                         25
```

```
<210> SEQ ID NO 90
<211> LENGTH: 24
<212> TYPE: DNA
<213> ORGANISM: Homo sapiens

<400> SEQUENCE: 90
gaggatgagg agagctatga caca                                              24

<210> SEQ ID NO 91
<211> LENGTH: 22
<212> TYPE: DNA
<213> ORGANISM: Homo sapiens

<400> SEQUENCE: 91
ccctttgcac tcataacgtc ag                                                22

<210> SEQ ID NO 92
<211> LENGTH: 29
<212> TYPE: DNA
<213> ORGANISM: Homo sapiens

<400> SEQUENCE: 92
aaacacacag tcatcatagg gcagctcgt                                         29

<210> SEQ ID NO 93
<211> LENGTH: 15
<212> TYPE: PRT
<213> ORGANISM: Artificial Sequence
<220> FEATURE:
<223> OTHER INFORMATION: Synthesized Polypeptide.

<400> SEQUENCE: 93

Pro Leu Asp Trp Gly Leu Ile Pro Tyr Leu His Phe Gly Ser Val
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthesized Polypeptide.

<400> SEQUENCE: 94

Thr His Gly Phe Gly His Arg Val Trp Ser Val Pro Leu Arg Ser
1               5                   10                  15
```